US 11,879,141 B2

(12) United States Patent
Herber

(10) Patent No.: US 11,879,141 B2
(45) Date of Patent: *Jan. 23, 2024

(54) NUCLEIC ACID MOLECULES ENCODING CLOSTRIDIUM HISTOLYTICUM COLLAGENASE II AND METHODS OF PRODUCING THE SAME

(71) Applicant: ENDO GLOBAL VENTURES, Hamilton (GB)

(72) Inventor: Wayne K. Herber, Coopersburg, PA (US)

(73) Assignee: Endo Global Ventures, Hamilton (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/342,874

(22) Filed: Jun. 28, 2023

(65) Prior Publication Data

US 2023/0416717 A1 Dec. 28, 2023

Related U.S. Application Data

(60) Continuation of application No. 16/816,097, filed on Mar. 11, 2020, which is a continuation of application No. 15/669,286, filed on Aug. 4, 2017, now Pat. No. 10,603,365, which is a division of application No. 14/328,772, filed on Jul. 11, 2014, now Pat. No. 9,757,435, which is a continuation of application No. PCT/US2013/020940, filed on Jan. 10, 2013.

(60) Provisional application No. 61/585,909, filed on Jan. 12, 2012.

(51) Int. Cl.
| | |
|---|---|
| C12N 9/52 | (2006.01) |
| C12N 9/50 | (2006.01) |
| G01N 33/50 | (2006.01) |
| G01N 33/569 | (2006.01) |
| A61K 38/48 | (2006.01) |
| C12Q 1/37 | (2006.01) |

(52) U.S. Cl.
CPC ............... *C12N 9/52* (2013.01); *C12N 9/50* (2013.01); *C12Y 304/24003* (2013.01); *A61K 38/4886* (2013.01); *C12Q 1/37* (2013.01); *G01N 33/5044* (2013.01); *G01N 33/56911* (2013.01); *G01N 2333/96419* (2013.01); *Y02A 50/30* (2018.01)

(58) Field of Classification Search
CPC .............. C12N 9/52; C12Y 304/24033; A61K 38/4886
See application file for complete search history.

(56) References Cited

U.S. PATENT DOCUMENTS

| | | |
|---|---|---|
| 3,821,364 A | 6/1974 | Chiulli et al. |
| 4,338,000 A | 7/1982 | Kamimori et al. |
| 4,338,300 A | 7/1982 | Gelbard |
| 4,524,065 A | 6/1985 | Pinnell |
| 4,542,065 A | 9/1985 | Gaa |
| 4,645,668 A | 2/1987 | Pinnell |
| 4,732,758 A | 3/1988 | Hurion et al. |
| 5,252,461 A | 10/1993 | Weisbart |
| 5,252,481 A | 10/1993 | Holjevac et al. |
| 5,256,140 A | 10/1993 | Fallick |
| 5,332,503 A | 7/1994 | Lee et al. |
| 5,393,792 A | 2/1995 | Stern et al. |
| 5,422,103 A | 6/1995 | Stern et al. |
| 5,462,739 A | 10/1995 | Dan et al. |
| 5,514,340 A | 5/1996 | Lansdorp et al. |
| 5,514,370 A | 5/1996 | Stern et al. |
| 5,589,171 A | 12/1996 | Wegman |
| 5,705,170 A | 1/1998 | Kong et al. |
| 5,753,485 A | 5/1998 | Dwulet et al. |
| 5,753,785 A | 5/1998 | Reddy et al. |
| 5,830,741 A | 11/1998 | Dwulet et al. |
| 5,952,215 A | 9/1999 | Dwulet et al. |
| 5,989,888 A | 11/1999 | Dwulet et al. |
| 6,022,539 A | 2/2000 | Wegman |
| 6,086,872 A | 7/2000 | Wegman |
| 6,086,877 A | 7/2000 | Nishioka et al. |
| 6,086,887 A | 7/2000 | Parrott |
| 6,146,626 A | 11/2000 | Markert et al. |
| 6,280,993 B1 | 8/2001 | Yamato et al. |
| 6,335,388 B1 | 1/2002 | Fotinos |
| 6,358,539 B1 | 3/2002 | Murad |
| 6,475,764 B1 | 11/2002 | Burtscher et al. |
| 6,953,583 B1 | 10/2005 | Ghisalberti |
| 6,958,150 B2 | 10/2005 | Wegman et al. |
| 7,083,964 B2 | 8/2006 | Kurfuerst et al. |

(Continued)

FOREIGN PATENT DOCUMENTS

| | | |
|---|---|---|
| AU | 2006206393 A1 | 7/2006 |
| BR | PI0607280-1 A2 | 8/2009 |

(Continued)

OTHER PUBLICATIONS

Hexsel et al., "Noninvasive Treatment of Cellulite Utilizing an Expedited Treatment Protocol with a Dual Wavelength Laser-suction and Massage Ddevice", Journal of Cosmetic and Laser Therapy, 2013, vol. 15, pp. 65-69.

(Continued)

*Primary Examiner* — Zachary C Howard
(74) *Attorney, Agent, or Firm* — BakerHostetler

(57) ABSTRACT

The invention relates to recombinant nucleic acid and polypeptides encoding collagenase I and collagenase II, methods for the preparation thereof and methods for the use thereof. The invention also encompasses methods related to releasing a composition comprising collagenase prior to therapeutic administration.

10 Claims, 28 Drawing Sheets

Specification includes a Sequence Listing.

(56) References Cited

U.S. PATENT DOCUMENTS

| | | | |
|---|---|---|---|
| RE39,941 E | 12/2007 | Wegman | |
| 7,355,027 B2 | 4/2008 | Brehm et al. | |
| 7,358,067 B2 | 4/2008 | Vrang et al. | |
| 7,622,130 B2 | 11/2009 | Kolodney et al. | |
| 7,811,560 B2 | 10/2010 | Sabatino et al. | |
| 7,824,673 B2 | 11/2010 | Wegman et al. | |
| 7,842,673 B2 | 11/2010 | Brink et al. | |
| 7,854,929 B2 | 12/2010 | Badalemente et al. | |
| 8,323,643 B2 | 12/2012 | Badalamente et al. | |
| 8,380,531 B2 | 2/2013 | Paty et al. | |
| 9,757,435 B2 | 9/2017 | Herber | |
| 10,119,131 B2 | 11/2018 | Wegman et al. | |
| 10,123,959 B2 | 11/2018 | Badalamente et al. | |
| 10,603,365 B2 * | 3/2020 | Herber | C12Q 1/37 |
| 2002/0036328 A1 | 3/2002 | Richards et al. | |
| 2003/0022856 A1 | 1/2003 | Richardson et al. | |
| 2003/0026844 A1 | 2/2003 | Lee et al. | |
| 2003/0129178 A1 | 7/2003 | Wegman et al. | |
| 2004/0137596 A1 | 7/2004 | Kurfuerst et al. | |
| 2005/0227910 A1 | 10/2005 | Yang et al. | |
| 2005/0261584 A1 | 11/2005 | Eshel et al. | |
| 2005/0267080 A1 | 12/2005 | Kolodney et al. | |
| 2006/0020448 A1 | 1/2006 | Chelba et al. | |
| 2006/0204488 A1 | 9/2006 | Badalamente | |
| 2006/0241673 A1 | 10/2006 | Zadini et al. | |
| 2006/0251581 A1 | 11/2006 | Mcintyre et al. | |
| 2007/0003541 A1 | 1/2007 | Faudoa et al. | |
| 2007/0031482 A1 | 2/2007 | Castro et al. | |
| 2007/0224183 A1 | 9/2007 | Sabatino et al. | |
| 2007/0224184 A1 | 9/2007 | Badalemente et al. | |
| 2008/0020001 A1 | 1/2008 | Brehm et al. | |
| 2008/0206228 A1 | 8/2008 | Vaccaro et al. | |
| 2008/0233614 A1 | 9/2008 | Cranenburgh et al. | |
| 2008/0279900 A1 | 11/2008 | Longo et al. | |
| 2008/0300429 A1 | 12/2008 | Sakanishi et al. | |
| 2009/0053276 A1 | 2/2009 | Richard | |
| 2010/0015262 A1 | 1/2010 | Goralczyk et al. | |
| 2010/0021416 A1 | 1/2010 | Lichter et al. | |
| 2010/0035868 A1 | 2/2010 | Jabbour | |
| 2010/0086971 A1 | 4/2010 | Suppmann et al. | |
| 2010/0137747 A1 | 6/2010 | Thomas et al. | |
| 2010/0159564 A1 | 6/2010 | Dwulet et al. | |
| 2010/0233150 A1 | 9/2010 | Wegman et al. | |
| 2010/0233151 A1 | 9/2010 | Sabatino et al. | |
| 2010/0330065 A1 | 12/2010 | Sabatino et al. | |
| 2011/0070622 A1 | 3/2011 | Hoelke et al. | |
| 2011/0158972 A1 | 6/2011 | Sabatino et al. | |
| 2011/0160617 A9 | 6/2011 | Thomas et al. | |
| 2011/0189153 A1 | 8/2011 | Sabatino et al. | |
| 2011/0189163 A1 | 8/2011 | Sabatino et al. | |
| 2011/0217252 A1 | 9/2011 | Koverech | |
| 2011/0243908 A1 | 10/2011 | Sabatino et al. | |
| 2011/0243909 A1 | 10/2011 | Sabatino et al. | |
| 2011/0243919 A1 | 10/2011 | Sabatino et al. | |
| 2011/0243920 A1 | 10/2011 | Sabatino et al. | |
| 2011/0262508 A1 | 10/2011 | Watt et al. | |
| 2011/0294192 A1 | 12/2011 | Fukushima et al. | |
| 2012/0164131 A1 | 6/2012 | Huang et al. | |
| 2012/0237492 A1 | 9/2012 | Walker | |
| 2012/0237497 A1 | 9/2012 | Wegman et al. | |
| 2012/0315265 A1 | 12/2012 | Lai et al. | |
| 2013/0096596 A1 | 4/2013 | Schafer | |
| 2013/0129663 A1 | 5/2013 | Friberg et al. | |
| 2013/0195828 A1 | 8/2013 | Kibbe et al. | |
| 2013/0217789 A1 | 8/2013 | Taylor et al. | |
| 2013/0287759 A1 | 10/2013 | Munoz Montano | |
| 2014/0004094 A1 | 1/2014 | Sabatino et al. | |
| 2014/0271508 A1 | 9/2014 | Florence et al. | |
| 2014/0271612 A1 | 9/2014 | Leppert et al. | |
| 2014/0335072 A1 | 11/2014 | Hart | |
| 2015/0010532 A1 | 1/2015 | Herber | |
| 2015/0301064 A1 | 10/2015 | Yoshida et al. | |
| 2016/0000890 A1 | 1/2016 | Yu et al. | |
| 2016/0279046 A1 | 9/2016 | Badalamente et al. | |
| 2017/0136039 A1 | 5/2017 | Jung et al. | |
| 2017/0209201 A1 | 7/2017 | Slayton et al. | |
| 2017/0228517 A1 | 8/2017 | Saliman et al. | |
| 2017/0290848 A1 | 10/2017 | Walker | |
| 2017/0319601 A1 | 11/2017 | Walker | |
| 2019/0240253 A1 | 8/2019 | Abst et al. | |
| 2022/0119791 A1 | 4/2022 | Sheaffer et al. | |

FOREIGN PATENT DOCUMENTS

| | | |
|---|---|---|
| CA | 2308842 A1 | 12/2000 |
| CA | 2643171 A1 | 9/2007 |
| CN | 1529751 A | 9/2004 |
| CN | 101684461 A | 3/2010 |
| EP | 0468411 A2 | 1/1992 |
| EP | 1433845 A1 | 6/2004 |
| EP | 2130551 | 12/2009 |
| EP | 2133415 A1 | 12/2009 |
| EP | 2180002 A1 | 4/2010 |
| EP | 2363461 A1 | 9/2011 |
| FR | 2788682 A1 | 7/2000 |
| IL | 192878 A | 3/2013 |
| JP | 61-289885 A | 12/1986 |
| JP | 03-091478 A | 4/1991 |
| JP | 05-219942 A | 8/1993 |
| JP | 06-237764 A | 8/1994 |
| JP | 08-500970 A | 2/1996 |
| JP | 09-508026 A | 8/1997 |
| JP | 10-262658 A | 10/1998 |
| JP | 11-501517 A | 2/1999 |
| JP | 11-504225 A | 4/1999 |
| JP | 2002-530873 A | 9/2002 |
| JP | 2003-284553 A | 10/2003 |
| JP | 2004-535197 A | 11/2004 |
| JP | 2005-006552 A | 1/2005 |
| JP | 2006-254876 A | 9/2006 |
| JP | 2008-500970 A | 1/2008 |
| JP | 2009-525283 A | 7/2009 |
| JP | 2009-291195 A | 12/2009 |
| JP | 2010-262658 A | 11/2010 |
| JP | 2011-504225 A | 2/2011 |
| JP | 2011-528716 A | 11/2011 |
| JP | 5309289 B2 | 10/2013 |
| JP | 2014-530873 A | 11/2014 |
| JP | 6496386 B2 | 4/2019 |
| KR | 10-2008-0093142 A | 10/2008 |
| KR | 10-2009-0125705 A | 12/2009 |
| KR | 10-2011-0046537 A | 5/2011 |
| RU | 2180002 C2 | 2/2002 |
| WO | 94/00580 A1 | 1/1994 |
| WO | 94/16086 A1 | 7/1994 |
| WO | 96/00283 A1 | 1/1996 |
| WO | 96/28543 A1 | 9/1996 |
| WO | 98/10079 A1 | 3/1998 |
| WO | 98/24889 A1 | 6/1998 |
| WO | 00/30182 A2 | 5/2000 |
| WO | 01/21574 A1 | 3/2001 |
| WO | 03/04628 A2 | 1/2003 |
| WO | 2004/085643 A1 | 10/2004 |
| WO | 2005/073367 A1 | 8/2005 |
| WO | 2005/123764 A1 | 12/2005 |
| WO | 2006/002646 A2 | 1/2006 |
| WO | 2006/010057 A2 | 1/2006 |
| WO | 2006/025226 A1 | 3/2006 |
| WO | 2006/078870 A2 | 7/2006 |
| WO | 2006/121968 A2 | 11/2006 |
| WO | 2007/089851 A2 | 8/2007 |
| WO | 2007/100590 A2 | 9/2007 |
| WO | 2007/100675 A2 | 9/2007 |
| WO | 2008/101406 A1 | 8/2008 |
| WO | 2010/011605 A2 | 1/2010 |
| WO | 2011/073925 A2 | 6/2011 |
| WO | 2011/130537 A2 | 10/2011 |
| WO | 2012/031245 A1 | 3/2012 |
| WO | 2012/041512 A1 | 4/2012 |
| WO | 2013/059619 A1 | 4/2013 |
| WO | 2015/108901 A1 | 7/2015 |

(56) References Cited

FOREIGN PATENT DOCUMENTS

| WO | 2018/160905 A1 | 9/2018 |
| WO | 2018/183582 A2 | 10/2018 |

OTHER PUBLICATIONS

Hexsel et al., "Side-By-Side Comparison of Areas with and without Cellulite Depressions Using Magnetic Resonance Imaging," Dermatol. Surg. 2009, vol. 35, pp. 1471-1477.
High Performance Liquid Chromatography (HPLC) Tutorial, 2012, pp. 1-7.
Hiroshi et al., "Cloning a neutral protease of Clostridium histolyticum, determining its substrate specificity, and designing a specific substrate", Applied Microbiology And Biotechnology, Springer, DE, 2015, vol. 99, No. 24, pp. 10489-10499.
Hulstyn et al., "Adhesive capsulitis of the shoulder", Orthopaedic Review, 1993, pp. 425-433.
Hurst et al., "Injectable clostridial collagenase: striving toward nonoperative treatment options for fibroproliferative disorders," 2009, pp. 1-30, available at http://www.aaos.org/research/committee/research/Kappa/KD2009.sub.--Hurst.pdf.
Hurst et al., "Injectable Collagenase Clostridium Histolyticum for Dupuytren's Contracture", N Engl J Med. 2009, vol. 361, No. 10, pp. 968-979.
Hutchinson et al., "Dupuytren's Disease and Frozen Shoulder Induced by Treatment with a Matrix Metalloproteinase Inhibitor," The Journal of Bone and Joint Surgery, 1998, vol. 80B, No. 5 pp. 907-908.
Ibrahim-Grant et al., "Expression of PZ-Peptidases by Cultures of Several Pathogenic Fungi. Purification and Characterization of a Collagenase from Trichophyton Schoenleinii", Journal of Medical & Veterinary Mycology, 1996, vol. 34, pp. 83-90.
Imhof et al., "A Phase III Study of IncobotulinumtoxinA in the Treatment of Glabellar Frown Lines", J Clin Aesthet Dermatol, 2011, vol. 4, No. 10, pp. 28-34.
Information Related to ClinicalTrials.gov Identifier: NCT01518907, "The Safety, Effectiveness, and Pharmacokinetics of AA4500 for the Treatment of Edematous Fibrosclerotic Panniculopathy (Commonly Known as Cellulite)", pp. 1-9 first Posted: Jan. 26, 2012.
Ippolito et al., "Experimental Study on the Use of Collagenase in Localized Connective Tissue Fibrosis", Database EMBASE on STN., 1976, Acc. No. 1976196184, pp. 279-290.
Iwahashi et al., "Immunohistochemical analysis of collagen expression in uterine leiomyornata during the D menstrual cycle," Experimental and Therapeutic Medicine, 2011, vol. 2, pp. 287-290.
Jang et al., "The Anti-Wrinkle and Whitening Effect of Extracts of Castanea crenata Inner Shell," Journal of Life Science, 2011, vol. 21, No. 5, pp. 734-738.
Jayes et al., "Loss of stiffness in collangen-rich uterine fibroids after digestion with purified collagenase Clostridium histolyticum," American Journal of Obstetrics & Gynecology, 2016, vol. 1.e1, pp. 1-8.
Jin et al., "Reversibility of Experimental Rabbit Liver Cirrhosis by Portal Collagenase Administration", Laboratory Investigation, 2005, vol. 85, pp. 992-1002.
Jung et al., "Identification of Metal Ligands in the Clostridium histolyticum ColH Collagenase," J. of Bacteriology, 1999, vol. 181, No. 9, pp. 2816-2822.
Jung et al., "Expression of the colH gene encoding clostridium histolyticum collagenase in bacillus subtilis and its application to enzyme purification," Microbial. Immunol., 1996, vol. 40, No. 12, pp. 923-929.
Kaplan et al., "Predictors of recurrence for joints successfully treated with collagenase clostridium histolyticum injections", Podium presented at the 39th Annual Meeting of the American Society for Hand Therapists (ASHT), 2016, pp. 1-3.
Keil et al., "Some Newly Characterized Collagenases from Procaryotes and Lower Eucaryotes," Entrez Pubmed Abstract, 1979, vol. 23, pp. 87-108.
Kembhavi et al., "Clostripain: Characterization of the Active Site," FEBS Letters, 1991, vol. 283, Issue 2, pp. 277-280.
Khan et al., "Treatment of cellulite: Part I. Pathophysiology," J. Am. Acad. Dermatol., 2010, vol. 62, No. 3, pp. 361-370.
Kikuchi et al., "Intra-articular injection of collagenase induces experimental osteoarthritis in mature rabbits", Osteoarthritis and Cartilage, 1998, vol. 6, pp. 177-186.
Kilian et al., "The frozen shoulder. 1-10 Arthroscopy, histological findings and transmission electron microscopy imaging", Der Chirurg; Zeitschrift Fur Alle Gebiete Der Operativen Medizen, 2001, vol. 72, No. 11, pp. 1303-1308.
Kirby et al., "Assessing cellulite severity: method for assessing reliability of a new clinician-reported and a new patient-reported photonumeric scale", Poster presented at the International Society of Pharmacoeconomics and Outcomes Research (ISPOR), 2018, 1 page.
Kooi et al., "Differentiation of Thermolysins and Serralysins by Monoclonal Antibodies", J. Med. Microbiol., 1996, vol. 45, pp. 219-225.
Kooi et al., "Identification of Neutralizing Epitopes on Pseudomonas aeruginosa Elastase and Effects of Cross-Reactions on Other Thermolysin-Like Proteases," Infection and Immunity, 1997, vol. 65, No. 2, pp. 472-477.
Krishna et al., "Immunogenicity to Biotherapeutics—The Role Of Anti-Drug Immune Complexes", Frontiers In Immunology, 2016, vol. 7, Article 21, pp. 1-13.
Kurnik et al., "Buffer Exchange Using Size Exclusion Chromatography, Countercurrent Dialysis, and Tangential Flow Filtration: Models, Development and Industrial Application", Biotechnology and Bioengineering, 1995, vol. 45, pp. 149-157.
Kuwayama, "Enhancement of Homologous Recombination Efficiency by Homologous Oligonucleotides", Cell Interaction; Chapter 9, 2012, pp. 233-244.
Labrou et al., "The Structure-Function Relationship in the Clostripain Family of Peptidase," Eur. J. Biochem, 2004, vol. 271, pp. 983-992.
Lecroisey et al., "Purification, Stability and Inhibition of the Collagenase from Achromobacter lophagus", Febs Letters, 1975, vol. 59, No. 2, pp. 167-172.
Leppert et al., "Comparative ultrastructure of collagen fibrils in uterine leiomyomas and normal myometrium", Fertil Steril, 2004vol. 82, No. 3, pp. 1182-1187.
Leppert et al., "The Extracellular Matrix Contributes to Mechanotransduction in Uterine Fibroids", Hindawi Publishing Corporation, 2014, vol. 2014, Article ID 783289, pp. 1-12.
Lola et al., "Quantitative model of cellulite: Three-dimensional skin surface topography, biophysical characterization, and relationship to human perception", J. Cosmet. Set., 2005, vol. 56, pp. 105-120.
Lukac et al., "The Metalloenzymic Nature of Collagenase-Like Peptidase of the Rat Testis", J Reprod. Fert., 1977, vol. 49, pp. 95-99.
MacLennan, "The Histotoxic Clostridial Infections of Man," Bacteriol. Rev., 1962, vol. 26, pp. 177-274.
Madan et al., "In situ forming polymeric drug delivery systems," Indian Journal of Pharmaceutical Sciences, 2009, vol. 71, No. 3, pp. 242-251.
Mandl et al., "Multiplicity of Clostridium histolyticum Collagenases", Biochemistry, 1964, vol. 3, pp. 1737-1741.
Matsushita et al., "Gene Duplication and Multiplicity of Collagenases in Clostridium histolyticum," J. of Bacteriology, 1999, vol. 181, No. 3, pp. 923-933.
Matsushita et al., "Substrate recognition by collagen-binding domain of Clostridium histolyticum Class I Collagenase", J Biol Chem, vol. 278, No. 12, pp. 8761-8770.
McLane et al., "Analysis of potential impact of healthcare provider gender on rating cellulite severity", The American Society of Plastic Surgeons (ASPS) Aesthetica, 2018, pp. 1-3.
McLane et al., "Assessing Cellulite Severity: Test-Retest Reliability of and Concordanance Between New Clinician Reported and Patient Reported Photonumeric Scales", The American Society of Plastic Surgeons (ASPS) 97th Annual Meeting, 2018, pp. 1-3.
McMahon et al., "Pharmacokinetics, Clinical Efficacy, Safety Profile, and Patient-Reported Outcomes in Patients Receiving Subcu-

(56) References Cited

OTHER PUBLICATIONS taneous Testosterone Pellets 900 mg for Treatment of Symptoms Associated With Androgen Deficiency", J Sex Med., 2017, vol. 14, No. 7, pp. 883-890.
MedlinePlus "Cellulite," http://www.nlm.nih.gov/medlineplus/encv/article/002033.htm, updated Oct. 10, 2010, pp. 1-2.
Melton-Witt et al., "Identification of Functional Domains of Clostridium septicum Alpha Toxin," Biochem., 2006, vol. 45, No. 48, pp. 14347-14354.
Muppavarapu et al., "Clinical outcomes following collagenase injections compared to fasciectomy in the treatment of Dupuytren's contracture," Hand, 2015, vol. 10, No. 2, pp. 260-265.
Naam NH. "Functional outcome of collagenase injections compared with fasciectomy in treatment of Dupuytren's contracture", Hand, 2013, vol. 8, No. 4, pp. 410-416.
Narins et al., "A randomized, double-blind, multicenter comparison of the efficacy and tolerability of restylane versus zyplast for the correction of nasolabial folds", Dermatol Surg, 2003, vol. 29, No. 6, pp. 588-595.
National Library of Medicine "MeSH Descriptor Data—Hyaluronoglucosaminidase," http://www.nlm.nih.gov/cgi/mesh/2008/MB_cgi?mode=&term=hyaluronidase, 1 page, 2008.
Newsday Article—"Promising New Treatments For Stiff-Shoulder Condition", published on Oct. 2, 2001, p. 1.
Nguyen et al., "Injectable biodegradable hydrogels," Macromol. Biosci., 2010, vol. 10, pp. 563-579.
Nielsen et al., "Prediction of Signal Peptides and Signal Anchors by a Hidden Markov Model," AAAI Press, 1998, pp. 122-130.
Norian et al., "Characterization of tissue biomechanics and mechanical signaling in uterine leiomyoma," Matrix Biol., 2011, vol. 31, No. 1, pp. 57-65.
Nydick et al., "A comparison of percutaneous needle fasciotomy and collagenase injection for dupuytren disease", J Hand Surg Am., 2013, vol. 38, No. 12, pp. 2377-2380.
O'Donohue et al., "Cloning and Expression in Bacillus subtilis of the NPR Gene from Bacillus thermoproteolyticus Rokko Coding for the Thermostable Metalloprotease Thermolysin", Biochem. J., 1994, vol. 300, pp. 599-603.
O'Donohue et al., "The Roles of the Prosequence of Thermolysin in Enzyme Inhibition and Folding in Vitro," J. Biol. Chem., 1996, vol. 271, No. 43, pp. 26477-26481.
Obgyn.Net Headline News, Successful phase II results lead to phase III approval—Dupuytren disease. Posted at the web on Oct. 8, 2001, (at the web: http://www.obgyn.net/newsrx/general_h ealth-dupuytren_ disease-20011008-21.asp), especially pp. 1-2, last paragraph.
Omi et al., "Ultrastructural Assessment of Cellulite Morphology: Clues to a Therapeutic Strategy?" Laser Therapy, 2013, vol. 22, No. 2, pp. 131-136.
Oppenheim et al., "A modified procedure for the purification of clostridial collagenase", Preparative Biochemistry and Biotechnology, 1978, vol. 8, No. 5, pp. 387-407.
Pall BioPharmaceuticals, "Mustang Q Capsule: The Only Disposable Process Chromatography col. for Pharmaceutical Manufacturing", Pharmaceutical Online, 2000, 1 page.
Peavey et al., "Collagen-Binding .alpha. II Integrin Expression in Human Myometrium and Fibroids Utilizing a Novel RNA in Situ Probe," Reproductive Sciences, 2014, vol. 21, No. 9, pp. 1139-1144.
Peimer et al., "Dupuytren contracture recurrence following treatment with collagenase clostridium histolyticum (CORDLESS [Collagenase Option for Reduction of Dupuytren Long-Term Evaluation of Safety Study]): 5-year data", J Hand Surg Am., 2015, vol. 40, No. 8, pp. 1597-1605.
Povlsen et al., "What is the better treatment for single digit dupuytren's contracture: surgical release or collagenase clostridium histolyticum (Xiapex) injection?," Hand Surg, 2014 vol. 19, No. 3, pp. 389-392.
Press Release, "Auxilium Pharmaceuticals, Inc. Announces First Patients Dosed in Xiaflex Phase IB Cellulite Study", Exhibit-5, Jan. 26, 2012; pp. 1-7; downloaded from: https://www.pmewswire.com/news-releases/auxilium-pharmaceuticals-inc-announces-first-patients-dosed-in-xiaflex-phase-ib-cellulite-study-138113223.html.
Press Release, "Auxilium Pharmaceuticals, Inc. Announces First Patients Dosed in Xiaflex Phase lb Cellulite Study", Exhibit-1, Jan. 26, 2011; pp. 1-4; downloaded from: https://www.sec.gov/Archives/edgar/data/1182129/000119312512024205/d290313dex991.htm.
Press Releases, "Endo Announces Positive Results from Phase 3 Studies of Collagenase Clostridium Histolyticum (CCH) in Patients with Cellulite", Exhibit-2, 2018, pp. 1-3.
Priestley et al., "Converting from Transdermal to Buccal Formulations of Buprenorphine: A Pharmacokinetic Meta-Model Simulation in Healthy Volunteers", Pain Med., 2018, vol. 19, No. 10, pp. 1988-1996.
Proprietary Product Name: Xiaflex, "Australian Public Assessment Report for Collagenase clostridium histolyticum", Australian Government, Department of Health, Therapeutic Goods Administration, Sponsor: Actelion Pharmaceuticals Australia Pty Ltd, Nov. 2013, pp. 1-83.
Protein I—Separation, Purification, and Property—, edited by Japan Biochemical Society, 1st Edition, 1st Issue, published by Tokyo Kagaku Dojin, Feb. 26, 1990, pp. 161-169.
Q6A Specifications, "Test procedures and acceptance guidance criteria for new drug substances and new drug products", Chemical Substances, 2000, vol. 65, No. 251, pp. 83041-83063.
Queiroz et al., "Hydrophobic Interaction Chromatography of Proteins", Journal of Biotechnology, 2001, vol. 87, pp. 143-159.
Querleux et al., "Anatomy and physiology of subcutaneous adipose tissue by in vivo magnetic resonance imaging and spectroscopy: relationships with sex and presence of cellulite", Skin Res Technol., 2002, vol. 8, No. 2, pp. 118-124.
Ralph et al., "Collagenase clostridium histolyticum in combination with vacuum therapy in patients with Peyronie's disease", Podium presented at the 22nd Annual Fall Scientific Meeting of the Sexual Medicine Society of North America (SMSNA); Nov. 3-6, 2016; Scottsdale, AZ, 1 page.
Ralph et al., "The safety and efficacy of collagenase clostridium histolyticum (CCH) in combination with vacuum therapy for the treatment of Peyronie's disease", 2017, vol. 14, pp. 1430-1437.
Ralph et al., "The safety and efficacy of collagenase clostridium histolyticum in combination with vacuum therapy for the treatment of Peyronie's disease", Podium presented at the 112th Annual Meeting of the American Urological Association (AUA), May 12-16, 2017, 1 page.
Ralph et al., "Treatment of Peyronie's Disease With Collagenase Clostridium histolyticum and Vacuum Therapy: A Randomized, Open-Label Pilot Study", J Sex Med. 2017, vol. 14, No. 11, pp. 1430-1437.
Roche Applied Science, The Complete Guide for Protease Inhibition, 2004, pp. 1-12.
Rogers et al., "Mechanical homeostasis is altered in uterine leiomyoma," Am. J. Obstet. Gynecol., 2008, vol. 198, No. 4, pp. 474.e1-474.11.
Rotunda et al., "Mesotherapy and phosphatidycholine injections: historical clarification and review", Dematologic Surgery: Official Publication for American Society for Dermatologic Surgery, 2006, vol. 32, No. 4, pp. 465-480.
Sadick et al., "Collagenase Clostridium Histolyticum for the Treatment of Edematous Fibrosclerotic Panniculopathy (Cellulite): A Randomized Trial", Dermatol Surg., 2019 vol. 45, pp. 1047-1056.
Sadick et al., Comparisons of Clinical Reported and Patient Reported Cellulite Severity Scales With Existing Scales for Measurement of Cellulite Severity, Maui Derm 2018, pp. 1-33.
Sadick et al., "Comparisons of Clinician Reported and Patient Reported Cellulite Severity Scales With Existing Scales for Measurement of Cellulite Severity", Poster presented at the 2017 American Society for Dermatologic Surgery Annual Meeting (ASDS), 2017; Chicago, IL, 1 page.
Sadick et al., "Efficacy and Safety Evaluation of Collagenase Clostridium Histolyticum for the Treatment of Edematous Fibrosclerotic Panniculopathy", Poster presented at the Maui Derm For Dermatologist, Jan. 28-Feb. 1, 2018; Maui, HI, 1 page.
Sadick, "New measurement and treatment options for edematous fibrosclerotic panniculopathy (cellulite): results from a randomized,

(56) References Cited

OTHER PUBLICATIONS double-blind, placebo-controlled trial of CCH", Podium presented by Dr. John Joseph at the Vegas Cosemetic Surgery (VCS); Jun. 6-10, 2018, NV, pp. 1-2.
Sasaki, "Single Treatment of Grades II and III Cellulite Using a Minimally Invasive 1,440-nm Pulsed Nd:YAG Laser and Side-Firing Fiber: An Institutional Review Board-Approved Study witha 24-Month Follow-Up Period", published on Oct. 11, 2013, vol. 37, pp. 1073-1089.
Scherman et al., "One-year results of needle fasciotomy and collagenase injection in treatment of Dupuytren's contracture: A two-centre prospective randomized clinical trial, "J Hand Surg Eur, 2016, vol. 41, No. 6, pp. 577-582.
Serefoglu et.al., "Factors Associated With Erectile Dysfunction and the Peyronie's Disease Questionnaire in Patients With Peyronie Disease", Urology, 2017, vol. 107, pp. 155-160.
Shimada et al., "C-terminal Amino Acid Residues are Required for the Folding and Cholesterol Binding Property of Perfringolysin O, a Pore-forming Cytolysin," The Journal of Biological Chemistry, 1999, vol. 274, No. 26, pp. 18536-18542.
Siegel et al., "Adhesive Capsulitis: A Sticky Issue", American Family Physician, 1999, vol. 59, No. 7, pp. 1843-1852,.
Sigma Aldrich, "Collagenase Guide", 2005, pp. 1-4.
Skov et al., "Injectable Collagenase Versus Percutaneous Needle Fasciotomy for Dupuytren Contracture in Proximal Interphalangeal Joints: A Randomized Controlled Trial", J Hand Surg Am., 2017, vol. 42, No. 5, pp. 321-328.
Smalls, "Development of Quantitative Modes for the Investigation of Gynoid Lipodystrophy (Cellulite)", Ph.D. Thesis, University of Cincinnati, Apr. 21, 2005, pp. 1-210.
Smalls, "Effect of Weight Loss on Cellulite: Gynoid Lypodystrophy", Plast. Reconstr. Surg., 2006, vol. 118, No. 2, pp. 510-516.
Smith et al., "A multicenter, double-blind, placebo-controlled trial of autologous fibroblast therapy (Azficel-T) for the treatment of nasolabial fold wrinkles", Dermatol Surg., 2012, vol. 38, No. 7, pp. 1234-1243.
Soledad et al., "Mechanical Signaling in Reproductive Tissues: Mechanisms and Importance," Reproductive Sciences, 2014, vol. 21, No. 9, pp. 1093-1107.
Specific Activity—https://terms.naver.com/entry.nhn?docId=1913800&cid=50314&categoryId=50314, dated Jun. 10, 2017, pp. 1-3.
Specific Activity—Reference Material—Korean Appeal Suit case for Korean Patent Application No. 10-2011-7006197, 2017, pp. 1-3.
Declaration of Thomas Wegman and Bo Yu dated Mar. 13, 2013 and Filed in U.S. Appl. No. 13/713,019.
Akers, "Excipient-Drug Interactions in Parenteral Formulations," J. Pharm. Sci., 2002, vol. 91, No. 11, pp. 2283-2300.
Almeida et al., "Intra- and inter-observer reliability of the application of the cellulite severity scale to a Spanish female population : CSS reliability in a Spanish female population", Jeadv. Journal of the european academy of dermatology and venereology., vol. 27, No. 6, Apr. 6, 2012, pp. 694-698.
Angleton et al., "Preparation and Reconstitution with Divalent Metal Ions of Class I and Class II Clostridium histolyticum Apocollagenases", Biochemistry 1988, vol. 27, pp. 7406-7412.
Anonymous: "Stony Brook Announces New Clinical Trial with BioSpecifics Injectable Collagenase for Adhesive Capsulitis," (Oct. 2000); Retrieved from the Internet Oct. 12, 2015, pp. 1-3.
Apostol et al., "Uncertainty Estimates of Purity Measurements Based on Current Information: Toward a "Live Validation" of Purity Methods", Pharm Res, 2012, pp. 1-16.
Assessment Report, Xiapex, Common name: Collagenase clostridium histolyticum, Procedure No. EMEA/H/C/2048, 2011, pp. 1-71.
Atroshi et al., "Costs for collagenase injections compared with fasciectomy in the treatment of Dupuytren's contracture: a retrospective cohort study," BMJ Open. 2014, vol. 4, No. 1:e004166, pp. 1-7.
Avram, "Cellulite: a review of its physiology and treatment," J Cosmet Laser Ther., 2004, vol. 6, No. 4, pp. 181-185.

Badalamente et al., "Collagen as a clinical target: Nonoperative treatment of dupuytren's disease" The Journal of Hand Surgery, W.B. Saunders, 2002, vol. 27, No. 5, pp. 788-798.
Badalamente et al., "Efficacy and Safety of Injectable Mixed Collagenase Subtypes in the Treatment of Dupuytren's Contracture", The J. of Hand Surgery, 2007, vol. 32A, No. 06, pp. 767-774.
Badalamente et al., "Enzyme injection as a nonoperative treatment for Dupuytren's disease", Drug Delivery, 1996, vol. 3, pp. 35-40.
Badalamente et al., "Enzyme Injection as Nonsurgical Treatment of Dupuytren's Disease," The Journal of Hand Surgery, 2000, vol. 25A, No. 4, pp. 629-636.
Bains et al., "Primary frozen shoulder, The untold story!", Journal of Bone and Joint Surgery, 2006, vol. 90-B, Supp. sub.-II, 1 page.
Balci et al., "Shoulder Adhesive Capsulitis and shoulder range of motion in Type II Diabetes Mellitus: association with diabetic complications", Journal Of Diabetes And Its Complications, Elsevier Science, New York, 1999, vol. 13, pp. 135-140.
Ballard et al., "Purification and Characterization of the Lethal Toxin (Alpha-Toxin) of Clostridium septicum," Infection and Immunity, 1990, vol. 60, No. 3 pp. 784-790.
Bauer et al., "Non-contact thermal imaging as potential tool for personalized diagnosis and prevention of cellulite", Journal of Thermal Analysis and Calorimetry, 2018, vol. 133, pp. 571-578.
BD BioPharmaceutical Production, "Bionutrient Technical Manual", Second Eddition, Mar. 2004, pp. 1-13.
Bear et al., "Treatment of Recurrent Dupuytren Contracture in Joints Previously Effectively Treated with Collagenase Clostridium Histolyticum", J Hand Surg Am., 2017, vol. 42, No. 5, pp. 391.e1-391.e8.
Behera et al., "Thrombospondin-1 and Thrombospondin-2 mRNA and TSP-1 and TSP-2 Protein Expression in Uterine Fibroids and Correlation to the Genes COL1A1 and COL3A1 and to the Collagen Cross-link Hydroxyproline," Reproductive Sciences., 2007, vol. 14, No. 8S, pp. 63-76.
Bielfeldt et al., "Non-invasive evaluation techniques to quantify the efficacy of cosmetic anti-cellulite products", Skin Research and Technology 2008, vol. 14, pp. 336-346.
Billington et al., "Thiol-Activated Cytolysins: Structure, Function and Role in Pathogenesis," FEMS Microbiol. Lett., 2000, vol. 182, No. 2, pp. 197-205.
Bio-Rad, "Chromatography Column Performance and Data Analysis Success Guide", Jun. 2014, pp. 1-17.
Bond et al., "Characterization of the Individual Collagenases from Clostridium Histolyticum", Biochemistry, 1984, vol. 23, pp. 3085-3091.
Bond et al., "Purification and separation of individual collagenases of clostridium histolyticum using red dye ligand chromatography," Biochemistry 1984, vol. 23, pp. 3077-3085.
Bonnerjea et al., "Protein purification: the right step at the right time;" Biotechnology, 1986, vol. 4, pp. 954-958.
Bowen, "A Comparison of the Lethal and Hemolytic Toxins of Clostridium Histolyticum," Yale J. Biol. Med., 1952, vol. 25, No. 2, pp. 124-138.
Brandhorst et al., "Adjustment of the Ratio Between Collagenase Class Ii and I Improves Islet Isolation Outcome," Transplantation Proceedings, 2005, vol. 37, pp. 3450-3451.
Brandhorst et al., "The ratio between collagenase class I and class Ii influences the efficient islet release from the rat pancreas", Transplantation, 2008, vol. 85, No. 3, pp. 456, 457.
Brandt et al., "Safety and Effectiveness of Small and Large Gel-Particle Hyaluronic Acid in the Correction of Perioral Wrinkles", J Drugs Dermatol., 2011, vol. 10, No. 9, pp. 982-987.
Brunengraber et al., "Injectable Clostridium Histolyticum Collagenase as a Potential Treatment for Uterine Fibroids", Reproductive Sciences, 2014, vol. 21, No. 12, pp. 1452-1459.
Buhren et al., "Hyaluronidase: From Clinical Applications to Molecular and Cellular Mechanisms," Eur. J. Med. Res. 2016, vol. 21, No. 5, pp. 1-8.
Bunker et al., "The pathology of frozen shoulder. A Dupuytren-like disease", The Journal of Bone and Joint Surgery.British Volume Sep. 1995, vol. 77, No. 5, pp. 677-683.
Bunker, "Frozen shoulder: unravelling the enigma", Ann R Coll Surg Engl, 1997, vol. 79, pp. 210-213.

(56) References Cited

OTHER PUBLICATIONS

Callaghan III et al., "Cellulite: a review of pathogenesis-directed therapy", Seminars in Cutaneous Medicine and Surgery, Dec. 2017, vol. 36, pp. 179-184.
Camper et al., "Cost per episode of care with collagenase clostridium histolyticum versus fasciectomy for Dupuytren's contracture: a real-world claims database analysis", Poster presented at the Annual Academy of Managed Care Pharmacy Nexus (AMCP Nexus), Oct. 16-19, 2017, pp. 57-64.
Casabona et al., "Microfocused Ultrasound with Visualization and Calcium Hydroxlapatite for Improving Skin Laxity and Cellulite Appearance," PRS Global Open, 2017, pp. 1-8.
Center for Drug Evaluation and Research; Application No. 206330rig1s000; Other Review(S); PMR/PMC Development Template; https://www.accessdata.fda.gov/drugsatfda_docs/nda/2015/206333Orig1s000OtherR.pdf; Last Updated Apr. 27, 2015, pp. 1-140.
Center Watch Staff, "BioSpecifics Technologies announces positive data from phase lib cellulite study" Nov. 21, 2016, pp. 1-2.
Chen et al., "Clinicopathological Study on Submucosal Injection of Collagenase in the Treatment of Submucous Fibrosis in the Oral Cavity", The Kaohsiung Journal of Medical Sciences, 1986, vol. 2, No. 3, pp. 212-219.
Citation of Prior Art and Statements Under 35 U.S.C. 301 dated Dec. 23, 2019, pp. 1-17.
Collagenase—Worthington Enzyme Manual, available at http://www.worthington-biochem.com/cls/default.html; downloaded from internet on Dec. 1, 2020; pp. 1-4.
Collagenase P, From Clostridium histolyticum; Roche Diagnostics GmbH, Jul. 2005, 2 pages.
Coons et al., "Recommendations on Evidence Needed to Support Measurement Equivalence between Electronic and Paper-Based Patient-Reported Outcome (PRO) Measures", ISPOR ePRO Good Research Practices Task Force Report, Value in Health, 2009, vol. 12, pp. 419-429.
Costas et al., "A randomized phase 2A, double-blind, placebo-controlled, dose-ranging study to evaluate the safety and effectiveness of collagenase clostridium histolyticum (cch) in the treatment of Dupuytren disease nodules", Podium presented at the 71st Annual Meeting of the American Society for Surgery of the Hand (ASSH), 2016, pp. 1-2.
Costas et al., "Efficacy and safety of collagenase clostridium histolyticum for Dupuytren disease nodules: a randomized controlled trial", BMC Musculoskelet Disord, 2017, vol. 18, No. 374, pp. 1-10.
Court Decision dated Aug. 11, 2017 in Korean Appeal Suit case for Korean Patent Application No. 10-2011-7006197.
Cuggino et al., "Synthesis, characterization and slow drug delivery of hydrogels based in N-acryloyl-tris-(hydroxymethyl) aminomethane and N-isopropyl acrylamide", Reactive & Functional Polymers, 2011, vol. 71, pp. 440-446.
Dargatz et al., "The Heterodimeric Protease Clostripain from Clostridium Histolyticum is Encoded by a Single Gene," Mol. Gen. Genet., 1993, vol. 240, pp. 140-145.
Declaration of Dr. Dagum dated Sep. 4, 2017: "Curriculum Vitae of Alexander B. Dagum, M.D", pp. 1-19.
Declaration of Dr. Michael Mclane: "Auxilium Drug Shipment Request Form for Domestic Studies regarding Protocol No. AUX-CC-830," 2011.
Declaration of Dr. Susan G. Emeigh Hart: "Assignment Recorded with the USPTO on Aug. 17, 2016 at Reel 039466 Frame 0337".
Declaration of inventor Benjamin Del Tito, Jr. dated Feb. 7, 2010 and filed in U.S. Appl. No. 11/699,302.
Demidyuk et al., "Structural Organization of Precursors of Thermolysin-like Proteinases," Protein J., 2008, vol. 27, pp. 343-354.
Denkler et al., "Evidence-Based Medicine: Options for Dupuytren's Contracture: Incise, Excise, and Dissolve," Plastic and Reconstructive Surgery, 2016, vol. 139, No. 1, pp. 240e-255e.
Dhaneshwar et al., "Dextran: A promising macromolecular drug carrier," Indian Journal of Pharmaceutical Sciences, 2006, pp. 705-714.
Difeo and BBL Manual, "Manual of Microbiological Culture Media", 2003, pp. 458-460.
Dimarcantonio, "Multiple Collagenase Injections Effective, Safe for Treating Frozen Shoulder", OrthoSuper Site, 2008, Retrieved from the Internet: http://www.orthosupersite.com/view.aspx?rid=16738#jump, retrieved on Nov. 8, 2011, pp. 1-2.
Divino et al., "Total cost of care associated with collagenase clostridium histolyticum versus fasciectomy for the treatment of Dupuytren's contracture: a retrospective cohort analysis", American Association for Hand Surgery (AAHS) Annual Meeting, 2018, pp. 1-3.
Draelos, "The disease of cellulite", Journal of Cosmetic Dermatology, vol. 4, Issue 4, First Published Dec. 5, 2005, pp. 1-3.
Ducka et al., "A Universal Strategy for High-Yield Production of Soluble and Functional Clostridial Collagenases in E. coli," Appl. Microbiol Biotechnol, 2009, vol. 83, pp. 1055-1065.
Eckhard et al., "Structural Basis for Activity Regulation and Substrate Preference of Clostridial Collagenases G, H, and T", J. Biol. Chem., vol. 288, No. 28, Jul. 12, 2013, pp. 20184-20194.
Edkins et al., "Assessment of Potential Cross-Reactivity of Human Endogenous Matrix Metalloproteinases With Collagenase Clostridium Histolyticum Antibodies In Human Sera Obtained From Patients With Dupuytren's Contracture", Clinical And Vaccine Immunology, 2012, vol. 19, No. 4, pp. 562-569.
EMBL, "Protein Expression and Purification Core Facility", Cloning Choice of Expression Systems, 2002, pp. 1-4.
Eoanna Bauer, "Endo Announces Positive Data from Phase 2b Study of Collagenase Clostridium Histolyticum (CCH) in Patients with Cellulite", Endo International plc, 2016, pp. 1-4.
Eschbach et al., "Improved Erythrocyte Lysis Assay in Microtitre Plates for Sensitive Detection and Efficient Measurements of Hemolytic Compounds from Ichthyotoxic Algae", Journal of Applied Toxicology, 2001, vol. 21, pp. 513-519.
Evans, "The lanthanide-enhanced affinity chromatography of clostridial collagenase", Biochem J, 1985, vol. 225, No. 2, pp. 553-556.
Food and Drug Administration, "Guidance for Industry on Patient-Reported Outcome Measures: Use in Medical Product Development to Support Labeling Claims", Availability Use in Medical Product Development to Support Labeling claims, Federal Register, 2009, vol. 74, No. 235, pp. 65132-65133.
Friedman et al. "Degradation of porcine dermal connective tissue by collagenase and hyaluronidase," British Journal of Dermatology, 1986, vol. 115, pp. 403-408.
Friedmann et al., "Cellulite: a Review with a Focus on Subcision," Clin Cosmet Investig Dermatol, 2017, vol. 10, pp. 17-23.
Frigerio et al., "Model Building of a Thermolysin-Like Protease by Mutagenesis," Protein Eng., 1997, vol. 10, No. 3, pp. 223-230.
Galardy et al., "Inhibition of Collagenase from Clostridium histolyticum by Phosphoric and Phosphonic Amides," Biochemistry, 1983, vol. 22, pp. 4556-4561.
Gaston et al., "The Efficacy and Safety of Concurrent Collagenase Clostridium Histolyticum Injections for 2 Dupuytren Contractures in the Same Hand: a Prospective, Multicenter study", J Hand Surg Am. 2015, vol. 40, No. 10, pp. 1963-1971.
Gelbard et al., "Collagenase Versus Placebo in the Treatment of Peyronie's Disease: A Double-Blind Study", The Journal of Urology, 1993, vol. 1489, pp. 56-58.
Gelbard et al., "The Use of Collagenase in the Treatment of Peyronie's Disease", The Journal of Urology, 1985, vol. 134, pp. 280-283.
GenBank Database accession No. D29981, "Clostridium Histolyticum colH gene for collagenase, complete cds", Retreived from https://www.ncbi.nlm.nih.gov/nuccore/D29981, 2003, pp. 1-2.
GenBank Database accession No. D87125, "Ascaris Suum mRNA for ASABF-delta, complete cds", Retrieved from https://www.ncbi.nlm.nih.gov/nuccore/D87125, 2003, pp. 1-1.
GenBank Database accession No. D87215, "Clostridium histolyticum orfluG, colG, mscL, orf2dG, orf3dG genes, complete cds", Retrieved from https://www.ncbi.nlm.nih.gov/nuccore/D87215, 2007, pp. 1-3.
GenBank Database accession No. X63673, "C.histolyticum closl gene for alpha-clostripain", Retrieved from https://www.ncbi.nlm.nih.gov/nuccore/X63673, 1993, pp. 1-2.

(56) References Cited

OTHER PUBLICATIONS

GenBank Under Accession No. CAA54291; Retrieved from: https://www.ncbi.nlm.nih.gov/protein/CAA54291; Retrieved on: May 19, 2023.
Gill et al., "Does needle size matter?," Journal of Diabetes Science and Technology, vol. 1 (5), Sep. 2007, pp. 725-729.
Gilpin et al., "Injectable collagenase clostridium histolyticum: a new nonsurgical treatment for Dupuytren's disease,"J Hand Surg Am, 2010, vol. 35, No. 12, pp. 2027-2038.
Giudicelli et al. "Influence of trypsin on lipolysis in human fat cells comparison with rat adipocytes," Biochimica et Biophysica Acta, 1976, vol. 450, Issue 3, pp. 358-366.
Goldman et al., "Cellulite: A New Treatment Approach Combining Subdermal Nd: YAG Laser Lipolysis and Autologous Fat Transplantation", Aesthetic Surg J., 2008, vol. 28, pp. 656-662.
Goldstein et al., "Baseline severity of Peyronie's Disease Symptoms Predicts Improved Female Partner Burden Scores After Treatment with Collagenase Clostridium Histolyticum", Moderated poster presented at the Sexual Medicine Society of North America (SMSNA): Oct. 26-29, 2017: San Antonio, TX, pp. 1-6.
Goldstein et al., "Baseline severity of Peyronie's Disease Symptoms Predicts Improved Female Partner Burden Scores After Treatment with Collagenase Clostridium Histolyticum", Podium presented at the American Urological Association (AUA), May 21, 2018, pp. 1-10.
Goldstein et al., "Impact of Collagenase Clostridium Histolyticum Treatment of Men With Peyronie's Disease on Improvement of Female Partner Sexual Function", AUA, 2018, p. 1.
Goldstein et al., "Changes in the Effects of Peyronie's Disease After Treatment With Collagenase Clostridium histolyticum: Male Patients and Their Female Partners", Sex Med., 2017, vol. 5, No. 2, pp. e124-e130.
Gordon et al., "Clostridium septicum Alpha Toxin is Proteolytically Activated by Furin," Infection and Immunity, 1997, vol. 65, No. 10, pp. 4130-4134.
Green et al., "Cellfina Observations: Pearls and Pitfalls," Seminars in Cutaneous Medicine and Surgery, 2015, vol. 34, pp. 144-146.
Hale et al., "Long-term safety and analgesic efficacy of buprenorphine buccal film in patients with moderate-to-severe chronic pain requiring around-the-clock opioids", J Pain Res., 2017, vol. 10, pp. 233-240.
Hannafin, et al., "Adhesive capsulitis, A treatment approach", Clinical Orthopaedics and Related Research, 2000, No. 372, pp. 95-109.
Harmon "Is Cellulite Forever?" Scientific American, Monday May 4, 2009, 56, pp. 1-4.
Hatheway, "Toxigenic Clostridia," Clinical Microbiology Reviews, 1990, pp. 66-98.
Hay et al., "Surgical findings in the treatment of Dupuytren's disease after initial treatment with clostridial collagenase (Xiaflex)," J Hand Surg Eur, 2014, vol. 39, No. 5, pp. 463-465.
Health News, "Goodbye, Cellulite Thighs", WebMD, 2006, pp. 1-2.
Hellstrom et al., "Safety Profile of Collagenase Clostridium Histolyticum Stratified by Degree of Penile Curvature in Patients With Peyronie Disease", Urology, Aug. 2017, vol. 106, pp. 237.e9-237.e14.
Hesse et al., "Recombinant enzymes for islet isolation: purification of a collagenase from clostridium histolyticum and cloning/expression of the gene," Transplantation Proceedings, 1995, vol. 27, No. 6, pp. 3287-3289.
Heuck et al., "Conformational Changes That Effect Oligomerization and Initiate Pore Formation are Triggered Throughout Perfringolysin O Upon Binding to Cholesterol," J. Biol. Chem., 2007, vol. 282, No. 31, pp. 22629-22637.
Hexsel et al., "A validated photonumeric cellulite severity scale", JEADV, 2009, vol. 23, pp. 523-528.
Staby et al., "Comparison of Chromatographic Ion-Exchange Resins. II. More Strong Anion-Exchange Resins," Journal of Chromatography A, 2001, vol. 908, pp. 149-161.
Staley, "Auxilium Pharmaceuticals Announces First Patients Dosed in Xiaflex Phase lb Cellulite Study;" Jan. 26, 2012; 1 page; downloaded from: https://www.benzinga.com/news/12/01/2291202/auxilium-pharmaceuticals-announces-first-patients-dosed-in-xiaflex-hase-ib-cellu.
Steinbrink et al., "Substrate Specificity of Beta-Collagenase from Clostridium histolyticum," The Journal of Biological Chemistry, 1985, vol. 260, pp. 2771-2776.
Stewart, "Uterine fibroids", The Lancet, 2001, vol. 357, pp. 293-298.
Strömberg et al., "Comparison of Treatment Outcome After Collagenase and Needle Fasciotomy for Dupuytren Contracture: A Randomized, Single-Blinded, Clinical Trial With a 1-Year Follow-Up", J Hand Surg Am., 2016, vol. 41, No. 9, pp. 873-880.
Strömberg et al., "Percutaneous Needle Fasciotomy Versus Collagenase Treatment for Dupuytren Contracture, A Randomized Controlled Trial with a Two-Year Follow-up", J Bone Joint Surg Am. 2018, vol. 100, pp. 1079-1086.
Successful Phase II Results Lead to Phase III Approval—Dupuytren's Disease, Internet Citation, retrieved Aug. 20, 2010, pp. 1-2 (2001).
Sugasawara et al., "Purification and Characterization of Three Forms of Collagenase from Clostridium histolytium," Entrez Pubmed abstract, 1984, vol. 23, pp. 5175-5181.
surgerynews.net, "Is this the End of Cellulite? Some Doctors Say, Fat Chance", 2005, pp. 1-3.
Takahashi et al., "New Culture Conditions for Clostridium histolyticum Leading to Production of Collagenase of High Specific Activity," J. Appl. Bact., 1972, vol. 35, pp. 647-657.
Takahashi, et al., "Elastolytic Activities of Clostridium histolyticum," Biochem. Biophys Res. Commun., 1970, vol. 39, No. 6, pp. 1058-1064.
Tay et al., "Comparison between Collagenase Injection and Partial Fasciectomy in the Treatment of Dupuytren's Contracture," Hand Surg. 2015, vol. 20, No. 3, pp. 386-390.
Taylor et al., "Putting the Moose on the Table: Understanding the Molecular Biology of Uterine Fibroids and Development of Non-invasion Treatment," XP055257658, 2012, pp. 1-64.
Taylor et al., "Recent scientific advances in leiomyoma (uterine fibroids) research facilitates better understanding and management," F1000Research, XP055257667, 2015, pp. 1-11.
Taylor et al., "Temperature-responsive biocompatibie copolymers incorporating hyperbranched polyglycerols for adjustable functionality", Journal of Functional Biomaterials 2011, vol. 2, pp. 173-194.
Taylor et al., "Treatment for Uterine Fibroids: Searching for Effective Drug Therapies," Drug Discovery Today Therapeutic Strategies, 2012, vol. 9, No. 1, pp. e41-e49, 2012.
TeensHealth, "Cellulite," TeensHealth.org, May 2009, pp. 1-2.
Thomas et al., "The Emerging Role of Clostridium histolyticum Collagenase in the Treatment of Dupuytren Disease", Ther Clin Risk Manag., 2010, vol. 6, pp. 557-572.
Thorne et al., "Dynamic Reciprocity Between Cells and Their Microenvironment in Reproduction," Biology of Reproduction, 2014, vol. 92, No. 1, Article 25, pp. 1-10.
Tonkin, "Classification of Congenital Anomalies of the Hand and Upper Limb", J Hand Surg Am., 2015, vol. 40, No. 2, pp. 415-416.
Vos-Scheperkeuter et al., "Histochemical Analysis of the Role of Class I and Class II Clostridium Istochemical Analysis of the Role Histolyticum Collagenase in the Degradation of Rat Pancreatic Extracellular Matrix for Islet Isolation", Cell Transplantation, 1997, vol. 6, pp. 403-412.
Wanner et al., "An Evidence-Based Assessment of Treatments for Cellulite", J. Drugs Dermatol., 2008, vol. 7, No. 4, pp. 341-345.
Waters et al., "Collagenase Enzymatic Fasciotomy for Dupuytren Contracture in Patients on Chronic Immunosuppression", Am J Orthop (Belle Mead NJ), 2015, vol. 44, No. 11, pp. 518-521.
Welton et al., "Collagenase Production by Achromobacter lophagus," Biochimica et Biophysica Acta (BBA)—Enzymology, 1975, vol. 384, pp. 228-234.
Wetmore et al., "The Efficiency of Processing and Secretion of the Thermolysin-like Neutral Protease from Bacillus cereus Does Not Require the Whole Prosequence, But Does Depend on the Nature of the Amino Acid Sequence in the Region of the Cleavage Site", Mol. Microbiol., 1994, vol. 12, No. 5, pp. 747-759.

(56) References Cited

OTHER PUBLICATIONS

Why Choose Recombinant Enzymes New England Bio Labs, retrieved at https://international.neb.com/tools-and-resources/selection-charts/why-choose-recombinant-enzymes, retrieved on Mar. 2, 2022, pp. 1-7.

Wikipedia.org "Cellulite," http://en.wikipedia.org/wiki/cellulite, 2012, pp. 1-5.

Wolters et al., "Different Roles of Class I and Class II Clostridium Histolyticum Collagenase In Rat Pancreatic Islet solation", Diabetes, 1995, vol. 44, pp. 227-233.

Xiaflex, "collagenase clostridium histolyticum", Prescribing Information, Malvern, PA: Endo Pharmaceuticals Inc., Revised Nov. 2019, pp. 1-43.

Yoshihara et al., "Cloning and Nucleotide Sequence Analysis of the colH Gene from Clostridium histolyticum Encoding a Collagenase and a Gelatinase", Journal of Bacteriology, 1994, vol. 176, No. 21, pp. 6489-6496.

Young et al., "Efficacy and safety of collagenase clostridium histolyticum for the treatment of edematous fibrosclerotic panniculopathy (cellulite)", Podium presented at the American Society of Plastic Surgeons Aesthetica 2017 Super Symposium, Mar. 2-4, 2017, pp. 1-4.

Zhou et al., "Collagenase Clostridium Histolyticum versus Limited Fasciectomy for Dupuytren's Contracture", Plast Reconstr Surg, 2015, vol. 136, No. 1, pp. 87-97.

"Basic Biochemistry Experiment, Department of Biology, Beijing Normal University, Higher Education Press", pp. 38-39, Feb. 1984.

BD Bionutrients Technical Manual: Advanced Processing, 3rd edition, Oct. 2006.

Kagedal et al.; "Chemical, physical and chromatographic properties of Superdex 75 prep grade and Superdex 200 prep grade gel filtration media;" Journal of Chromatography; vol. 537, 1991, pp. 17-32.

Liberase Research Grade Purified Enzyme Blends, Reference material A10, Roche Diagnostics GmbH, Aug. 2013, Version 06, pp. 1-18.

Protein Purification Handbook, Amersham Biosciences; 2001, 1-98.

Rhodes et al., "Determination of Protein Purity," Methods in Enzymology, vol. 463, 2009, pp. 677-689.

Sigma-Aldrich, "Product Information on Collagenase, High Purity", dated Sep. 13, 2018, pp. 1-6.

\* cited by examiner

```
                        10        20        30        40        50
                         |         |         |         |         |
C. septicum α S75954 ──

FIG. 2: Blood Agar Plating of *C. septicum* Arrows Indicate Beta Hemolytic Activity

```
                           10        20        30        40        50
                            |         |         |         |         |
Thermolysin ———→  001  MKMKKKLASFGLAAGLAAQV-FLPYNALASTEKVTWNQQKQTPQFTSGDL  SEQ ID NO: 9
                            || | |: || : :::: ::  :  :|  ::::: :   :: :: :  :: ||
CLH_2576 ———→     001  MK-K-KFLSFIIISAISLNISSHTVGA-KQVKEIKPPKDKESISVLKTDL  SEQ ID NO: 10

050  LKVNGTSPEELVTQYVEK-NENKFKFHENAKDTLQLKEKKNDNLGFTFBR
                            |::: : ::   : | |   :: :| : |   | ::: :|::|   |   :|
                  048  EKTKNIKSNNKEGDDVTKVVESALKEEGNLGD-FKVDNKETDVKGKKHLR

099  FQQTYRGIPVFGAVVTSHV-KDGTLTALSGTLIPNLDTKGSLKSGKKLSE
                            |:  |||::|: |  |: ||| : :::|   : :        |:|:  ::::
                  097  SQHFIDGIPVYGSQVIHTNKDGQVYSVNGK-VDKQPKAQSFKNRVRIKD

148  KQARDIAEKDLVANVTKEVPEYEQSRDTEFVSTVNGDEASLAYVVNLNFL
                            :|  ||| :|  :: |:  :| ::::  ::   |||:   : |:|:::
                  146  DKAIKIAEDSLGKEIKKN-KNY-HSESKLYLYKVNGDLQPV-YLVKISST

198  TPEPGNWLYIIDAVDGKILNKFNQLDAAKPGDVKSITGTSTVGVGRGVLG
                            || : | ::::| :|||::|  |  : :    :: :  |::: |   : :|:
                  193  EPEASFVHHFVSAENGKIVDKYNAL-SCQATHAQ-VRGVNSSGEHK-ILN

248  DQKNINTTYSTYYYLQDNTR-GNG-IFTYDAKYRT-TLPGSLUADADHQF
                            : : |   :  |:| |:|| :||  |:|:||:  :   :|||:::   :  |
                  240  GHFE-N----G-RYFLADSTRPSNGYILTYDANNQEYGFPGSLFSNLTGIF

295  FASYDAPAVDAHYYAGVTYDYYKNVHNRLSYDGNNAAIRSSVHYSQGYNN
                            :: :  :||||:    :|||||||  ||  |:|:::|  ||||  :::  ||
                  285  DSDRQKAGVDAHHNL-TQVYDYYKNVLNRDSFDGKGASIISSVHVGHNLNN

345  AFUNGSQHVYGDGDGQTFIPLSGGIDVVAHELTHAVTDYTAGLIYQNESG
                            |||||  |::::|||||  ||   |:   ::::|||:|||||:  |||| |:   :||
                  335  AFWNGRQILFGDGDGVTFSNLAKCLEVTAHEFTHAVTQSTAGLEYRFQSG

395  AINEAISDIFGTLVEFYANKNPDUEIGEDVYTPGISGDSLRSHSDPAKYG
                            |:|||:|||:|    :   :::   |||||||||:|||:::||:||||:|   |
                  385  ALNEAFSDILG---IAVHSDPN-DUEIGEDIYTPHVAGDALRSHSNPRLYR

445  DPDHYSKR-Y-TGTQDNGGVHINSGIINKAAYLISQGGTHYGVSVVGIGR
                            :|||::   |   ::|:||||  ||||  ||||||:     |  :          |  |:
                  432  QPDHUKDYLYSDYSKDKGGVHYNSGIPNKAAYLN---G-K---E-V--GK

493  DKLGKIFYRALTQYLTPTSNFSQLRAAAVQSATDLYGSTSQE-VASVKQA
                            |:::||:::|||| |:| :| :| |:|:|| ||:| :|:|       :;|:
                  472  DSHAKIYYHALVNYLTPQSTFEDARNAVVSSAIDLHGENSREHKLAIKSW

542  FD-AVG---VK
                            |  :||   |:
                  522  ADVGVGEEAVR
```

FIG. 3

```
                                10        20        30        40        50
                                |         |         |         |         |
ThermolysinPro ──────▷ 001  STEHVTWNQQFQTPQFISGDLLKVNGTSPEELVYQYVERNENKFKFHENA SEQ ID NO: 11
                            :  :   : :    ::  :    :| |:   ::  |  : | |   : :| : |
ClH_2576 Pro ──────▷ 001  KPPKDKESISVLKTDLEKTKNIKSNNKEGDD-VTKVV-K--SALKEEGNL SEQ ID NO: 12

051  KDTLQLKEKKNDNLGFTFKRFQQTYKGIPVFGAVVTSHV-KDGTLTALSG
                           |  ::: :|::|   |    :|  |:   |:|||:|: |  |: ||| : ::|
                      047  GD--FKVDNKETDUKGKKHLRSQHFIDGIPVYGSQVIIHTNKDGQVYSVNG

100  TLIPNLDTKGSLKSGKKLSEKQARDIAEKDLVANVTKEVPEYEQGKDTEF
                             : :      |:|:   ::::  :|  |||  :|   ::  |:  :|  ::::    :
                      096  K-VDKQPKAQSFKNRVRIKDDKAIKIAEDSLGKEIKKN-KNY-HSESKLY
                                                    * *                      * * * *
                      150  VVYVNGDEASLAYVVNLNFLTPEPGNWLYIIDAVDGKILNKFNQLDAAKP
                           :  ||||   :  :|:::    || :  |   ::::|  :|||::|:|  | : :
                      143  LYKVNGDLQPV-YLVKISSTEPEASFWHMFVSAENGKIVDKYNAL-SCQA
                           * * * * *
                      200  GDVKS
                           : :
                      191  THAQ-
```

FIG. 4

```
                                 10        20        30        40        50
                                  |         |         |         |         |
Thermolysin Mature    → 001  ITCTSTVGVGRGVLGDQKNINTTYSTYYYLQDNTR-GNG-IFTYDAKYRT SEQ ID NO: 13
                              : |::: |  : :|: : : |   :  |:| |:|| :|| |:|||: :
CLH_2576 Mature       → 001  VRGVNSSGEHK-ILNGHFE-N---G-RYFLADSTRPSNGYILTYDANNQES SEQ ID NO: 14

049  -TLPGSLUADADNQFFASYDAPAVDAHYYAGVTYDYYKNVHNRLSYDGNN
                              :||||::: : | :: : :|||: :||||||| || |:||::
                        045  YGFPGSLFSMLTGIFDSDRQKAGVDAHHNLTQVYDYYKNVLNRDSPDGKG

**   *
                        098  AAIRSSVHYSQGYNNAFHNGSQMVYGDGDGQTFIPLSGGIDVVAHELTHA
                              |:| |||| ::: |||||| |:::||||| || |: ::|||||||
                        095  ASIISSVHVGNNLNNAFHNGRQILFGDGDGVTFSNLAKCLEVTAHEFTHA
                                                *
                        148  VTDYTAGLIYQNESGAINEAISDIFGTLVEFYANKNPDUEIGEDVYTPGI
                              ||: |||| |: :|||:|||:|||:| :  ::: | |||||||:||::
                        145  VTQSTAGLEYRFQSGALNEAPSDILG--IAVHSDPN-DUEIGEDIYTPNV

198  SGDSLRSHSDPAKYGDPDHYSKR-Y-TGTQDNGGVHINSGIINKAAYLIS
                              :|:|||||:| | :|||:: | :::|||| |||| |||||||:
                        192  AGDALRSHSNPRLYRQPDHHKDYLYUDYSHDKGGVHYNSGIPNKAAYLH-

246  QGGTHYGVSVVGIGRDKLGKIFYRALTQYLTPTSNFSQLRAAAVQSATDL
                              | :   | |:|::|:|||:|:|:::|||| |:| : | |:|:|| ||
                        241  ---G-K----E-V--GKDSHAKIYYHALUNYLTPQSTFEDARNAVVSSAIDL

296  YGSTSQE-VASVKQAFD-AVG----VK
                              :| :|:|  ::|: | :|| |:
                        282  HGENSKEHKLAIKSWADVGVGEEAVR
```

FIG. 5

```
                              10        20        30        40    *   50
                              |         |         |         |        |
Perfringolysin ──▶  001  N-I--R-FKK-TK--LIASI-AMALC--L---FS-QPVISFSKDI-TD--  SEQ ID NO: 15
                         | |  : ::: ::  ||: |  :::    |    |::  |:  : :  ||
CLH_192D ──────▶  001    NKITKKGLRSLSRLHLITHITGLTYNYHLGSSFNGNRVVLANPNTKTDNL SEQ ID NO: 16

034    -KNQS---IDSGISSLSYNRNEVLASNGDKIESFVPKEGKKTGNKFIVVER
                         ||:|   ||  | :|||:  ::|: ||:|:|:|||  |  :::::||  |::|
                  051    IKNNSDEIDEKIYGLSYDPYKILSYNGEKVENFVPAECSENSGKFTVIKR

081    QKRSLTTSPVDISIIDSVNDRTYPGALQLADRAFVENRPTILKVKRKPIN
                         :|:::: |  :|||||:||:||||||||:||:::  ::||:|::  :||||:
                  101    EKRNISDSTTDISIHDSINDRTYPGAIQLANRDLIENKPNLISCERKPIT

131    INIDLPGLKGENSIK-VDDPTYGKVSGAIDELVSKWNEKYSSTHTLPART
                         |::|||||  ||::   |  |  |::|||:||::||  |:: ||  ||  :|:|:|
                  151    ISVDLPGH-GEDGKKVVNSPTYSSVNSAINYLLDTWNSKYSSKYTIPTRN

180    QYSESHVYSKSQISSALWVNAKVLENSLGVDFNAVAMNEKKVHILAYKQI
                         :||:||||||||:|: :|  |  |||  :||::||:|:::  ::|||:||||||
                  200    NYSDTHVYSKSQLSTHFGCNFKTLSKSLNIDFDSIFKGEKKAHILSYKQI

230    FYTVSADLPKNPSDLFDDSVTFNDLKQKGVSNEAPPLHVSNVAYGRTIYV
                         ||||||:| |: |||||  |||  ::|  |||:|: ||  ||  :|||||||||||:||
                  250    FYTVSVDGPNRPSDLFGYSVTSKSLALKGVNNDNPPAYVSNVAYGRTVYV

280    KLETTSSSKDVQAAFKALIKNTDIKNSQQYKDIYENSSFTAVVLGGDAQE
                         |||||||:::  |:||||||||::|  ||::::  ::|||  ::||||||:|||||  |||
                  300    KLETTSKSSKVKAAFKALVENQDISSNAEYKDIINQSSFTATVLGGGAQK

330    HNKVVTKDFDEIRKVIKDNATFSTKNPAYPISYTSVFLKDNSVARVHNKT
                         ||||||||||| ||::||:|::::|  :|||:|||||||:||||||::|:||::|:|
                  350    HNKVVTKDFDVIRNIIKNNSVYSPQNPGYPISYTSTFLKDNKIATVNNRT

380    DYIETTSTEYSKGKINLDRSGAYVAQFEVAWDEVSYDKEGNEVLTHKTWD
                         :||||:|||::|||  ||||||:||||||||||:||||||||||:|||::  ||:|:
                  400    EYIETTATEYDSGKIHLDHSGVYVAQFEVTWDEVSYDKQGNEIIEHKSWS

430    GNYQDKTAHYSTVIPLEANARNIRIKARECTGLAUEBWRDVISEYDVPLT
                         || :|:|||::|  : |::|||||  |||:|||||||||||| |:  ::||:
                  450    GNNSDRTAHFNTELYLKGNARNISIKAKECTGLAUEBWRTVVLAKNLPLV
                                                     ****

480    RNINVSIUGTTLYPGSSITYN
                         ::  ::||:|||||||  |: :
                  500    KERKLSIUGTTLYPRYSHEEK
```

FIG. 6

```
                    SEQ ID NO: 17          10         20         30         40    *    50
Clostripain Locus X63673 ────→ 001   MLRRKVSTLLHTALITTSFLNSKPVYANPVTKSKDNNLKEVQQVTSKSNK
                    (SEQ ID NO: 18)       |||||||||||||||||||||||||||||||||||||||||||| ||||
CLH_1861  ────→        001   MLRRKVSTLLHTALITTSFLNSKPVYANPVTKSKDNNLKEVQQVISKSNK 051   NKNQKVTIMYYCDADNNLEGSLLNDIEEHKTGYKDSPNLNLIALVDRSPR
                                     |||||||||||||||||||||||||||||||||||||||||||||||||
                               051   NKNQKVTIMYYCDADNNLEGSLLNDIEEHKTGYKDSPNLNLIALVDRSPR

*
                               101   YSSDEKVLGEDFSDTRLYKIEHNKANRLDGKNEFPEISTTSKYEANHGDP
                                     ||||||||||||||||||||| |||||||||||||||||||||||||||
                               101   YSSDEKVLGEDFSDTRLYKIELNKANRLDGKNEFPEISTTSKYEANHGDP

151   EVLKKFIDYCKSNYEADKYVLIHANHGGGAREKSNPRLNRAICWDDSNLD
                                     |||||||||||||||||||||||||||||||||||||||||||||||||
                               151   EVLKKFIDYCKSNYEADKYVLIHANHGGGAREKSNPRLNRAICWDDSNLD

201   KNGEADCLYHGEISDHLTEKQSVDLLAFDACLMGTAEVAYQYRPGNGGFS
                                     |||||||||||||||||||||||||||||||||||||||||||||||||
                               201   KNGEADCLYHGEISDHLTEKQSVDLLAFDACLMGTAEVAYQYRPGNGGFS

251   ADTLVASSPVVWGPGFKYDKIFDRIKAGGGTNWEDDLTLGGKEQNFDPAT
                                     |||||||||||||||||||||||||||||||||||||||||||||||||
                               251   ADTLVASSPVVWGPGFKYDKIFDRIKAGGGTNWEDDLTLGGKEQNFDPAT

301   ITNEQLGALFVEEQRDSTHANGRYDQHLSFYDLKKAESVKRAIDNLAVNL
                                     |||||||||||||||||||||||||||||||||||||||||||||||||
                               301   ITNEQLGALFVEEQRDSTHANGRYDQHLSFYDLKKAESVKRAIDNLAVNL

351   SNENKKSEIEKLRGSGIHTDLHHYFDEYSEGEWVEYPYFDVYDLCEKINK
                                     |||||||||||||||||||||||||||||||||||||||||||||||||
                               351   SNENKKSEIEKLRGSGIHTDLHHYFDEYSEGEWVEYPYFDVYDLCEKINK

*
                               401   SINFSSKTKDLASNAHNKLNEMIVYSFGDPSNNFKEGKNGLSIFLPNGDK
                                     ||||||||||||||||||||||||||||||||||||||||||| |||||
                               401   SINFSSKTKDLASNAHNKLNEMIVYSFGDPSNNFKEGKNGLSTFLPNGDK

451   KYSTYYTSTKIPHWTHQSWYNSIDTVKYGLNPYGKLSWCKDGQDPEINKV
                                     |||||||||||||||||||||||||||||||||||||||||||||||||
                               451   KYSTYYTSTKIPHWTHQSWYNSIDTVKYGLNPYGKLSWCKDGQDPEINKV

501   GNWFELLDSWFDKTNDVTGGVNHYQW
                                     ||||||||||||||||||||||||||
                               501   GNWFELLDSWFDKTNDVTGGVNHYQW
```

FIG. 8

```
          Identities = 1113/1118 (100%), Positives = 1118/1118 (100%)
SEQ ID NO:3 0001  MKKNILKILMDSYSKESKIQTVRRVTSVSLLAAYLTMNTSSLVLAKPIENTNDTSIKNVEKLRN
                  ||||||||||||||||||||||||||||||||:|||||||||||||||||||||||||||||||
SEQ ID NO:19 0001 MKKNILKILMDSYSKESKIQTVRRVTSVSLLAVYLTMNTSSLVLAKPIENTNDTSIKNVEKLRN
                                                                    N-terminus of mature protein Ile 111

0065  APNEENSKKVEDSKNDKVEHVENIEEAKVEQVAPEVKSKSTLRSASIANTNSEKYDFEYLNGLS
                  ||||||||||||||||||||:|||||||||||||||||||||||||||||||||||||||||||
            0065  APNEENSKKVEDSKNDKVEHVKNIEEAKVEQVAPEVKSKSTLRSASIANTNSEKYDFEYLNGLS

0129  YTELTNLIKNIKWNQINGLFNYSTGSQKFFGDKNRVQAIINALQESGRTYTANDNKGIETFTEV
                  |||||||||||||||||||||||||||||||||||||||||||||||||||||||||||||||
            0129  YTELTNLIKNIKWNQINGLFNYSTGSQKFFGDKNRVQAIINALQESGRTYTANDNKGIETFTEV

0193  LRAGFYLGYYNDGLSYLNDRNFQDKCIPAMIAIQKNPNFKLGTAVQDEVITSLGKLIGNASANA
                  |||||||||||||||||||||||||||||||||:|||||||||||||||||||||||||||||
            0193  LRAGFYLGYYNDGLSYLNDRNFQDKCIPAMIAIQKNPNFKLGTAVQDEVITSLGKLIGNASANA

0257  EVVMNCVPVLKQFRENLNQYAPDYVKGTAVNELIKGIEFDFSGAAYEKDVKTMPWYGKIDPFIN
                  |||||||||||||||||||||||||||||||||||||||||||||||||||||||||||||||
            0257  EVVNNCVPVLKQFRENLNQYAPDYVKGTAVNELIKGIEFDFSGAAYEKDVKTMPWYGKIDPFIN

0321  ELKALGLYGNITSATEWASDVGIYYLSKFGLYSTNRNDIVQSLEKAVDNYKYGKIAFVAMERIT
                  |||||||||||||||||||||||||||||||||||||||||||||||||||||||||||||||
            0321  ELKALGLYGNITSATEWASDVGIYYLSKFGLYSTNRNDIVQSLEKAVDNYKYGKIAFVAMERIT

0385  WDYDGIGSNGKKVDHDKFLDDAEKHYLPKTYTFDNGTFIIRAGEKVSEEKIKRLYWASREVKSQ
                  ||||||||||||||||||||||||||||||||||||||||||:|||||||||||||||||||||
            0385  WDYDGIGSNGKKVDHDKFLDDAEKHYLPKTYTFDNGTFIIRAGDKVSEEKIKRLYWASREVKSQ

0449  FHRVVGNDKALEVGNADDVLTMKIFNSPEEYKFNTNINGVSTDNGGLYIEPRGTFYTYERTPQQ
                  |||||||||||||||||||||||||||||||||||||||||||||||||||||||||||||||
            0449  FHRVVGNDKALEVGNADDVLTMKIFNSPEEYKFNTNINGVSTDNGGLYIEPRGTFYTYERTPQQ

0513  SIFSLEELFRHEYTHYLQARYLVDGLWGQGPFYEKNRLTWFDEGTAEFFAGSTRTSGVLPRKSI
                  |||||||||||||||||||||||||||||||||||||||||||||||||||||||||||||||
            0513  SIFSLEELFRHEYTHYLQARYLVDGLWGQGPFYEKNRLTWFDEGTAEFFAGSTRTSGVLPRKSI
```

FIG. 9A

```
0577  LGYLAKDKVDHRYSLKKTLNSGYDDSDWMFYNYGFAVAHYLYEKDMPTFIKMNKAILNTDVKSY
      ||||||||||||||||||||||||||||||||||||||||||||||||||||||||||||||||
0577  LGYLAKDKVDHRYSLKKTLNSGYDDSDWMFYNYGFAVAHYLYEKDMPTFIKMNKAILNTDVKSY

0641  DEIIKKLSDDANKNTEYQNHIQELADKYQGAGIPLVSDDYLKDHGYKKASEVYSEISKAASLTN
      ||||||||||||||||||||||||||||||||||||||||||||||||||||||||||||||||
0641  DEIIKKLSDDANKNTEYQNHIQELADKYQGAGIPLVSDDYLKDHGYKKASEVYSEISKAASLTN

0705  TSVTAEKSQYFNTFTLRGTYTGETSKGEFKDWDEMSKKLDGTLESLAKNSWSGYKTLTAYFTNY
      ||||||||||||||||||||||||||||||||||||||||||||||||||||||||||||||||
0705  TSVTAEKSQYFNTFTLRGTYTGETSKGEFKDWDEMSKKLDGTLESLAKNSWSGYKTLTAYFTNY

0769  RVTSDNKVQYDVVFHGVLTDNADISNNKAPIAKVTGPSTGAVGRNIEFSGKDSKDEDGKIVSYD
      ||||||||||||||||||||||||||||||||||||||||||||||||||||||||||||||||
0769  RVTSDNKVQYDVVFHGVLTDNADISNNKAPIAKVTGPSTGAVGRNIEFSGKDSKDEDGKIVSYD

0833  WDFGDGATSRGKNSVHAYKKTGTYNVTLKVTDDKGATATESFTIEIKNEDTTTPITKEMEPNDD
      |||||||||||||||||||||:||||||||||||||||||||||||||||||||||||||||||
0833  WDFGDGATSRGKNSVHAYKKAGTYNVTLKVTDDKGATATESFTIEIKNEDTTTPITKEMEPNDD

0897  IKEANGPIVEGVTVKGDLNGSDDADTFYFDVKEDGDVTIELPYSGSSNFTWLVYKEGDDQNHIA
      ||||||||||||||||||||||||||||||||||||||||||||||||||||||||||||||||
0897  IKEANGPIVEGVTVKGDLNGSDDADTFYFDVKEDGDVTIELPYSGSSNFTWLVYKEGDDQNHIA

0961  SGIDKNNSKVGTFKATKGRHYVFIYKHDSASNISYSLNIKGLGNEKLKEKENNDSSDKATVIPN
      |||||||||||||:||||||||||||||||||||||||||||||||||||||||||||||||||
0961  SGIDKNNSKVGTFKSTKGRHYVFIYKHDSASNISYSLNIKGLGNEKLKEKENNDSSDKATVIPN

1025  FNTTMQGSLLGDDSRDYYSFEVKEEGEVNIELDKKDEFGVTWTLHPESNINDRITYGQVDGNKV
      ||||||||||||||||||||||||||||||||||||||||||||||||||||||||||||||||
1025  FNTTMQGSLLGDDSRDYYSFEVKEEGEVNIELDKKDEFGVTWTLHPESNINDRITYGQVDGNKV

1089  SNKVKLRPGKYYLLVYKYSGSGNYELRVNK
      ||||||||||||||||||||||||||||||
1089  SNKVKLRPGKYYLLVYKYSGSGNYELRVNK
```

FIG. 9B (SEQ ID NO: 20) colH → 0001 RKRKCLSKRLHLAITHATIFTVNSTLPIYAAVDKNNATAAVQNESKRYTVSYLKTLNYYDLVDL Identities = 1013/1021 (99%), Positives = 1021/1021 (100%)

|||||||||||||||||||||||||||||||||||||||||||||||||||||||||||||||

SEQ ID NO: 4 → 0001 HKRKCLSKRLHLAITHATIFTVNSTLPIYAAVDKNNATAAVQNESKRYTVSYLKTLNYYDLVDL

Alignment Assessment

0065 LVKTEIENLPDLFQYSSDAKEFYGNKTRHSFIHDEIGRRAPQYTEIDHRGIPTLVEVVRAGFYL
|||||||||||||||||||||||||||||||||||||||||||||||||||||||||||||||
0065 LVKTEIENLPDLFQYSSDAKEFYGNKTRHSFIHDEIGRRAPQYTEIDHRGIPTLVEVVRAGFYL

Collagenase II

0129 GFHNKELNEINKRSFKERVIPSILAIQKNPNFKLGTEVQDKIVSATGLLAGNETAPPEVVRRIFT

Green shading - N-termini of mature protein A31 in AVDK stretch

|||||||||||||||||||||||||||||||||||||||||||||||||||||||||||||||
0129 GFHNKELNEINKRSFKERVIPSILAIQKNPNFKLGTEVQDKIVSATGLLAGNETAPPEVVRNFT

Green shading – single aa amino acid differences in entire molecule

0193 PILQDCIHNSDRYALDDLKSKALFNVLAAPTYDITEYLRATKERPENTPWYGKIDGFINELKRL
|||||||||||||||||||||||||||||||||||||||||||||||||||||||||||||||
0193 PIEQDCIKNHDRYALDDLKSKALFNVLAAPTYDITEYLRATKEKPENTPWYGKIDGFINELKKL

0257 ALYGKINDNNSWIIDNGIYHIAPLGKLHSNHKIGIETLTEVHKVTPYLSHQHLQSADQIKRHYD
|||||||||||||||||||||||||||||||||||||||||||||||||||||||||||||||
0257 ALYGKINDNNSWIIDNGIYHIAPLGKLHSNHKIGIETLTEVHKIYPYLSHQHLQSADQIERHYD

0321 SKDAEGNKIPLDKFKKEGKERYCPKTYTFDDGKVIIKAGARVEEEKVKRLYBASKEVNSQFFRV
|||||||||||||||||||||||||||||||||||||||||||||||||||||||||||||||
0321 SKDAEGNKIPLDKFKKEGKEKYCPKTYTFDDGKVIIKAGARVEEEKVKRLYBASKEVNSQFFRV

0385 YCIDKPLEEGNPDDILTKVIYNSPEEYKLNSVLYGYDTNNGGHYIEPEGIFFTYEREAQESTYT
|||||||||||||||||||||||||||||||||||||||||||||||||||||||||||||||
0385 YGIDKPLEEGNPDDILTKVIYNSPEEYKLNSVLYGYDTNNGGRYIEPEGTFFTYERKAEESTYT

0449 LEELFRHEYTHYLQGRYAVPGQWGRTKLYDNDRLTWYEEGGAELFAGSTRTSGILPRKSIVSNI
|||||||||||||||||||||||||||||||||||||||||||||||||||||||||||||||
0449 LEELFRHEYTHYLQGRYAVPGQWGRTKLYDNDRLTWYEEGGAELFAGSTRTSGILPRKSIVSNI

0513 HNTTRHNRYKLSDTVHSKYGASFEFYNYACHFNDYHYNKDHGILNKLNDLAKNDVDGYDNYIR
|||||||||||||||||||||||||||||||||||||||||||||||||||||||||||||||
0513 HNTTRNNRYKLSDTVHSKYGASFEFYNYACHFNDYHYNKDHGILNKLNDLAKNDVDGYDNYIR

FIG. 10A

```
colH        ----------->  0577  DLSSNYALNDKYQDHMQERIDNYENLTVPFVADDYLVRHAYKNPNEIYSEISEVAKLKDAKSEV
                                ||||| |||||||||||||||||||||||||||||||||||||||||||||||||||||||
SEQ ID NO:4 ----------->  0577  DLSSNHALNDKYQDHMQERIDNYENLTVPFVADDYLVRHAYKNPNEIYSEISEVAKLKDAKSEV 0641  KKSQYFSTFTLRGSYTGGASKGKLEDQKAHNKFIDDSLKKLDTYSWSGYKTLTAYFTNYKVDSS
                                ||||||| |||||||||||||||||| ||||||||||||||||||||||||||||||||||||
                          0641  KKSQYFSTFTLRGSYTGGASKGKLEDQKAHNKFIDDSLKKLDTYSWSGYKTLTAYFTNYKVDSS 0705  NRVTYDVVFHGYLPNEGDSKNSLPYGKINGTYKGTEKEKIKFSSEGSFDPDGKIVSYEBDFGDG
                                ||||||||||||||||||||||||||||||||||||||||||||||||||||||||||||||||
                          0705  NRVTYDVVFHGYLPNEGDSKNSLPYGKINGTYKGTEKEKIKFSSEGSFDPDGKIVSYEWDFGDG 0769  NKSNEENPEHSYDKVGTYTVKLKVTDDKGESSVSTTTAEIKDLSENKLPVIYHBVPKSGALNQK
                                ||||||||||||||||||||||||||||||||||||||||||||||||||||||||||||||||
                          0769  NKSNEENPEHSYDKVGTYTVKLKVTDDKGESSVSTTTAEIKDLSENKLPVIYHBVPKSGALNQK 0833  VVFYGKGTYDPDGSIAGYQWDFGDGSDFSSEQNPSHVYTKKGEYTVTLRVHDSSGQRSEKTHKI
                                ||||||||||| |||||||||||||||||||||||||||||||||||||||||||||||||||
                          0833  VVFYGKGTYDPDGSIAGYQWDFGDGSDFSSEQNPSHVYTKKGEYTVTLRVHDSSGQRSEKTHKI 0897  KITDPVYPIGTEKEPNNSKETASGPIVPGIPVSGTIENTSDQDYFYFDVITPGEVKIDINKLGY
                                ||||||||||||||||||||||||||||||||||||||||||||||||||||||||||||||||
                          0897  KITDPVYPIGTEKEPNNSKETASGPIVPGIPVSGTIENTSDQDYFYFDVITPGEVKIDINKLGY 0961  GGATWVYDENNNAVSYATDDGQNLSGKFKADKFGRYYIHLYMFNGSYHPYRINIEGSVGR
                                ||||||||||||||||||||||||||||||||||||||||||||||||||||||||||||
                          0961  GGATWVYDENNNAVSYATDDGQNLSGKFKADKPGRYYIHLYMFNGSYHPYRINIEGSVGR
```

FIG. 10B

SEQ ID NO: 1

ATGAAAAAAAATATTTTAAAGATTCTTATGGATAGTTATTCTAAAGAATC
TAAAATTCAAACTGTACGTAGGGTTACGAGTGTATCACTTTTAGCGGCAT
ATCTTACTATGAATACTTCAAGTTTAGTTTTAGCAAAACCAATAGAAAAT
ACTAATGATACTAGTATAAAAAATGTGGAGAAATTAAGAAATGCTCCAAA
TGAAGAGAATAGTAAAAAGGTAGAAGATAGTAAAAATGATAAGGTAGAAC
ATGTGGAAAATATAGAAGAGGCAAAAGTTGAGCAAGTTGCACCCGAAGTA
AAATCTAAATCAACTTTAAGAAGTGCTTCTATAGCGAATACTAATTCTGA
GAAATATGATTTTGAGTATTTAAATGGTTTGAGCTATACTGAACTTACAA
ATTTAATTAAAAATATAAAGTGGAATCAAATTAATGGTTTATTTAATTAT
AGTACAGGTTCTCAAAAGTTCTTTGGAGATAAAAATCGTGTACAAGCTAT
AATTAATGCTTTACAAGAAAGTGGAAGAACTTACACTGCAAATGATATGA
AGGGTATAGAAACTTTCACTGAGGTTTTAAGAGCTGGTTTTTATTTAGGG
TACTATAATGATGGTTTATCTTATTTAAATGATAGAAACTTCCAAGATAA
ATGTATACCTGCAATGATTGCAATTCAAAAAAATCCTAACTTTAAGCTAG
GAACTGCAGTTCAAGATGAAGTTATAACTTCTTTAGGAAAACTAATAGGA
AATGCTTCTGCTAATGCTGAAGTAGTTAATAATTGTGTACCAGTTCTAAA
ACAATTTAGAGAAACTTAAATCAATATGCTCCTGATTACGTTAAAGGAA
CAGCTGTAAATGAATTAATTAAAGGTATTGAATTCGATTTTCTGGTGCT
GCATATGAAAAGATGTTAAGACAATGCCTTGGTATGGAAAAATTGATCC
ATTTATAAATGAACTTAAGGCCTTAGGTCTATATGGAAATATAACAAGTG
CAACTGAGTGGGCATCTGATGTTGGAATATACTATTTAAGTAAATTCGGT
CTTTACTCAACTAACCGAAATGACATAGTACAGTCACTTGAAAAGGCTGT
AGATATGTATAAGTATGGTAAAATAGCCTTTGTAGCAATGGAGAGAATAA
CTTGGGATTATGATGGGATTGGTTCTAATGGTAAAAAGGTGGATCACGAT
AAGTTCTTAGATGATGCTGAAAAACATTATCTGCCAAAGACATATACTTT
TGATAATGGAACCTTTATTATAAGAGCAGGGGAGAAGGTATCCGAAGAAA
AAATAAAAAGGCTATATTGGGCATCAAGAGAAGTGAAGTCTCAATTCCAT
AGAGTAGTTGGCAATGATAAAGCTTTAGAGGTGGGAAATGCCGATGATGT
TTTAACTATGAAAATATTTAATAGCCCAGAAGAATATAAATTTAATACCA
ATATAAATGGTGTAAGCACTGATAATGGTGGTCTATATATAGAACCAAGA
GGGACTTTCTACACTTATGAGAGAACACCTCAACAAAGTATATTTAGTCT
TGAAGAATTGTTTAGACATGAATATACTCACTATTTACAAGCGAGATATC
TTGTAGATGGTTTATGGGGACAAGGTCCATTTTATGAAAAAAATAGATTA
ACTTGGTTTGATGAAGGTACAGCTGAATTCTTTGCAGGATCTACCCGTAC
ATCTGGTGTTTTACCAAGAAAATCAATATTAGGATATTTGGCTAAGGATA
AAGTAGATCATAGATACTCATTAAAGAAGACTCTTAATTCAGGGTATGAT
GACAGTGATTGGATGTTCTATAATTATGGATTTGCAGTTGCACATTATCT
ATATGAAAAGATATGCCTACATTTATTAAGATGAATAAAGCTATATTGA
ATACAGATGTGAAATCTTATGATGAAATAATAAAAAAATTAAGTGATGAT
GCAAATAAAAATACAGAATATCAAAACCATATTCAAGAGTTAGCAGATAA
ATATCAAGGAGCAGGCATACCTCTAGTATCAGATGATTACTTAAAAGATC
ATGGATATAAGAAAGCATCTGAAGTATATTCTGAAATTTCAAAAGCTGCT
TCTCTTACAAACACTAGTGTAACAGCAGAAAAATCTCAATATTTTAACAC
ATTCACTTTAAGAGGAACTTATACAGGTGAAACTTCTAAAGGTGAATTTA
AAGATTGGGATGAAATGAGTAAAAAATTAGATGGAACTTTGGAGTCCCTT
GCTAAAAATTCTTGGAGTGGATACAAAACTTTAACAGCATACTTTACGAA
TTATAGAGTTACAAGCGATAATAAAGTTCAATATGATGTAGTTTTCCATG
GGGTTTTAACAGATAATGCGGATATTAGTAACAATAAGGCTCCAATAGCA
AAGGTAACTGGACCAAGCACTGGTGCTGTAGGAAGAAATATTGAATTTAG
TGGAAAAGATAGTAAAGATGAAGATGGTAAAATAGTATCATATGATTGGG

FIG. 11A

```
ATTTTGGCGATGGTGCAACTAGTAGAGGCAAAAATTCAGTACATGCTTAC
AAAAAAACAGGAACATATAATGTTACATTAAAAGTAACTGACGATAAGGG
TGCAACAGCTACAGAAAGCTTTACTATAGAAATAAAGAACGAAGATACAA
CAACACCTATAACTAAAGAAATGGAACCTAATGATGATATAAAAGAGGCT
AATGGTCCAATAGTTGAAGGTGTTACTGTAAAAGGTGATTTAAATGGTTC
TGATGATGCTGATACCTTCTATTTTGATGTAAAAGAAGATGGTGATGTTA
CAATTGAACTTCCTTATTCAGGGTCATCTAATTTCACATGGTTAGTTTAT
AAAGAGGGAGACGATCAAAACCATATTGCAAGTGGTATAGATAAGAATAA
CTCAAAAGTTGGAACATTTAAAGCTACAAAAGGAAGACATTATGTGTTTA
TATATAAACACGATTCTGCTTCAAATATATCCTATTCTTTAAACATAAAA
GGATTAGGTAACGAGAAATTGAAGGAAAAAGAAAATAATGATTCTTCTGA
TAAAGCTACAGTTATACCAAATTTCAATACCACTATGCAAGGTTCACTTT
TAGGTGATGATTCAAGAGATTATTATTCTTTTGAGGTTAAGGAAGAAGGC
GAAGTTAATATAGAACTAGATAAAAGGATGAATTTGGTGTAACATGGAC
ACTACATCCAGAGTCAAATATTAATGACAGAATAACTTACGGACAAGTTG
ATGGTAATAAGGTATCTAATAAAGTTAAATTAAGACCAGGAAAATATTAT
CTACTTGTTTATAAATACTCAGGATCAGGAAACTATGAGTTAAGGGTAAA
TAAATAA
```

FIG. 11 B

SEQ ID NO: 2

ATGAAAAGGAAATGTTTATCTAAAAGGCTTATGTTAGCTATAACAATGGC
TACAATATTTACAGTGAACAGTACATTACCAATTTATGCAGCTGTAGATA
AAAATAATGCAACAGCAGCTGTACAAAATGAAAGTAAGAGGTATACAGTA
TCATATTTAAAGACTTTAAATTATTATGACTTAGTAGATTTGCTTGTTAA
GACTGAAATTGAGAATTTACCAGACCTTTTTCAGTATAGTTCAGATGCAA
AAGAGTTCTATGGAAATAAAACTCGTATGAGCTTTATCATGGATGAAATT
GGTAGAAGGGCACCACAGTATACAGAGATAGATCATAAAGGTATTCCTAC
TTTAGTAGAAGTTGTAAGAGCTGGATTTTACTTAGGATTCCATAACAAGG
AATTGAATGAAATAAATAAGAGGTCTTTTAAAGAAAGGGTAATACCTTCT
ATATTGGCAATTCAAAAAATCCTAATTTTAAACTAGGTACTGAAGTTCA
AGATAAAATAGTATCTGCAACAGGACTTTTAGCTGGTAATGAAACAGCGC
CTCCAGAAGTTGTAAATAATTTTACACCAATAATTCAAGACTGTATCAAA
AATATGGACAGATATGCTCTTGATGATTTAAAGTCAAAAGCATTATTTAA
TGTTTTAGCTGCACCTACCTATGATATAACTGAGTATTTAAGAGCTACTA
AAGAAAAACCAGAAAACACTCCTTGGTATGGTAAAATAGATGGGTTTATA
AATGAACTTAAAAAGTTAGCTCTTTATGGAAAAATAAATGATAATAACTC
TTGGATAATAGATAATGGTATATATCATATAGCACCTTTAGGGAAGTTAC
ATAGCAATAATAAAATAGGAATAGAAACTTTAACAGAGGTTATGAAGATA
TATCCTTATTTAAGTATGCAACATTTACAATCAGCAGATCAAATTGAGCG
TCATTATGATTCAAAAGATGCTGAAGGAAATAAAATACCTTTAGATAAGT
TTAAAAAGGAAGGAAAAGAGAAATACTGTCCAAAAACTTATACATTTGAT
GATGGAAAAGTAATAATAAAAGCTGGTGCTAGGGTAGAAGAAGAAAAAGT
TAAAAGACTATACTGGGCATCAAAGGAAGTTAACTCTCAATTCTTTAGGG
TATATGGAATAGACAAACCATTAGAAGAAGGTAATCCAGATGATATATTA
ACAATGGTTATCTACAACAGTCCTGAAGAATATAAACTTAATAGTGTTCT
ATACGGATATGATACTAATAATGGTGGTATGTATATAGAGCCAGATGGAA
CTTTCTTCACATATGAAAGAAAGCTGAAGAAAGCACATACACATTAGAA
GAATTATTTAGACATGAATATACACACTATTTACAAGGAAGATATGCAGT
TCCTGGTCAATGGGGAAGAACAAAACTTTATGACAATGATAGATTAACTT
GGTATGAAGAAGGTGGAGCAGAATTATTTGCAGGTTCTACTAGAACTTCT
GGAATATTACCAAGAAAGAGTATAGTATCAAATATTCATAATACAACAAG
AAATAATAGATATAAGCTTTCAGACACTGTACATTCTAAATATGGTGCTA
GTTTTGAATTCTATAATTATGCATGTATGTTTATGGATTATATGTATAAT
AAAGATATGGGTATATTAAATAAACTAAATGATCTTGCAAAAAATAATGA
TGTTGATGGATATGATAATTATATTAGAGATTTAAGTTCTAATCATGCTT
TAAATGATAAATATCAAGATCATATGCAGGAGCGCATAGATAATTATGAA
AATTTAACAGTGCCTTTTGTAGCTGATGATTATTTAGTAAGACATGCTTA
TAAGAACCCTAATGAAATTTATTCTGAAATATCTGAAGTAGCAAAATTAA
AGGATGCTAAGAGTGAAGTTAAGAAATCACAATATTTTAGTACCTTTACT
TTGAGAGGTAGTTACACAGGTGGAGCATCTAAGGGGAAATTAGAAGATCA
AAAAGCAATGAATAAGTTTATAGATGATTCACTTAAGAAATTAGATACGT
ATTCTTGGAGTGGGTATAAAACTTTAACTGCTTATTTCACTAATTATAAA
GTTGACTCTTCAAATAGAGTTACTTATGATGTAGTATTCCACGGATATTT
ACCAAACGAAGGTGATTCCAAAAATTCATTACCTTATGGCAAGATCAATG
GAACTTACAAGGGAACAGAGAAAGAAAAAATCAAATTCTCTAGTGAAGGC
TCTTTCGATCCAGATGGTAAAATAGTTTCTTATGAATGGGATTTCGGAGA
TGGTAATAAGAGTAATGAGGAAAATCCAGAGCATTCATATGACAAGGTAG
GAACTTATACAGTGAAATTAAAAGTTACTGATGACAAGGGAGAATCTTCA
GTATCTACTACTACTGCAGAAATAAAGGATCTTTCAGAAAATAAACTTCC
AGTTATATATATGCATGTACCTAAATCCGGAGCCTTAAATCAAAAGTTG
TTTTCTATGGAAAAGGAACATATGACCCAGATGGATCTATCGCAGGATAT
CAATGGGACTTTGGTGATGGAAGTGATTTTAGCAGTGAACAAAACCCAAG

FIG. 12A

```
CCATGTATATACTAAAAAAGGTGAATATACTGTAACATTAAGAGTAATGG
ACAGTAGTGGACAAATGAGTGAAAAAACTATGAAGATTAAGATTACAGAT
CCGGTATATCCAATAGGCACTGAAAAAGAACCAAATAACAGTAAAGAAAC
TGCAAGTGGTCCAATAGTACCAGGTATACCTGTTAGTGGAACCATAGAAA
ATACAAGTGATCAAGATTATTTCTATTTTGATGTTATAACACCAGGAGAA
GTAAAAATAGATATAAATAAATTAGGGTACGGAGGAGCTACTTGGGTAGT
ATATGATGAAAATAATAATGCAGTATCTTATGCCACTGATGATGGGCAAA
ATTTAAGTGGAAAGTTTAAGGCAGATAAACCAGGTAGATATTACATCCAT
CTTTACATGTTTAATGGTAGTTATATGCCATATAGAATTAATATAGAAGG
TTCAGTAGGAAGATAA
```

FIG. 12B

CLH_2835 and CLH_2834 (SEQ ID NO: 8)

MLKKSFFKKAICASLVVLQCLILVSPAQTLASTDLPTKGKTSIELFNYEDHMAHCLGF
GWCFGTASKEIGEDFEFKRAEEEGKTVYYLSARYNQNDPYAKGYYRAHDRLVMKV
SNARFFIDHDSLTLGKAKVISLDPLASSTLQVVNKSNSEAKTSLSFGYETTESTSKTDH
VKFGEKIGIKSSFNVKVPFIGEKSIETNLEFNSEQGWSNTKTNSVTTKHTISHTTTTPA
KSRKKVRLNVLNKKSDIPYEGKIYMEYDIEFFGFLRYTGNARKDHPTDRPSVSVKFG
GKNNMSAVDHIIDLYKHKDINGYSEWDWNWIEENFYDRFSEYSSNVASQYFGGIISG
VFTNVGGTDVKVEEGRERPLKNTSSTEQNVEVQNFKSSKSKEFRVGSLTYTTPNGEQ
TIYPEDVSSLNANNNEN

FIG. 13A

CLH_2834&2835 (SEQ ID NO: 21)

ATGTTAAAAAAATCTTTTTTTAAAAAGGCAATTTGCGCATCTTTGGTGGT
GCTACAATGTTTGATATTAGTGTCACCAGCTCAAACATTGGCATCAACAG
ATTTGCCGACAAAAGGAAAAACTTCAATTGAACTATTTAACTATGAAGAT
CATTAAATGGCTCATTGTTTGGGATTTGGATGGTGCTTCGGTACAGCATC
AAAAGAAATAGGGGAAGATTTTGAATTTAAAAGAGCAGAAGAAGAAGGAA
AAACAGTATATTATTTATCAGCTAGATACAATCAAAATGATCCTTACGCT
AAAGGCTATTATCGCGCGCATGATAGGCTTGTTATGAAGGTTAGTAATGC
TAGGTTTTTTATCGATCATGATTCATTAACTTTAGGAAAAGCTAAAGTTA
TAAGTCTAGATCCACTGGCATCATCAACTCTTCAAGTAGTAAATAAAAGT
AATTCTGAAGCTAAAACATCATTATCTTTTGGATATGAAACTACTGAAAG
TACTTCCAAAACGGATCACGTTAAATTCGGAGAAAAAATTGGAATTAAGT
CATCATTTAATGTTAAAGTTCCATTTATAGGAGAAAAATCAATTGAAACA
AATCTTGAATTCAATTCAGAGCAGGGTTGGTCCAATACGAAAACTAACTC
TGTAACTACTAAACATACAATTTCTCATACAACAACAACACCTGCAAAGA
GCAGGAAAAAGGTACGATTAAATGTTCTTAATAAAAAGTCCGACATACCA
TATGAGGGTAAGATATATATGGAATATGATATAGAGTTTTTTGGTTTTTT
AAGATATACTGGAAATGCGCGTAAAGATCATCCTACAGATAGACCTAGTG
TATCAGTAAAATTTGGGGGAAAAAATAATATGAGTGCGGTAGATCATATT
ATAGATTTGTACAAGCATAAAGATATTAATGGCTATTCAGAATGGGATTG
GAATTGGATTGAAGAAAATTTTTATGATAGATTTAGTGAATATTCATCTA
ATGTTGCTAGTCAATATTTTGGGGGCATTATTTCTGGTGTATTTACTAAT
GTGGGTGGAACAGATGTAAAAGTTGAAGAAGGTAGAGAAAGGCCACTTAA
AAATACAAGTTCTACAGAACAAAATGTCGAAGTACAGAATTTTAAAAGCT
CTAAATCTAAAGAGTTTAGAGTGGGTAGTTTAACATATACTACTCCTAAT
GGAGAACAGACCATATATCCTGAAGACGTATCATCTCTTAACGCTAACAA
CAATGAGAATTAA

FIG. 13B

CLH_2576 (SEQ ID NO: 10)

MKKKFLSFIIISAISLNISSMTVGAKQVKEIKPPKDKESISVLKTDLEKTKNIKSNNKEG
DDVTKVVKSALKEEGNLGDFKVDNKETDVKGKKHLRSQMFIDGIPVYGSQVIIHTN
KDGQVYSVNGKVDKQPKAQSFKNRVRIKDDKAIKIAEDSLGKEIKKNKNYHSESKL
YLYKVNGDLQPVYLVKISSTEPEASFWHMFVSAENGKIVDKYNALSCQATHAQVRG
VNSSGEHKILNGMFENGRYFLADSTRPSNGYILTYDANNQEYGFPGSLFSNLTGIFDS
DRQKAGVDAHHNLTQVYDYYKNVLNRDSFDGKGASIISSVHVGNNLNNAFWNGRQ
ILFGDGDGVTFSNLAKCLEVTAHEFTHAVTQSTAGLEYRFQSGALNEAFSDILGIAVH
SDPNDWEIGEDIYTPNVAGDALRSMSNPRLYRQPDHMKDYLYWDYSMDKGGVHY
NSGIPNKAAYLMGKEVGKDSMAKIYYHALVNYLTPQSTFEDARNAVVSSAIDLHGE
NSKEHKLAIKSWADVGVGEEAVR

FIG. 14A

CLH_2576 (SEQ ID NO: 22)

ATGAAAAAAAAATTTTTAAGTTTTATTATTATTTCTGCCATATCACTTAA
CATTTCTTCTATGACTGTGGGGGCAAAGCAAGTGAAAGAAATCAAACCTC
CAAAAGATAAAGAATCTATTTCTGTATTAAAAACAGATTTAGAAAAAACC
AAGAATATAAAATCTAATAATAAGGAGGGGGATGATGTAACAAAAGTAGT
TAAGAGTGCTTTAAAAGAAGAAGGCAATTTAGGAGATTTTAAGGTTGATA
ATAAAGAAACTGATGTAAAAGGTAAAAAGCACTTGCGTTCACAAATGTTT
ATAGATGGTATTCCTGTATATGGTAGTCAAGTTATAATTCATACTAATAA
AGATGGACAAGTATATAGCGTAAATGGAAAAGTAGATAAACAGCCTAAAG
CTCAATCTTTTAAGAACCGTGTAAGGATTAAGGACGATAAAGCTATTAAA
ATAGCAGAAGACAGTTTAGGTAAGGAAATAAAGAAAAACAAAAATTATCA
TTCTGAAAGTAAGTTGTACCTATACAAGGTTAATGGAGATTTACAACCTG
TGTATTTGGTAAAGATATCATCTACAGAACCAGAAGCTTCATTTTGGCAT
ATGTTTGTAAGTGCTGAAAATGGAAAGATAGTTGATAAGTATAATGCTTT
ATCATGCCAAGCTACACATGCTCAAGTAAGAGGAGTTAATAGCAGTGGAG
AGCATAAAATCTTAAATGGTATGTTTGAAAATGGAAGATATTTTTTAGCA
GATTCAACAAGACCTTCAAATGGATATATATTAACATATGATGCTAATAA
CCAAGAGTATGGTTTCCCAGGTAGCTTATTTAGTAATTTAACAGGCATTT
TTGATAGTGATAGACAAAAGGCAGGAGTAGATGCTCACCATAATCTAACT
CAAGTATATGATTATTATAAAAATGTTTTAAATAGAGATAGTTTTGATGG
AAAAGGTGCTAGTATAATATCTTCTGTGCATGTAGGAAATAATTTAAATA
ATGCTTTCTGGAATGGTAGACAAATACTTTTTGGTGATGGAGACGGAGTT
ACATTTAGTAACCTAGCAAAATGTTTAGAAGTTACTGCCCATGAATTTAC
ACATGCAGTTACTCAAAGTACTGCAGGTCTAGAATATAGATTTCAATCTG
GTGCTCTAAATGAAGCTTTTTCTGATATTTTAGGTATAGCTGTTCACAGT
GATCCAAATGATTGGGAAATTGGAGAAGATATATACACTCCTAATGTAGC
AGGAGATGCTTTAAGAAGTATGTCAAATCCTAGATTATATAGACAACCAG
ACCATATGAAGGACTATTTATATTGGGATTATTCAATGGATAAAGGTGGA
GTTCATTATAATTCAGGTATTCCAAATAAAGCAGCTTATTTGATGGGAAA
AGAAGTTGGAAAAGATTCAATGGCTAAAATTTATTATCATGCTTTAGTGA
ATTATTTAACTCCTCAAAGTACATTTGAAGATGCTAGAAATGCAGTAGTA
TCATCTGCAATAGATTTACATGGTGAGAATAGTAAAGAACATAAACTTGC
TATAAAATCTTGGGCAGATGTAGGCGTTGGAGAAGAGGCAGTAAGATAA

FIG. 14B

CLH_1920 (SEQ ID NO: 16)

MKITKKGLRSLSRLMLITMITGLTYNYHLGSSFNGNRVVLANPNTKTDNLIKNNSDEI
DEKIYGLSYDPYKILSYNGEKVENFVPAECSENSGKFTVIKREKKNISDSTTDISIMDSI
NDRTYPGAIQLANRDLIENKPNLISCERKPITISVDLPGMGEDGKKVVNSPTYSSVNS
AINYLLDTWNSKYSSKYTIPTRMNYSDTMVYSKSQLSTMFGCNFKTLSKSLNIDFDSI
FKGEKKAMILSYKQIFYTVSVDGPNRPSDLFGYSVTSKSLALKGVNNDNPPAYVSNV
AYGRTVYVKLETTSKSSKVKAAFKALVENQDISSNAEYKDIINQSSFTATVLGGGAQ
KHNKVVTKDFDVIRNIIKNNSVYSPQNPGYPISYTSTFLKDNKIATVNNRTEYIETTAT
EYDSGKIMLDHSGVYVAQFEVTWDEVSYDKQGNEIIEHKSWSGNNSDRTAHFNTEL
YLKGNARNISIKAKECTGLAWEWWRTVVDAKNLPLVKERKLSIWGTTLYPRYSMEE
K

FIG. 15A

CLH_1920 (SEQ ID NO: 23)

ATGAAGATTACAAAGAAAGGCTTAAGATCATTATCACGCTTAATGTTAAT
TACTATGATAACAGGATTAACATACAATTATCACCTAGGTAGTAGCTTTA
ATGGGAATCGAGTAGTACTTGCAAATCCAAATACAAAAACAGATAATTTA
ATTAAGAATAATAGTGATGAAATAGACGAAAAGATTTATGGATTGTCTTA
TGATCCATATAAAATATTATCTTATAATGGAGAAAAGGTTGAAAACTTTG
TTCCAGCTGAATGTTCCGAGAATTCCGGAAAATTTACTGTAATAAAACGT
GAAAAGAAAAATATTTCAGATTCAACTACAGATATTTCAATAATGGATTC
AATAAATGATAGAACTTATCCTGGTGCTATACAACTAGCAAATAGGGATC
TTATAGAAAATAAGCCTAATTTAATTTCATGCGAGAGAAAACCTATTACT
ATAAGTGTTGATTTACCTGGTATGGGTGAGGATGGGAAAAAGGTTGTTAA
TTCTCCAACATACTCTTCAGTTAATTCAGCAATAAATTATTTGCTAGATA
CATGGAATTCAAAATATTCATCTAAATATACTATACCTACAAGGATGAAT
TATTCTGATACTATGGTGTATAGTAAATCACAGTTATCTACAATGTTTGG
ATGTAACTTTAAAACTTTAAGTAAATCCTTAAATATAGATTTTGATTCTA
TATTTAAAGGCGAAAAAAAGGCTATGATTCTATCATATAAACAAATTTTC
TACACAGTGAGTGTAGATGGACCTAATCGCCCATCAGATTTATTTGGTTA
CAGTGTAACTTCTAAGAGCTTAGCTTTAAAAGGAGTAAATAATGATAATC
CTCCAGCATACGTTTCCAATGTTGCATATGGTAGAACTGTTTATGTAAAA
CTAGAGACAACATCTAAGAGTTCAAAGGTTAAAGCAGCATTTAAGGCATT
AGTAGAGAATCAAGATATAAGTAGTAATGCAGAATATAAAGACATAATAA
ATCAAAGTTCATTTACAGCTACTGTTCTAGGTGGAGGAGCACAAAAACAC
AATAAAGTAGTTACTAAAGATTTCGATGTAATAAGAAATATTATTAAAAA
TAATTCAGTATATAGCCCACAAAATCCTGGATATCCTATTTCATATACAA
GTACATTTTTAAAAGACAATAAAATAGCAACTGTAAACAATAGAACAGAA
TATATAGAAACAACTGCAACAGAATACGATAGCGGCAAAATAATGCTTGA
CCATAGTGGAGTTTATGTTGCTCAATTTGAAGTAACCTGGGATGAAGTTA
GTTATGACAAACAAGGAAATGAAATAATTGAGCATAAATCTTGGTCTGGA
AACAATAGTGATAGAACAGCTCACTTTAATACAGAACTATATTTAAAAGG
AAATGCAAGAAACATTTCTATAAAAGCAAAGAATGTACAGGCCTTGCTT
GGGAATGGTGGAGAACTGTTGTAGATGCTAAAAATTTACCACTTGTAAAA
GAAAGAAAGTTATCAATATGGGGTACAACATTATATCCTAGATATTCTAT
GGAAGAGAAATAA

FIG. 15B

CLH_1861 (SEQ ID NO: 18)

MLRRKVSTLLMTALITTSFLNSKPVYANPVTKSKDNNLKEVQQVISKSNKNKNQKV
TIMYYCDADNNLEGSLLNDIEEMKTGYKDSPNLNLIALVDRSPRYSSDEKVLGEDFS
DTRLYKIELNKANRLDGKNEFPEISTTSKYEANMGDPEVLKKFIDYCKSNYEADKYV
LIMANHGGAREKSNPRLNRAICWDDSNLDKNGEADCLYMGEISDHLTEKQSVDLL
AFDACLMGTAEVAYQYRPGNGGFSADTLVASSPVVWGPGFKYDKIFDRIKAGGGTN
NEDDLTLGGKEQNFDPATITNEQLGALFVEEQRDSTHANGRYDQHLSFYDLKKAES
VKRAIDNLAVNLSNENKKSEIEKLRGSGIHTDLMHYFDEYSEGEWVEYPYFDVYDLC
EKINKSENFSSKTKDLASNAMNKLNEMIVYSFGDPSNNFKEGKNGLSTFLPNGDKKY
STYYTSTKIPHWTMQSWYNSIDTVKYGLNPYGKLSWCKDGQDPEINKVGNWFELLD
SWFDKTNDVTGGVNHYQW

FIG. 16A

CLH_1861 (SEQ ID NO: 24)

ATGttaagaagaaaagtatcaacactattaatgacagctttgataactacttcatttttaaat
tccaaacccgtatatgcaaatccagtaactaaatccaaggataataacttaaaagaagtac
aacaagttataagcaagagtaataaaaacaaaaatcaaaaagtaactattatgtactattgc
gacgcagataataacttggaaggaagtctattaaatgatatcgaggaaatgaaaacagga
tataaggatagtcctaatttaaatttaattgctcttgtagacagatccccaagatatagcagtg
acgaaaaagttttaggtgaagattttagtgatacacgtctttataagattgaactcaataagg
caaatagattagacggtaaaaatgaatttccagaataagtactactagtaaatatgaagct
aacatgggggatcctgaagttcttaaaaaatttattgattattgtaaatctaattatgaggctg
ataaatatgtgcttataatggctaatcatggtggtggtgcaagggaaaaatcaaatccaag
attaaatagagcaatttgctgggatgatagtaaccttgataaaaatggtgaagcagactgc
ctttatatgggtgaaatttcagatcatttaacagaaaaacaatcagttgatttacttgccttga
tgcatgcctatgggaactgcagaagtagcgtatcagtatagaccaggtaatggaggattt
tctgccgatactttagttgcttcaagcccagtagtttggggtcctggattcaaatatgataag
attttcgataggataaaagctggtggaggaactaataatgaggatgatttaactttaggtgg
taaagaacaaaactttgatcctgcaaccattaccaatgagcaattaggtgcattatttgtaga
agagcaaagagactcaacacatgccaatggtcgctatgatcaacacttaagctttatgatt
taaagaaagctgaatcagtaaaaagagccatagataatttagctgttaatctaagtaatgaa
aacaaaaaatctgaaattgaaaaattaagaggaagtggaattcatacagatttaatgcatta
cttcgatgaatattctgaaggagaatgggttgaatatccttattttgacgtgtatgatttatgtg
aaaaaataaataaaagtgaaaattttagtagtaaaactaaagatttagcttcaaatgctatga
ataaattaaatgaaatgatagtttattcttttggagaccctagtaataattttaaagaaggaaa
aaatggattgagtacattcttacctaatggagataaaaaatattcaacttattatacatcaacc
aagatacctcattggactatgcaaagttggtataattcaatagatacagttaaatatggattg
aatccttacggaaaattaagttggtgtaaagatggacaagatcctgaaataaataaagttg
gaaattggtttgaacttctagattcttggtttgataaaactaatgatgtaactggaggagttaa
tcattaccaatggTAA SEQ ID NO: 3 (colG)

MKKNILKILMDSYSKESKIQTVRRVTSVSLLAAYLTMNTSSLVLAKPIENTNDTSIKN
VEKLRNAPNEENSKKVEDSKNDKVEHVENIEEAKVEQVAPEVKSKSTLRSASIANTN
SEKYDFEYLNGLSYTELTNLIKNIKWNQINGLFNYSTGSQKFFGDKNRVQAIINALQE
SGRTYTANDMKGIETFTEVLRAGFYLGYYNDGLSYLNDRNFQDKCIPAMIAIQKNPN
FKLGTAVQDEVITSLGKLIGNASANAEVVNNCVPVLKQFRENLNQYAPDYVKGTAV
NELIKGIEFDFSGAAYEKDVKTMPWYGKIDPFINELKALGLYGNITSATEWASDVGIY
YLSKFGLYSTNRNDIVQSLEKAVDMYKYGKIAFVAMERITWDYDGIGSNGKKVDHD
KFLDDAEKHYLPKTYTFDNGTFIIRAGEKVSEEKIKRLYWASREVKSQFHRVVGNDK
ALEVGNADDVLTMKIFNSPEEYKFNTNINGVSTDNGGLYIEPRGTFYTYERTPQQSIF
SLEELFRHEYTHYLQARYLVDGLWGQGPFYEKNRLTWFDEGTAEFFAGSTRTSGVL
PRKSILGYLAKDKVDHRYSLKKTLNSGYDDSDWMFYNYGFAVAHYLYEKDMPTFI
KMNKAILNTDVKSYDEIIKKLSDDANKNTEYQNHIQELADKYQGAGIPLVSDDYLKD
HGYKKASEVYSEISKAASLTNTSVTAEKSQYFNTFTLRGTYTGETSKGEFKDWDEMS
KKLDGTLESLAKNSWSGYKTLTAYFTNYRVTSDNKVQYDVVFHGVLTDNADISNN
KAPIAKVTGPSTGAVGRNIEFSGKDSKDEDGKIVSYDWDFGDGATSRGKNSVHAYK
KTGTYNVTLKVTDDKGATATESFTIEIKNEDTTTPITKEMEPNDDIKEANGPIVEGVT
VKGDLNGSDDADTFYFDVKEDGDVTIELPYSGSSNFTWLVYKEGDDQNHIASGIDK
NNSKVGTFKATKGRHYVFIYKHDSASNISYSLNIKGLGNEKLKEKENNDSSDKATVIP
NFNTTMQGSLLGDDSRDYYSFEVKEEGEVNIELDKKDEFGVTWTLHPESNINDRITY
GQVDGNKVSNKVKLRPGKYYLLVYKYSGSGNYELRVNK

FIG. 17A

SEQ ID NO: 5

IANTNSEKYDFEYLNGLSYTELTNLIKNIKWNQINGLFNYSTGSQKFFGDKNRVQAII
NALQESGRTYTANDMKGIETFTEVLRAGFYLGYYNDGLSYLNDRNFQDKCIPAMIAI
QKNPNFKLGTAVQDEVITSLGKLIGNASANAEVVNNCVPVLKQFRENLNQYAPDYV
KGTAVNELIKGIEFDFSGAAYEKDVKTMPWYGKIDPFINELKALGLYGNITSATEWA
SDVGIYYLSKFGLYSTNRNDIVQSLEKAVDMYKYGKIAFVAMERITWDYDGIGSNG
KKVDHDKFLDDAEKHYLPKTYTFDNGTFIIRAGEKVSEEKIKRLYWASREVKSQFHR
VVGNDKALEVGNADDVLTMKIFNSPEEYKFNTNINGVSTDNGGLYIEPRGTFYTYER
TPQQSIFSLEELFRHEYTHYLQARYLVDGLWGQGPFYEKNRLTWFDEGTAEFFAGST
RTSGVLPRKSILGYLAKDKVDHRYSLKKTLNSGYDDSDWMFYNYGFAVAHYLYEK
DMPTFIKMNKAILNTDVKSYDEIIKKLSDDANKNTEYQNHIQELADKYQGAGIPLVS
DDYLKDHGYKKASEVYSEISKAASLTNTSVTAEKSQYFNTFTLRGTYTGETSKGEFK
DWDEMSKKLDGTLESLAKNSWSGYKTLTAYFTNYRVTSDNKVQYDVVFHGVLTD
NADISNNKAPIAKVTGPSTGAVGRNIEFSGKDSKDEDGKIVSYDWDFGDGATSRGKN
SVHAYKKTGTYNVTLKVTDDKGATATESFTIEIKNEDTTTPITKEMEPNDDIKEANGP
IVEGVTVKGDLNGSDDADTFYFDVKEDGDVTIELPYSGSSNFTWLVYKEGDDQNHI
ASGIDKNNSKVGTFKATKGRHYVFIYKHDSASNISYSLNIKGLGNEKLKEKENNDSS
DKATVIPNFNTTMQGSLLGDDSRDYYSFEVKEEGEVNIELDKKDEFGVTWTLHPESN
INDRITYGQVDGNKVSNKVKLRPGKYYLLVYKYSGSGNYELRVNK

FIG. 17B

SEQ ID NO: 4 (colH)

MKRKCLSKRLMLAITMATIFTVNSTLPIYAAVDKNNATAAVQNESKRYTVSYLKTL
NYYDLVDLLVKTEIENLPDLFQYSSDAKEFYGNKTRMSFIMDEIGRRAPQYTEIDHK
GIPTLVEVVRAGFYLGFHNKELNEINKRSFKERVIPSILAIQKNPNFKLGTEVQDKIVS
ATGLLAGNETAPPEVVNNFTPHQDCIKNMDRYALDDLKSKALFNVLAAPTYDITEYL
RATKEKPENTPWYGKIDGFINELKKLALYGKINDNNSWIIDNGIYHIAPLGKLHSNNK
IGIETLTEVMKIYPYLSMQHLQSADQIERHYDSKDAEGNKIPLDKFKKEGKEKYCPKT
YTFDDGKVIIKAGARVEEEKVKRLYWASKEVNSQFFRVYGIDKPLEEGNPDDILTMV
IYNSPEEYKLNSVLYGYDTNNGGMYIEPDGTFFTYERKAEESTYTLEELFRHEYTHYL
QGRYAVPGQWGRTKLYDNDRLTWYEEGGAELFAGSTRTSGILPRKSIVSNIHNTTRN
NRYKLSDTVHSKYGASFEFYNYACMFMDYMYNKDMGILNKLNDLAKNNDVDGYD
NYIRDLSSNHALNDKYQDHMQERIDNYENLTVPFVADDYLVRHAYKNPNEIYSEISE
VAKLKDAKSEVKKSQYFSTFTLRGSYTGGASKGKLEDQKAMNKFIDDSLKKLDTYS
WSGYKTLTAYFTNYKVDSSNRVTYDVVFHGYLPNEGDSKNSLPYGKINGTYKGTEK
EKIKFSSEGSFDPDGKIVSYEWDFGDGNKSNEENPEHSYDKVGTYTVKLKVTDDKGE
SSVSTTTAEIKDLSENKLPVIYMHVPKSGALNQKVVFYKGTYDPDGSIAGYQWDFG
DGSDFSSEQNPSHVYTKKGEYTVTLRVMDSSGQMSEKTMKIKITDPVYPIGTEKEPN
NSKETASGPIVPGIPVSGTIENTSDQDYFYFDVITPGEVKIDINKLGYGGATWVVYDE
NNNAVSYATDDGQNLSGKFKADKPGRYYIHLYMFNGSYMPYRINIEGSVGR

FIG. 18A

SEQ ID NO: 6

AVDKNNATAAVQNESKRYTVSYLKTLNYYDLVDLLVKTEIENLPDLFQYSSDAKEF
YGNKTRMSFIMDEIGRRAPQYTEIDHKGIPTLVEVVRAGFYLGFHNKELNEINKRSFK
ERVIPSILAIQKNPNFKLGTEVQDKIVSATGLLAGNETAPPEVVNNFTPIIQDCIKNMD
RYALDDLKSKALFNVLAAPTYDITEYLRATKEKPENTPWYGKIDGFINELKKLALYG
KINDNNSWIIDNGIYHIAPLGKLHSNNKIGIETLTEVMKIYPYLSMQHLQSADQIERHY
DSKDAEGNKIPLDKFKKEGKEKYCPKTYTFDDGKVIIKAGARVEEEKVKRLYWASK
EVNSQFFRVYGIDKPLEEGNPDDILTMVIYNSPEEYKLNSVLYGYDTNNGGMYIEPD
GTFFTYERKAEESTYTLEELFRHEYTHYLQGRYAVPGQWGRTKLYDNDRLTWYEEG
GAELFAGSTRTSGILPRKSIVSNIHNTTRNNRYKLSDTVHSKYGASFEFYNYACMFM
DYMYNKDMGILNKLNDLAKNNDVDGYDNYIRDLSSNHALNDKYQDHMQERIDNY
ENLTVPFVADDYLVRHAYKNPNEIYSEISEVAKLKDAKSEVKKSQYFSTFTLRGSYT
GGASKGKLEDQKAMNKFIDDSLKKLDTYSWSGYKTLTAYFTNYKVDSSNRVTYDV
VFHGYLPNEGDSKNSLPYGKINGTYKGTEKEKIKFSSEGSFDPDGKIVSYEWDFGDG
NKSNEENPEHSYDKVGTYTVKLKVTDDKGESSVSTTTAEIKDLSENKLPVIYMHVPK
SGALNQKVVFYGKGTYDPDGSIAGYQWDFGDGSDFSSEQNPSHVYTKKGEYTVTLR
VMDSSGQMSEKTMKIKITDPVYPIGTEKEPNNSKETASGPIVPGIPVSGTIENTSDQDY
FYFDVITPGEVKIDINKLGYGGATWVVYDENNNAVSYATDDGQNLSGKFKADKPGR
YYIHLYMFNGSYMPYRINIEGSVGR

FIG. 18B

NUCLEIC ACID MOLECULES ENCODING CLOSTRIDIUM HISTOLYTICUM COLLAGENASE II AND METHODS OF PRODUCING THE SAME

RELATED APPLICATIONS

This application is a continuation of U.S. patent application Ser. No. 16/816,097, which was filed on Mar. 11, 2020, which is a continuation of U.S. patent application Ser. No. 15/669,286, which was filed on Aug. 4, 2017 (U.S. Pat. No. 10,603,365), which is a divisional of U.S. patent application Ser. No. 14/328,772, which was filed on Jul. 11, 2014 (U.S. Pat. No. 9,757,435), which is a continuation application of International Application No. PCT/US13/020940, which designated the United States and was filed on Jan. 10, 2013, published in English which claims the benefit of U.S. Provisional Application No. 61/585,909, which was filed on Jan. 12, 2012. The entire contents of each of the above-referenced applications are incorporated by reference herein.

SEQUENCE LISTING

The contents of the electronic sequence listing (117326000546_Sequence Listing.xml; Size: 51,192 bytes; and Date of Creation: May 26, 2023) is herein incorporated by reference in its entirety.

BACKGROUND OF THE INVENTION

Collagen is the major structural constituent of mammalian organisms and makes up a large portion of the total protein content of skin and other parts of the animal body. In humans, it is particularly important in the processes of wound healing process and natural aging. Various skin traumas, including burns, surgery, and infection, are characterized by the accumulation of fibrous tissue rich in collagen and having increased proteoglycan content. In addition to the replacement of the normal tissue which has been damaged or destroyed, excessive and disfiguring deposits of new tissue sometimes form during the healing process. The excess collagen deposition has been attributed to a disturbance in the balance between collagen synthesis and collagen degradation.

Diseases and conditions associated with excess collagen deposition and the erratic accumulation of fibrous tissue rich in collagen can be referred to as "collagen-mediated diseases." Collagenase, an enzyme that has the specific ability to digest collagen, has been used to treat a variety of collagen-mediated diseases, including, for example, Dupuytren's contracture, Peyronie's disease, lipoma and adhesive capsulitis. U.S. Pat. Nos. 6,086,872 and 5,589,171, incorporated herein by reference, disclose the use of collagenase preparations in the treatment of Dupuytren's disease. U.S. Pat. No. 6,022,539, incorporated herein by reference, discloses the use of collagenase preparations in the treatment of Peyronie's disease. U.S. Pat. Nos. 6,958,150 and 7,842,673, incorporated herein by reference, disclose the use of collagenase for the treatment of lipoma. U.S. Patent Application Publication No. 2006/020448A1, incorporated herein by reference, discloses the use of collagenase in the treatment of adhesive capsulitis. Collagenase for use in therapy may be obtained from a variety of sources including mammalian, fungal, and bacterial sources. One common source of crude collagenase is from a bacterial fermentation process, specifically the fermentation of *Clostridium histolyticum* (*C. histolyticum*). The crude collagenase obtained from *C. histolyticum* may be purified using any of a number of chromatographic techniques.

One drawback of the fermentation of bacteria is that various toxins will be produced, that if present in the therapeutic composition, would be detrimental to the health of the patient. For example, *C. histolyticum* fermentation results in the synthesis of the hemolytic toxins alpha and epsilon, which can cause lysis of red blood cells (hemolysis), potentially leading to hemolytic crisis and hemolytic anemia. Hemolytic crisis occurs when there is a rapid destruction of large numbers of red blood cells in conjunction with the body's inability to replenish the red blood cells quickly enough to reestablish normal red blood cell levels. A hemolytic crisis causes acute (and often severe) hemolytic anemia, and can result in fatigue, shortness of breath, dizziness, headache, coldness in the hands and feet, pale skin, chest pain, jaundice, pain in the upper abdomen, leg ulcers and pain, severe reactions to a blood transfusion, arrhythmias, an enlarged heart, and heart failure. In order to ensure that the therapeutic collagenase preparation does not contain hemolytic toxins that might be expressed during *C. histolyticum* fermentation, a method for releasing a drug product prior to administration to a patient is presented.

As discussed above, collagenase for use in therapy can be obtained from a variety of sources such as bacterial sources (e.g. from the fermentation of *C. histolyticum*). It would be useful to develop additional sources of collagenase such as recombinant forms of collagenase enzymes.

SUMMARY OF THE INVENTION

In some aspects, the present invention is based on the discovery of mutated polynucleotide sequences that encode functional collagenase I and collagenase II. The invention thus encompasses recombinant nucleic acid and polypeptides comprising the novel polynucleotide or polypeptide sequences and methods for the use thereof. The present invention also provides a method for detecting the secretion of a hemolytic toxin by a bacterial production strain, wherein the production strain produces a collagenase, prior to therapeutic administration of said collagenase to a patient and methods for detecting the presence of a hemolytic toxin in a collagenase composition.

In one embodiment, the invention is directed to a recombinant nucleic acid molecule comprising a polynucleotide having the sequence of SEQ ID NO: 1 (collagenase I nucleotide sequence) or the complement of SEQ ID NO: 1. In certain aspects, the recombinant nucleic acid further comprises a heterologous regulatory sequence operably linked to the polynucleotide. In certain additional embodiments, the invention is a recombinant nucleic acid molecule consisting of a polynucleotide of SEQ ID NO: 1. In yet additional aspects, the invention relates to a recombinant nucleic acid molecule consisting of a polynucleotide of SEQ ID NO: 1 and a heterologous regulator sequence operably linked to the polynucleotide.

In another embodiment, the invention is a recombinant nucleic acid molecule comprising a polynucleotide having the sequence of SEQ ID NO: 2 (collagenase II nucleotide sequence) or the complement of SEQ ID NO: 2. In certain aspects, the recombinant nucleic acid further comprises a heterologous promoter operatively linked to the polynucleotide. In certain additional embodiments, the invention is a recombinant nucleic acid molecule consisting of a polynucleotide of SEQ ID NO: 2. In yet additional aspects, the invention relates to a recombinant nucleic acid molecule consisting of a polynucleotide of SEQ ID NO: 2 and a heterologous regulator sequence operably linked to the polynucleotide.

The invention also includes recombinant polypeptides encoded by a recombinant nucleic acid comprising a polynucleotide having the sequence of SEQ ID NO: 1 or SEQ ID NO: 2.

In certain additional embodiments, the invention is directed to an expression cassette comprising a recombinant nucleic acid, wherein the nucleic acid comprises a polynucleotide having the sequence of SEQ ID NO: 1 or SEQ ID NO: 2.

In yet an additional embodiment, the invention is directed to a vector comprising a recombinant nucleic acid, wherein the nucleic acid comprises a polynucleotide having the sequence of SEQ ID NO: 1 or SEQ ID NO: 2. In some embodiments, the vector is a plasmid.

In a further aspect, the invention is directed to a recombinant host cell comprising the vector or plasmid comprising a polynucleotide having the sequence of SEQ ID NO: 1 or SEQ ID NO: 2. The invention also encompasses a method of producing collagenase I or collagenase II comprising culturing the host cell under conditions suitable for expression of the nucleic acid and recovering the collagenase I or collagenase II. The invention also includes a collagenase enzyme produced by culturing the recombinant host cell.

In some embodiments, the invention is directed to a recombinantly produced collagenase I comprising the amino acid sequence of SEQ ID NO: 3, a recombinantly produced collagenase II comprising the amino acid sequence SEQ ID NO: 4, a recombinantly produced collagenase I comprising the amino acid sequence of SEQ ID NO: 5, or a recombinantly produced collagenase II comprising the amino acid sequence of SEQ ID NO: 6.

Also included in the present invention are pharmaceutical compositions comprising collagenase I as described herein, collagenase II as described herein, or a combination thereof. In certain aspects, the present invention is directed to a pharmaceutical composition comprising a pharmaceutically acceptable carrier and a polypeptide comprising the amino sequence of SEQ ID NO: 3, a polypeptide comprising the amino acid sequence of SEQ ID NO: 4, or a combination thereof. In certain additional aspects, the present invention is directed to a pharmaceutical composition comprising a pharmaceutically acceptable carrier and a polypeptide comprising the amino sequence of SEQ ID NO: 5, a polypeptide comprising the amino acid sequence of SEQ ID NO: 6, or a combination thereof. The invention additionally includes methods of treating a collagen-mediated disease comprising administering an effective amount of collagenase I, collagenase II, or a combination thereof.

As discussed above, the invention encompasses methods for detecting the secretion of a hemolytic toxin by a bacterial production strain and methods for detecting the presence of a hemolytic toxin in a collagenase composition.

In one embodiment of the invention, a bacterial strain that produces collagenase is tested for the production of hemolytic toxins using a hemolysis assay. In one aspect, the hemolysis assay is performed using a blood agar substrate.

In another embodiment, a collagenase product is tested for the presence of hemolytic toxins using a hemolysis assay. In certain aspects, the hemolysis assay is performed using a blood agar substrate. In additional aspects, the hemolysis assay is performed using photometric detection of released hemoglobin. The absence of hemolytic toxins, as determined by a hemolysis assay or photometric detection, would support the release of the drug product for therapeutic administration.

Various strains of collagenase-producing bacteria can be assayed for hemolytic activity according to a method of the invention, in support of the release of a collagenase drug product for therapeutic administration. For example, members of the genera *Actinobacillus, Actinomadura, Bacillus, Bacteroides, Bifidobacterium, Brucella, Capnocytophaga, Clostridium, Enterococcus, Escherichia, Eubacterium, Flavobacterium, Fusobacterium, Peptococcus, Peptostreptococcus, Porphyromonas, Prevotella, Proteus, Pseudomonas, Serratia, Staphylococcus, Streptomyces, Streptococcus, Treponema*, and *Vibrio* can be assayed for hemolytic activity according to a method of the invention, in support of the release of a collagenase drug product for therapeutic administration.

In another embodiment, a collagenase product produced by, and purified from, a strain of collagenase-producing bacteria is assayed for hemolytic activity according to a method of the invention, in support of the release of a collagenase drug product for therapeutic administration. In some embodiments, the production strain is selected from, but not limited to, the above-listed genera. In another aspect of the invention, the production strain is an *Escherichia coli* (*E. coli*) strain, including forms of *E. coli* that have been transformed with recombinant forms of collagenase I and collagenase II. In certain aspects of the invention, the production strain is a *Clostridium perfringens* (*C. prefringens*) strain. In additional aspects, the production strain is a *C. histolyticum* strain.

In yet another embodiment of the invention, the collagenase composition is assayed for hemolytic activity according to a method of the invention, wherein the collagenase composition comprises a combination of purified *C. histolyticum* collagenase I and collagenase II. In an additional embodiment, the invention is a method of producing a drug product consisting of *C. histolyticum* collagenase I and II, wherein said method comprises testing a bacterial production strain for the absence of a functional, secreted hemolytic toxin according to a method of the invention.

In yet another embodiment, the invention is a method of purifying a crude collagenase composition, wherein said method comprises purifying the composition by filtration and column chromatography, followed by confirming the absence of a hemolytic toxin according to a method described herein.

In a further embodiment, the invention is a method of treating a collagen-mediated condition in a patient in need thereof, wherein said method comprises administering to said patient an effective amount of a drug product comprising collagenase, wherein the absence of a hemolytic toxin in said drug product or in a bacterial production strain producing said collagenase is confirmed according to a method of the invention prior to administration of said drug product to a patient, and/or formulation of the collagenase in a pharmaceutical composition.

Kits for testing for the presence or absence of hemolytic toxins in a sample are also described.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 shows protein alignment of *Clostridium septicum* (*C. septicum*) alpha toxin with the putative alpha toxin of *C. histolyticum* CLH_2834 and 2835. The *C. septicum* alpha toxin amino acid sequence (SEQ ID NO: 7) is the upper sequence in each row. The *C. histolyticum* CLH_2834 & 2835 (SEQ ID NO: 8) is the lower sequence in each row. The underlined, shaded sequence is the N-terminus of the mature *C. septicum* alpha toxin. The asterisks above the amino acids shows non-conserved essential residues critical for functionality (identifies mismatch in sequence). The shading shows conserved essential residues (confirms identity). The sequence numbering is based on the *C. septicum* sequence.

FIG. 2 shows blood agar plating of *C. septicum*. The arrows indicate beta hemolytic activity.

FIG. 3 shows amino acid alignment of *Bacillus proteolyticus* thermolysin with the putative delta toxin of *C. histolyticum* CLH_2576. The upper sequence in each row shows the sequence of *Bacillus proteolyticus* (*B. proteolyticus*) thermolysin protein (SEQ ID NO: 9). The lower sequence in each row is the sequence of *C. histolyticum* CLH_2576 (SEQ ID NO: 10). The green shading shows the proprotein region. The numbering is based on the thermolysin sequence.

FIG. 4 shows the prosequence amino acid alignment of *B. proteolyticus* thermolysin with the putative delta toxin of *C. histolyticum* CLH_2576. The upper sequence in each row is the prosequence of *B. proteolyticus* thermolysin protein (SEQ ID NO: 11). The lower sequence in each row is the prosequence of *C. histolyticum* CLH_2576 (SEQ ID NO: 12). The asterisks above the amino acids show the non-conserved essential residues critical for functionality (identifies mismatch in sequence). The green shading shows the conserved essential residues (confirms identity). The numbering is based on the thermolysin sequence.

FIG. 5 shows the mature sequence protein alignment of *B. proteolyticus* thermolysin with the putative delta toxin of *C. histolyticum* CLH_2576. The upper sequence in each row is the mature sequence of *B. proteolyticus* thermolysin (SEQ ID NO: 13). The lower sequence in each row is *C. histolyticum* CLH_2576 (SEQ ID NO: 14). The asterisks above the amino acids show non-conserved essential residues critical for functionality (identifies mismatch in sequence). The green shading shows conserved essential residues (confirms identity). The numbering is based on thermolysin sequence.

FIG. 6 shows the protein alignment of *C. perfringens* perfringolysin with the putative epsilon toxin of *C. histolyticum* CLH 1920. The upper sequence in each row is *C. perfringens* perfringolysin amino acid sequence (SEQ ID NO: 15). The lower sequence in each row is the amino acid sequence of *C. histolyticum* CLH 1920 (SEQ ID NO: 16). The blue star shows the signal peptidase cleavage site of perfringolysin K43. The asterisks above the amino acids show non-conserved essential residues critical for functionality (identifies mismatch in sequence). The green shading shows conserved essential residues (confirms identity). The numbering is based on the perfringolysin sequence.

FIG. 8 shows the protein alignment of *C. histolyticum* clostripain with the putative gamma toxin of *C. histolyticum* CLH 1861. The upper sequence in each row is *C. histolyticum* clostripain amino acid sequence (SEQ ID NO: 17). The lower sequence in each row is *C. histolyticum* CLH 1920 amino acid sequence (SEQ ID NO: 18). The asterisks above the amino acids shows non-conserved essential residues critical for functionality (identifies mismatch in sequence). The green shading shows the conserved essential residues (confirms identity). The numbering based on clostripain X63673 sequence.

FIGS. 9A and 9B show an alignment comparison of the translated amino acid sequence from colG and the amino acid sequence of SEQ ID NO: 3 (the translated amino acid sequence from CLH 1768 and 1769; the upper sequence). As shown in FIGS. 9A and 9B, the mature protein encoded by the amino acid sequence of SEQ ID NO: 3 differs from the translated amino acid sequence from colG amino acid sequence by three amino acids. The N-terminus of the mature protein begins at Ile 119 of the sequence of SEQ ID NO: 3. The amino acid sequence of the mature protein beginning at Ile 119 of SEQ ID NO: 3 is SEQ ID NO: 5.

FIGS. 10A and 10B show an alignment comparison of the translated amino acid sequence from colH and SEQ ID NO: 4 (the translated amino acid sequence from CLH 2116; the bottom sequence). As shown in FIGS. 10A and 10B, the mature protein encoded by the amino acid sequence of SEQ ID NO: 4 differs from the translated colG amino acid sequence by eight amino acids. The N-terminus of the mature protein begins at Ala 31 in colG and in SEQ ID NO: 4. The amino acid sequence of the mature protein beginning at Ala 31 of SEQ ID NO: 4 is SEQ ID NO: 6.

FIGS. 11A and 11B show the nucleotide sequence of SEQ ID NO: 1 (CLH 1768 and 1769; collagenase I).

FIGS. 12A and 12B show the nucleotide sequence of SEQ ID NO: 2 (CLH 2116; collagenase II).

FIGS. 13A and 13B show the amino acid and nucleotide sequence of SEQ ID NO: 8 and SEQ ID NO: 21, respectively (CLH 2835 and CLH 2834; alpha toxin).

FIGS. 14A and 14B show the amino acid and nucleotide sequence of SEQ ID NO: 10 and SEQ ID NO: 22, respectively (CLH 2576; delta toxin).

FIGS. 15A and 15B show the amino acid and nucleotide sequence of SEQ ID NO: 16 and SEQ ID NO: 23, respectively (CLH 1920; epsilon toxin).

FIGS. 16A and 16B show the amino acid and nucleotide sequence of SEQ ID NO: 18 and SEQ ID NO: 24, respectively (CLH 1861; gamma toxin).

FIG. 17A shows the amino acid sequence of SEQ ID NO: 3 (colG).

FIG. 17B shows the amino acid sequence of SEQ ID NO: 5.

FIG. 18A shows the amino acid sequence of SEQ ID NO: 4 (colH).

FIG. 18B shows the amino acid sequence of SEQ ID NO: 6.

DETAILED DESCRIPTION OF THE INVENTION

Figure 7:
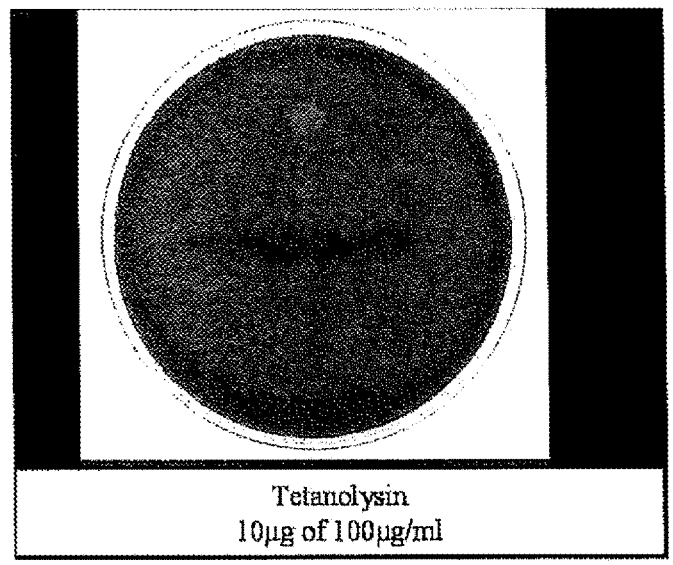
FIG. 7 shows the beta hemolytic phenotype of tetanolysin.

A description of preferred embodiments of the invention follows.

The words "a" or "an" are meant to encompass one or more, unless otherwise specified. For example, "a hemoloytic toxin" refers to one or more hemolytic toxins.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes); the contents of each of which are expressly incorporated by reference herein.

A. Recombinant Nucleic Acids and Proteins

A major source of collagenase is from the fermentation of *C. histolyticum*. An injectable formulation comprising *C. histolyticum* collagenase I and collagenase II is sold under the trade name XIAFLEX® and is approved by the U.S. Food and Drug Administration for the treatment of Dupuytren's contracture. Amino acid sequences for collagenase I and collagenase II encoded by the colG and colH genes, respectively, have been described in the literature. For example, colG is described in GenBank Acc. No. D87215 and Matsushita et al. (1999), *Journal of Bacteriology* 181 (3): 923-933, and colH has been described in GenBank Acc. No. D29981 and Yoshihara et al. (1994), *Journal of Bacteriology* 176(21): 6489-6496, the contents of each of which are expressly incorporated by reference herein. The present invention is based partially on sequencing analysis of the genes encoding collagenase I and collagenase II in a *C. histolyticum* strain (Clone 004 described below in the Examples) which produces and secretes functional collagenase I and collagenase II. The nucleotide sequences of the genes encoding collagenase I and collagenase II were found to be different from the literature-described sequences for *C. histolyticum* (e.g., GenBank Acc. Nos. D87125 and D29981) (SEQ ID NO: 19 and 20) (FIGS. 9 and 10).

Collagenase I and collagenase II are metalloproteases and require tightly bound zinc and loosely bound calcium for their activity (Eddie L. Angleton and H. E. Van Wart, Biochemistry 1988, 27, 7406-7412). Collagenase I and collagenase II have broad specificity toward all types of collagen (Steinbrink, D; Bond, M and Van Wart, H; (1985), *JBC*, 260 p 2771-2776). Collagenase I and collagenase II digest collagen by hydrolyzing the triple-helical region of collagen under physiological conditions (Steinbrink, D; Bond, M and Van Wart, H; (1985), *JBC*, 260 p 2771-2776). Even though each collagenase shows different specificity (e.g., each has a different preferred amino sequence for cleavage), together, they have synergistic activity toward collagen (Mandl, I., (1964), Biochemistry, 3: p. 1737-1741; Vos-Scheperkeuter, GH, (1997), *Cell Transplantation*, 6: p. 403-412).

The invention encompasses a recombinant nucleic acid molecule comprising or consisting of a polynucleotide of SEQ ID NO: 1 or the complement of SEQ ID NO: 1. In certain aspects, the recombinant nucleic acid further comprises a heterologous regulatory sequence operably linked to the polynucleotide. The invention further encompasses a recombinant nucleic acid molecule comprising or consisting of a polynucleotide of SEQ ID NO: 2 or the complement of SEQ ID NO: 2. In certain aspects, the recombinant nucleic acid further comprises a heterologous promoter operatively linked to the polynucleotide.

The invention also encompasses recombinant polypeptides encoded by the recombinant nucleic acids described herein. In some aspects, the recombinant polypeptides are encoded by the recombinant nucleic acids comprising or consisting of a nucleotide sequence selected from the group consisting of SEQ ID NO: 1 and SEQ ID NO: 2. In some embodiments, the recombinant polypeptide comprises the amino acid sequence of SEQ ID NO: 3 or SEQ ID NO: 4. In additional embodiments, the recombinant polypeptide comprises the amino acid sequence of SEQ ID NO:5 (the mature collagenase I protein, beginning at Ile 119 of SEQ ID NO: 3 in FIGS. 9A and 9B) or SEQ ID NO:6 (the mature collagenase II protein, beginning at Ala 31 of SEQ ID NO: 4 in FIGS. 10A and 10B). In yet another embodiment, the recombinant polypeptide consists of the amino acid sequence of SEQ ID NO: 3, SEQ ID NO: 4, SEQ ID NO: 5 or SEQ ID NO: 6.

In yet another embodiment, the invention is directed to a recombinant nucleic acid that encodes a polypeptide which comprises or consists of the amino acid sequence of SEQ ID NO:3 or SEQ ID NO:4. In a further embodiment, the invention is directed to a recombinant nucleic acid that encodes a polypeptide which comprises or consists of the amino acid sequence of SEQ ID NO: 5 or SEQ ID NO: 6. In a further aspect, the recombinant nucleic acid comprises a nucleotide sequence that encodes a polypeptide of amino acid sequence SEQ ID NO: 3, SEQ ID NO: 4, SEQ ID NO: 5 or SEQ ID NO: 6.

A recombinant nucleic acid is a nucleic acid molecule that contains, in addition to a polynucleotide sequence described herein (for example, the polynucleotide sequence of SEQ ID NO: 1 or SEQ ID NO: 2), a further heterologous coding or non-coding nucleotide sequence. The term "heterologous" means that the polynucleotide originates from a different species or from the same species, however, from another location in the genome than said added nucleotide sequence. Recombinant polypeptides or proteins refer to polypeptides or proteins produced using recombinant techniques, for example, those proteins or polypeptides produced from cells transformed by an exogenous nucleic acid construct encoding the desired polypeptide or protein.

The invention also relates to nucleic acids comprising the polynucleotide sequence of SEQ ID NO: 1 or SEQ ID NO: 2, wherein said nucleic acid is operatively linked to a regulatory sequence. The invention further relates to nucleic acids comprising a polynucleotide that encodes a polypeptide comprising the amino acid sequence of SEQ ID NO: 3, SEQ ID NO: 4, SEQ ID NO: 5 or SEQ ID NO: 6, wherein said nucleic acid is operatively linked to a regulatory sequence. Regulatory sequences include those regulatory sequences which direct constitutive expression of a nucleotide sequence in many types of host cells and/or those which direct expression of the nucleotide sequence only in certain host cells (e.g., tissue-specific regulatory sequences). Non-limiting examples of regulatory sequences are promoters and enhancers. Regulatory sequences also include other expression control elements, for example, those described in Goeddei, Gene Expression Technology: Methods in Enzymology 185, Academic Press, San Diego, CA (1990), the contents of which are expressly incorporated by reference herein. A nucleic acid is "operably linked" to a regulatory sequence when the nucleic acid molecule is linked to the regulatory sequence in a manner which allows expression of the nucleic acid sequence.

A nucleic acid molecule described herein can additionally be fused to a marker sequence, for example, a sequence that encodes a polypeptide to assist in isolation or purification of the polypeptide. Such sequences include, but are not limited to, those which encode a glutathione-S-transferase (GST) fusion protein, those which encode a hemaglutin A (HA) polypeptide marker from influenza, and those which encode hexa-histidine peptide, such as the tag provided in a pQE vector (Qiagen, Inc.). In certain aspects, the invention is directed to a polypeptide comprising an amino acid sequence of SEQ ID NO: 3, SEQ ID NO: 4, SEQ ID NO: 5, or SEQ ID NO: 6, wherein said polypeptide is fused a marker amino acid sequence.

In a further aspect, the invention is directed to a nucleic acid that is a variant of the nucleotide sequence of SEQ ID NO: 1 or SEQ ID NO: 2. A variant nucleic acid is a nucleic acid that includes an nucleotide substitution, addition or deletion relative to nucleotide sequence of SEQ ID NO: 1 or SEQ ID NO: 2. In some aspects, the variant is a nucleic acid that encodes identical or substantially identical amino acid sequences as that of the nucleotide sequences of SEQ ID NO: 1 or SEQ ID NO: 2. As will be understood by the skilled artisan, because of the degeneracy of the genetic code, several different nucleic acid sequences can encode a given protein. For instance, the codons GCA, GCC, GCG and GCU each encode the amino acid alanine. Thus, for example, at every position where a specific amino acid is specified by one codon, the codon can be changed to any of the corresponding codons that encode the same amino acid without altering the amino acid sequence of the encoded polypeptide. One of ordinary skill in the art will understand that each codon in a nucleotide sequence (except AUG, which is the only codon for methionine, and TGG, which is usually the only codon for tryptophan) can be modified to yield a functionally identical molecule.

In certain embodiments, the invention is directed to polypeptide comprising or consisting of amino acid sequence of SEQ ID NO: 3, SEQ ID NO: 4, SEQ ID NO: 5 or SEQ ID NO: 6, wherein one or more amino acids have been deleted or added, wherein the polypeptide possesses the activity of degrading or lysing collagen. In yet an additional embodiment, the polypeptide comprises or consists of the amino acid sequence of SEQ ID NO: 3, SEQ ID NO: 4, SEQ ID NO: 5 or SEQ ID NO: 6, wherein one or more amino acid residues have been replaced with a different amino acid residue, wherein the polypeptide possesses the activity of degrading or lysing collagen and wherein the polypeptide comprises or consists of an amino acid sequence that is different from the amino acid sequences of GenBank Acc. Nos. D87125 (SEQ ID NO: 19) and D29981 (SEQ ID NO: 20). In certain aspects, when an amino acid is replaced, the replacement is a conservative amino acid change. A conservative amino acid change is, for example, substitution of a nonpolar amino acid for another nonpolar amino acid or substitution of a polar amino acid for another polar amino acid or substitution of a positively charged amino acid for another positively charged amino acid, and the like. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

An isolated nucleic acid and an isolated polypeptide are not in the form or environment in which they exist in nature. For example, an isolated nucleic acid is one that is separated from the nucleotides which normally flanks the nucleic acid molecule in nature. Recombinant nucleic acids and recombinant nucleic acids within a vector are also an example of an isolated nucleic acid. Also, isolated nucleic acid molecules include recombinant nucleic acid molecules in heterologous host cells, as well as partially or substantially purified nucleic acid molecules in solution.

As described in more detail below, the invention also encompasses recombinant host cells, such as bacterial cells, fungal cells, plants cells, insect cells, avian cells, amphibian cells and mammalian cells, comprising the nucleic acid molecules described herein.

An expression cassette is a nucleotide sequence which is capable of affecting expression of a structural gene (i.e., a protein coding sequence, such as a collagenase of the invention) in a host compatible with such sequences. Expression cassettes can include a promoter operably linked with the polypeptide coding sequence; and, optionally, with other sequences, e.g., transcription termination signals. Additional factors necessary or helpful in effecting expression may also be used, e.g., enhancers.

The invention also relates to vectors comprising a nucleic acid of the invention. In one embodiment, the nucleic acid is SEQ ID NO: 1 or SEQ ID NO: 2, or a complement thereof. In another embodiment, the nucleic acid is a nucleic acid that encodes a polypeptide having the amino acid sequence of SEQ ID NO: 3, SEQ ID NO: 4, SEQ ID NO: 5 or SEQ ID NO: 6. A "vector" is a nucleic acid molecule capable of transporting another nucleic acid to which it has been linked. A non-limiting example of a vector is a plasmid which is a circular double stranded DNA into which an additional DNA segment can be ligated. Another example of a vector is a viral vector, wherein an additional DNA segment is ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Expression vectors are capable of directing the expression of genes to which they are operably linked. Such expression vectors include, for example, plasmids. The invention encompasses other expression vectors, such as viral vectors (e.g., replication defective retroviruses, adenoviruses and adeno-associated viruses) that are capable of directing gene expression. As will be appreciated by the skilled artisan, the design of the expression vector depends on several factors, such as the choice of the host cell to be transformed, the level of expression of protein desired, and the like. Expression vectors include one or more regulatory sequences which are selected based on the host cell to be used for expression. As discussed above, the regulatory sequence is operably linked to the nucleic acid to be expressed, for example, a nucleic acid of the invention. In some embodiments, the regulatory sequence is a regulatory sequence native to the transformed host cell. An expression vector can comprise one or more selectable markers, including, but not limited to, the gene that encodes dihydrofolate reductase and the genes that confer resistance to neomycin, tetracycline, ampicillin, chloramphenicol, kanamycin and streptomycin resistance.

Prokaryotic and eukaryotic host cells can be transfected by the vectors described herein. Host cells which can be transfected with the vectors of the present invention include, but are not limited to, bacterial cells such as *E. coli* (e.g., *E. coli* K12 strains), *Streptomyces, Pseudomonas, Serratia marcescens* and *Salmonella typhimurium*, insect cells (baculovirus), including *Drosophila*, fungal cells, such as yeast cells, plant cells and mammalian cells, such as thymocytes, Chinese hamster ovary cells (CHO), COS cells, and *Lactococcus lactis* cells. In some embodiments, the host cell is a bacterial cell. In yet another embodiment, the host cell is an *E. coli* strain. In yet an additional embodiment, the host cell is *Lactococcus lactis* cell. Methods for the production of recombinant polypeptides in *Lactococcus lactis* bacteria have been described, for example, in U.S. Pat. No. 7,358,067, the contents of which are expressly incorporated by reference herein. In one embodiment, the host cell is *Lactococcus lactis* and the nucleic acid comprises the nucleotide sequence of SEQ ID NO: 1 or SEQ ID NO: 2 operably linked to pH regulatable promoter P170 and derivatives thereof. The P170 promoter and derivatives thereof have been described in detail in WO 94/16086 and WO 98/10079, the contents of which are incorporated by reference herein.

Ligating the nucleic acid molecule into a gene construct, such as an expression vector, and transforming or transfecting into hosts, either eukaryotic (yeast, avian, insect, plant or mammalian) or prokaryotic (bacterial cells), are standard procedures. A vector described herein can be introduced into prokaryotic or eukaryotic cells using conventional transformation or transfection techniques, including, but not limited to, calcium phosphate or calcium chloride co-precipitation, DEAE-dextran-mediated transfection, lipofection, or electroporation. The polypeptides of the present invention can be isolated or purified (e.g., to homogeneity) from recombinant cell culture by a variety of processes.

The invention encompasses methods of producing a functional collagenase I or collagenase II or a combination thereof comprising culturing a host cell transformed or transfected with a vector comprising a nucleic acid of the invention. The method additionally comprises isolating the polypeptide from the medium or the host cell. A functional collagenase is a polypeptide that has a biological activity of a naturally-occurring collagenase, for example, a collagenase that possesses the ability to degrade collagen.

The polypeptide can be isolated by methods including, but not limited to, anion or cation exchange chromatography, ethanol precipitation, affinity chromatography and high performance liquid chromatography (HPLC), or a combination of any of thereof. The particular method used will depend upon the properties of the polypeptide and the selection of the host cell; appropriate methods will be readily apparent to those skilled in the art.

In some embodiments, the invention is a method of producing collagenase I or collagenase II, said method comprising the steps of (i) constructing a recombinant bacterium comprising the nucleotide sequence of SEQ ID NO: 1 or SEQ ID NO:2, or the polynucleotide encoding the polypeptide sequence of SEQ ID NO: 3, 4, 5 or 6 operably linked to an appropriate regulatory sequence; (ii) cultivating said recombinant bacterium under suitable conditions to express the gene, and (iii) harvesting from the recombinant bacterium, the collagenase I or collagenase II. The collagenase I and collagenase II can be purified by a variety of methods known to those skilled in the art, including dye ligand affinity chromatography, heparin affinity chromatography, ammonium sulfate precipitation, hydroxylapatite chromatography, size exclusion chromatography, ion exchange chromatography, and metal chelation chromatography. In some embodiments, the collagenase I and collagenase II are purified via filtration and column chromatography and the purified collagenase I and II are combined in a ratio of about 1 to 1 using methods described in U.S. Pat. No. 7,811,250, the contents of which are expressly incorporated by reference herein.

Examples of collagen mediated-diseases that can be treated by the compositions (comprising collagenase I, collagenase II, or a combination thereof encoded by the nucleic acids described herein and/or comprising the amino acid sequences of SEQ ID NO: 3 and/or SEQ ID NO: 4) and methods of the invention include, but are not limited to, Dupuytren's disease, Peyronie's disease, frozen shoulder (adhesive capsulitis), keloids, hypertrophic scars, depressed scars, such as those resulting from inflammatory acne; post-surgical adhesions, acne vulgaris, lipomas, and disfiguring conditions such as wrinkling, cellulite formation and neoplastic fibrosis. U.S. Pat. Nos. 6,086,872 and 5,589,171, incorporated herein by reference, disclose the use of collagenase preparations in the treatment of Dupuytren's disease. U.S. Pat. No. 6,022,539, incorporated herein by reference, discloses the use of collagenase preparations in the treatment of Peyronie's disease.

In addition to its use in treating collagen-mediated diseases, a composition comprising a recombinant polypeptide described herein is also useful for the dissociation of tissue into individual cells and cell clusters as is useful in a wide variety of laboratory, diagnostic and therapeutic applications. These applications involve the isolation of many types of cells for various uses, including microvascular endothelial cells for small diameter synthetic vascular graft seeding, hepatocytes for gene therapy, drug toxicology screening and extracorporeal liver assist devices, chondrocytes for cartilage regeneration, and islets of Langerhans for the treatment of insulin-dependent diabetes mellitus. Enzyme treatment works to fragment extracellular matrix proteins and proteins which maintain cell-to-cell contact. Since collagen is the principle protein component of tissue ultrastructure, the enzyme collagenase has been frequently used to accomplish the desired tissue disintegration. In general, the composition of the present invention is useful for any application where the removal of cells or the modification of an extracellular matrix, are desired.

The invention encompasses pharmaceutical compositions comprising a pharmaceutically acceptable carrier and collagenase I and/or collagenase II produced according to a method described herein. In yet another embodiment, the pharmaceutical compositions comprises collagenase I comprising or consisting of the amino acid sequence of SEQ ID NO: 3 or SEQ ID NO: 5. In a further embodiment, the pharmaceutical composition comprises collagenase II comprising or consisting of the amino acid sequence of SEQ ID NO: 4 or SEQ ID NO: 6. In yet another aspect, the pharmaceutical composition comprises a pharmaceutically acceptable carrier and a collagenase I and collagenase II as described herein. In a further aspect, the pharmaceutical composition comprises a pharmaceutically acceptable carrier and the collagenase I and collagenase II at 1:1 mass ratio. The pharmaceutical composition of the present invention comprises an effective amount of a collagenase the present invention formulated together with one or more pharmaceutically acceptable carriers or excipients.

B. Methods of Detecting the Presence of a Hemolytic Toxin

In some embodiments, the invention encompasses methods of detecting the presence of a hemolytic toxin in a bacterial fermentation, wherein the bacterial fermentation produces a collagenase. In certain aspects, the invention provides a method for releasing a collagenase drug product prior to the therapeutic administration of said collagenase drug substance to a patient comprising detecting the presence of a hemolytic toxin in the drug product production strain. The term "drug product production strain," "production strain," "collagenase production strain," and "bacterial production strain" are used interchangeably and refer to a bacterial strain from which a collagenase is obtained. In other aspects, the invention provides a method for releasing a collagenase drug product prior to the therapeutic administration of said collagenase drug product to a patient, comprising detecting the presence of a hemolytic toxin in the drug product.

As used herein, the phrase "releasing a collagenase drug product" means to confirm the absence of a hemolytic toxin in the collagenase drug product. It is understood that the terms "drug substance", "drug product" or "collagenase composition" can be used interchangeably. Also as used herein, the terms "hemolysin" and "hemolytic toxin" are used interchangeably, and refer to a toxin that is responsible for the lysis of a red blood cell.

It has been discovered that the collagenase production strain and drug product can be assayed for the presence or absence of hemolytic activity, ensuring that the collagenase drug substance provides a highly reproducible and optimal enzymatic activity and superior therapeutic effect, while lowering the potential for side effects. In accordance with the invention, methods are provided for assaying the production strain or drug product for the secretion or presence of a functional hemolytic toxin that may be co-present with collagenase in the drug product. The invention encompasses a method of assaying a test sample for the presence of a hemolytic toxin, wherein the test sample comprises a bacterial production strain or a collagenase composition, comprising incubating the test sample with red blood cells, followed by detection of lysis of red blood cells.

Specific methods for detecting lysis of red blood cells are described throughout the literature, including, for example, 1) Ryan K J and Ray CG. Principles of laboratory diagnosis. In *Sherris medical microbiology: an introduction to infectious diseases*. Ryan K J, Ray C G, and Sherris J C (eds.) McGraw-Hill Professional, 2004; 229-260; and 2) Eschbach E et al. Improved erythrocyte lysis assay in microtitre plates for sensitive detection and efficient measurement of hemolytic compounds from ichthyotoxic algae. *Journal of Applied Toxicology* 21, 513-519 (2001), the contents of each of which are expressly incorporated by reference herein.

In one embodiment of the invention, the method comprises incubating samples of a collagenase production strain, a partially purified collagenase isolated from a collagenase production strain, or a collagenase drug product on a blood agar substrate, and observing the blood agar for zones of clearance after the period of incubation, wherein a zone of clearance indicates the lysis of red blood cells. If the bacterial product strain was tested, the lysis of red blood cells indicates the secretion of a functional hemolytic toxin from the bacterial production strain. If a partially purified collagenase or a collagenase drug product was tested, the lysis of red blood cells indicates the presence of a functional hemolytic toxin in the partially purified collagenase or in collagenase drug product. In certain embodiments, the production strain is a strain of *C. histolyticum*. The absence of a zone of clearance indicates the absence of a hemolytic toxin. The observed absence of zones of clearance indicate or confirm the absence of hemolytic toxins in the collagenase production strain, in the partially purified collagenase, or in the collagenase drug product, and allow the drug product to be released for therapeutic administration.

In another embodiment, the method comprises incubating red blood cells with extracts taken from a collagenase production strain, or with a partially purified collagenase isolated from a collagenase production strain, or with a collagenase drug product, followed by photometrically analyzing the incubation mixture for the lysis of red cells as indicated by the appearance of hemoglobin in the incubation mixture. A hemolytic toxin will lyse the red blood cells, releasing hemoglobin into the incubated sample. The photometric detection of hemoglobin can provide a sensitive assay for the presence of hemolytic toxins. In one aspect, red blood cells are incubated with extracts taken from a collagenase production strain, or with a partially purified collagenase isolated from a collagenase production strain, or with a collagenase drug product, and then photometrically analyzing the extracts for the presence of hemoglobin at a wavelength of 540 nm. In another aspect, the photometric analysis is performed at a wavelength of 414 nm. In yet another aspect, incubation and photometric analysis can be performed using microtiter plates. The absence of hemoglobin, and thus the absence of hemolytic toxins, would allow the release of the drug product for therapeutic administration to a patient.

Hemolytic toxins as found in *C. histolyticum* belong to two different families of hemolysins: aerolysin-like hemolysins, and oxygen-labile hemolysins. The aerolysin-like hemolysins are synthesized by the bacterium as inactive preproteins that are secreted into the extracellular environment as inactive protoxins. The inactive protoxins will bind to receptors on a target cell membrane, for example, receptors on a red blood cell where the protoxins are cleaved into their active structures by proteases. Once activated, the toxins oligomerize on the cell surface into a prepore complex, followed by insertion of a beta-barrel into the target cell membrane. The beta-barrel forms a pore in the membrane, allowing the rapid influx of calcium ions into the cell, with toxic consequences to the cell. The alpha toxin of *C. histolyticum* is most likely an aerolysin-like hemolysin, as it has been discovered to share significant homology with *Clostridium septicum* alpha toxin, which is a member of the aerolysin-like family of toxins, and which possess hemolytic activity (see, for example, Example 1 below).

Epsilon toxin of *C. histolyticum*, and tetanolysin of *Clostridium tetani* (*C. tetani*), have been described as an oxygen-labile hemolysins [Hatheway C L. *Clin Microbiol Rev* 3(1): 66-98 (1990)]. Epsilon toxin of *C. histolyticum* has been discovered to share homology with tetanloysin, which is a member of thiol-activated, beta-barrel, pore-forming toxins with affinity for cholesterol. Such proteins are part of a family of Cholesterol Dependent Cytolysins (CDC). These proteins are secreted by the bacterium into the extracellular environment as water-soluble monomeric proteins where they bind to target cell membranes, mediated by cholesterol binding. The toxin then oligomerizes on the membrane surface to form arcs and ring-like structures that are responsible for cytolysis. The epsilon toxin of *C. histolyticum* is known to be an oxygen-labile hemolysin, and is similar serologically to those oxygen-labile hemolysins produced by other strains of *Clostridium*, such as *C. tetani, C. novyi*, and *C. septicum*.

In certain aspects, the invention is directed to a method of detecting the presence of *C. histolyticum* alpha toxin in a bacterial production strain using an assay described herein. In other aspects, the invention is directed to a method of detecting the presence of *C. histolyticum* alpha toxin in a drug product. In a further aspect, the invention is directed to a method of detecting the presence of *C. histolyticum* epsilon toxin in a bacterial production strain. In yet another aspect, the invention is directed to a method of detecting the presence of *C. histolyticum* epsilon toxin in a drug product. In a still further aspect, the invention is directed to a method of detecting the presence of *C. histolyticum* alpha toxin and epsilon toxin in a bacterial production strain. In an additional embodiment, the invention is directed to a method of detecting the presence of *C. histolyticum* alpha toxin and epsilon toxin in a drug product.

The invention also encompasses a method of producing a drug product consisting of collagenase I and collagenase II, wherein the collagenase I and II are obtained from *C. histolyticum*, and wherein the method comprises the steps of fermenting a strain of *C. histolyticum* in which the absence of a functional, secreted hemolytic toxin has been confirmed by incubating the production strain with red blood cells under conditions suitable for lysis of red blood cells by a hemolytic toxin, wherein lysis of red blood cells indicates secretion of a hemolytic toxin and wherein the absence of lysis of the red blood cells indicates the absence of a hemolytic toxin. In another aspect, the invention is directed to a method of producing a drug product consisting of collagenase I and collagenase II, wherein the collagenase I and II are obtained from *C. histolyticum*, and wherein the method comprises the steps of confirming the absence of a functional, secreted hemolytic toxin in the drug product by incubating the drug product with red blood cells under conditions suitable for lysis of red blood cells by a hemolytic toxin, wherein lysis of red blood cells indicates secretion of a hemolytic toxin and wherein the absence of lysis of the red blood cells indicates the absence of a hemolytic toxin.

Further aspects of the invention include methods of purifying a crude collagenase composition comprising purifying the composition by filtration and column chromatography followed by confirming the absence of a hemolytic toxin by incubating a sample of the purified composition with red blood cells under conditions suitable for lysis of red blood cells by a hemolytic toxin, wherein lysis of red blood cells indicates secretion of a hemolytic toxin and wherein the absence of lysis of the red blood cells indicates the absence of a hemolytic toxin.

As discussed above, several diseases and conditions are associated with excess collagen deposition and the erratic accumulation of fibrous tissue rich in collagen and can be treated with collagen drug products. Such diseases and conditions are collectively referred to herein as "collagen-mediated diseases". The invention also encompasses a method of treating a collagen-mediated disease in a patient in need thereof, wherein the composition comprising collagenase is administered to said patient and wherein, prior to said administration, said composition or bacterial production strain is assayed for the presence or absence of hemolytic toxins using a method described herein. Examples of collagen mediated-conditions that may be treated by the compositions and methods described herein include but are not limited to: Dupuytren's disease; Peyronie's disease; frozen shoulder (adhesive capsulitis), keloids; hypertrophic scars; depressed scars such as those resulting from inflammatory acne; post-surgical adhesions; acne vulgaris; lipomas, and disfiguring conditions such as wrinkling, cellulite formation and neoplastic fibrosis. In certain aspects, the assayed composition is administered to a patient to treat Peyronie's or Dupuytren's diseases or adhesive capsulitis.

With respect to the production strain that can be assayed according to a method of the invention, it is known, for example, that collagenase is expressed by bacteria that are members of the genera *Actinobacillus, Actinomadura, Bacillus, Bacteroides, Bifidobacterium, Brucella, Capnocytophaga, Clostridium, Enterococcus, Escherichia, Eubacterium, Flavobacterium, Fusobacterium, Peptococcus, Peptostreptococcus, Porphyromonas, Prevotella, Proteus, Pseudomonas, Serratia, Staphylococcus, Streptomyces, Streptococcus, Treponema*, and *Vibrio*. In one embodiment of the invention, the production strain is selected from the above listed genera. In another embodiment, the production strain is an *E. coli* strain, including forms of *E. coli* that have been transformed with recombinant forms of collagenase I and collagenase II. In a more preferred embodiment, the production strain is a *C. perfringens* strain. In a most preferred embodiment, the production strain is a *C. histolyticum* (*C. his*) strain.

In certain aspects, the production strain produces a collagenase composition comprising a mixture of collagenase I and collagenase II. In a further embodiment, the production strain used to produce a mixture of collagenase I and collagenase I is *C. histolyticum*. In another embodiment, the collagenase drug product comprises a mixture of highly purified *C. histolyticum* collagenase I and collagenase II in a mass ratio of about 1 to 1.

Kits for testing for the presence of hemolysins in a sample are also presented, wherein a hemolysin is a substance that causes lysis of red blood cells. The kits allow the identification of test substances that are hemolytic, or contain, hemolysins. Test substances include, but are not limited to, chemical, biological, and radiation-emitting substances. In one embodiment, the kit comprises materials for testing for the presence of hemolysins in a test sample including, for example, a kit comprising red blood cells and related test materials. In another embodiment, the kit comprises a petri dish comprised of blood agar, a positive control, and a negative control comprised of a bacterial strain wherein the hemolytic genes are mutated or knocked out, and wherein no functional hemolytic proteins are produced. In yet another embodiment, the kit comprises red blood cells, microtiter plates, a positive control, and a negative control comprised of the drug product.

As will be understood, the inventive kits and methods can be used to detect the presence or absence of hemolysins in collagenase compositions, wherein the collagenase is obtained from a bacteria.

The crude collagenase obtained from *C. histolyticum* can be purified by a variety of methods known to those skilled in the art, including dye ligand affinity chromatography, heparin affinity chromatography, ammonium sulfate precipitation, hydroxylapatite chromatography, size exclusion chromatography, ion exchange chromatography, and metal chelation chromatography. Crude and partially purified collagenase is commercially available from many sources including Advance Biofactures Corp., Lynbrook, New York. Methods of purification of crude collagenase obtained from *C. histolyticum* are also described in U.S. Pat. No. 7,811, 560, the contents of which are expressly incorporated herein by reference. In certain embodiments, the purification procedure comprises the steps of: a) filtering the crude harvest through a MUSTANG Q anion-exchange capsule filter; b) adding ammonium sulphate; preferably to a final concentration of 1M; c) filtering the crude harvest; preferably through a 0.45 μm filter; d) subjecting the filtrate through a HIC column; preferably a phenyl sepharose 6FF (low sub); e) adding leupeptin to the filtrate; preferably to a final concentration of 0.2 μm to post HIC eluted product; f) removing the ammonium sulfate and maintaining leupeptin for correct binding of collagenase I and collagenase II with buffer exchange by TFF; preferably with buffer exchange by TFF; g) filtering the mixture of step; (f) preferably through a 0.45 μm filter; h) separating collagenase I and collagenase II using Q-Sepharose HP; i) preparing TFF concentration and formulation for collagenase I and collagenase II separately; wherein TFF is a tangential flow filtration using 10 and/or 30 K MWCO (molecular weight cut-off) PES or RC-polyethersulfone or regenerated cellulose filter membranes (TFF provides a means to retain and concentrate select protein and exchange the protein from one buffer solution into another); and j) filtering through a 0.2 μm filtration system.

C. *C. histolyticum* Alpha, Beta, Delta, Epsilon and Gamma Toxins

The amino acid sequences of the alpha, delta and epsilon toxins of *C. histolyticum* Clone 004 are shown in the Figures and are SEQ ID NO: 8, SEQ ID NO: 12 and SEQ ID NO:

16, respectively. The nucleotide sequences of the alpha, delta and epsilon toxins of *C. histolyticum* Clone 004 are also shown in the Figures and are SEQ ID NO: 21, SEQ ID NO: 22, and SEQ ID NO: 23, respectively. Each of the amino acid sequences of SEQ ID NO: 8, SEQ ID NO: 12, SEQ ID NO: 16 have sequence characteristics that render these proteins non-functional and/or unsecreted.

For the gamma toxin (clostripain), there are only three amino acid differences when compared to the model protein (see Examples section) and none of the amino acid residues which are found to differ in the *C. histolyticum* Clone 004 gamma toxin have been identified as essential for activity. Thus, it is predicted that the *C. histolyticum* Clone 004 gamma toxin (having the amino acid sequence of SEQ ID NO: 18) is secreted and functional. The nucleotide sequence of the *C. histolyticum* Clone 004 gamma toxin is SEQ ID NO: 24.

As discussed above, the beta toxins having amino acid sequences of SEQ ID NO: 3 and SEQ ID NO: 4 are fully functional.

As will be understood, one or more mutations (for example, deletion or addition of one or more amino acid residues or nucleic acid residues) can be introduced into the nucleotide and/or amino acid sequences of *C. histolyticum* alpha, beta, epsilon or gamma toxins (SEQ ID NO: 8, SEQ ID NO: 12, SEQ ID NO: 16 and SEQ ID NO: 18, SEQ ID NO: 21, SEQ ID NO: 22, SEQ ID NO: 23 and SEQ ID NO: 24). In certain aspects, one or mutations are introduced in order to improve or impair the activity, function, production and/or secretion of the toxin. In one embodiment, a mutation can be introduced that renders the alpha, beta, and/or epsilon toxins functional and/or secreted. In another embodiment, the sequence of the gamma toxin (SEQ ID NO: 18) can be mutated so as to render the protein non-functional and/or unsecreted.

Also encompassed by the present invention are methods of producing antibodies against *C. histolyticum* or a *C. histolyticum* toxin comprising administering to a subject an effective amount of a composition comprising a protein or peptide, wherein said protein or peptide comprises an amino acid sequence selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 3, SEQ ID NO: 4, SEQ ID NO: 5 and SEQ ID NO: 6, or a fragment or variant thereof, or a combination of any of thereof. In addition, the present invention includes methods of stimulating an immune response to a *C. histolyticum* toxin comprising administering to a subject an effective amount of a composition comprising a protein or peptide comprising an amino acid sequence selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 3, SEQ ID NO: 4, SEQ ID NO: 5 and SEQ ID NO: 6, or a fragment or variant thereof, or a combination of any of thereof. The invention also includes a vaccine comprising an effective amount of a protein or peptide comprising an amino acid sequence selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 3, SEQ ID NO: 4, SEQ ID NO: 5 and SEQ ID NO: 6, or a fragment or variant thereof, or a combination of any of thereof. The protein or peptide comprising an amino acid sequence selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 3, SEQ ID NO: 4, SEQ ID NO: 5 and SEQ ID NO: 6, or a fragment or variant thereof can be produced by a *C. histolyticum* strain or can be a recombinant protein or peptide.

D. Pharmaceutical Compositions Comprising Collagenase and Methods of Treatment

The invention described herein encompass pharmaceutical compositions comprising the protein sequences and recombinant proteins and also, pharmaceutical compositions comprising a collagenase drug product assayed according to methods described herein. As used herein, the term "pharmaceutically acceptable carrier or excipient" means a non-toxic, inert solid, semi-solid or liquid filler, diluent, encapsulating material or formulation auxiliary of any type. "Treating" or "treatment" includes the administration of the compositions, compounds or agents of aspects of the present invention to prevent or delay the onset of the symptoms, complications, or biochemical indicia of a disease, alleviating or ameliorating the symptoms or arresting or inhibiting further development of the disease, condition, or disorder. A "therapeutically effective amount" or an "effective amount" is an amount which, alone or in combination with one or more other active agents, can control, decrease, inhibit, ameliorate, prevent or otherwise affect one or more symptoms of a disease or condition to be treated. In the context of producing an immune response or in the preparation of a vaccine, an "effective amount" encompasses an amount effective to produce an immune response, including the generation of antibodies against an antigen.

Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, perfuming agents, preservatives and antioxidants can also be present in the composition, according to the judgment of the formulator.

Collagenase compositions can also be prepared by mixing either a specific number of activity units or specific masses of the preferably purified enzymes. Collagenase activity can be measured by the enzyme's ability to hydrolyze either synthetic peptide or collagen substrate. Those skilled in the art will recognize that enzyme assays other than those disclosed herein may also be used to define and prepare functionally equivalent enzyme compositions. Collagenase activity can be described, for example, in SRC units. One SRC unit will solubilize rat tail collagen into ninhydrin reaction material equivalent to 1 nanomole of leucine per minute, at 25° C. and pH 7.4. In certain embodiments of the present invention, collagenase activity is described in ABC units. This potency assay of collagenase is based on the digestion of undenatured collagen (from bovine tendon) at pH 7.2 and 37° C. for 20-24 hours. The number of peptide bonds cleaved is measured by reaction with ninhydrin. Amino groups released by a trypsin digestion control are subtracted. One net ABC unit of collagenase will solubilize ninhydrin reactive material equivalent to 1.09 nanomoles of leucine per minute. 1 SRC unit equals approximately 6.3 ABC units.

In certain aspects, the drug substance for injectable collagenase consists of two microbial collagenases, referred to as Collagenase AUX I and Collagenase ABC I and Collagenase AUX II and Collagenase ABC II. It is understood that the terms "Collagenase I", "ABC I", "AUX I", "collagenase AUX I", and "collagenase ABC I" mean the same and can be used interchangeably. Similarly, the terms "Collagenase II", "ABC II", "AUX II", "collagenase AUX II", and "collagenase ABC II" refer to the same enzyme and can also be used interchangeably. These collagenases are secreted by bacterial cells. They are isolated and purified from *C. histolyticum* culture supernatant by chromatographic methods. Both collagenases are special proteases and share the same EC number (E.C. 3.4.24.3).

Collagenase AUX I has a single polypeptide chain consisting of approximately 1000 amino acids with a molecular weight of 115 kDa. Collagenase AUX II has also a single polypeptide chain consisting of about 1000 amino acids with a molecular weight of 110 kDa.

In some embodiments, the drug substance (collagenase concentrate) has an approximately 1 to 1 mass ratio for collagenase AUX I and AUX II. In one embodiment, the collagenase concentrate has an extinction coefficient of 1.528.

The pharmaceutical compositions of this invention can be administered parenterally, topically, or via an implanted reservoir. The term "parenteral," as used herein, includes subcutaneous, intracutaneous, intravenous, intramuscular, intraarticular, intraarterial, intrasynovial, intrasternal, intrathecal, intralesional and intracranial injection or infusion techniques. In a preferred embodiment, the composition is injected into the affected tissue. In the case of Peyronie's or Duputyren's diseases or adhesive capsulitis, the composition is injected into the cord of the hand or the Peyronies' plaque. The term "local administration" is defined herein to embrace such direct injection into the affected tissue. In certain aspects, the pharmaceutical composition of the invention is an injectable formulation. In certain additional aspects, the pharmaceutical composition is a topical formulation.

Furthermore, depending on the treatment, improved results can, in some circumstances, be obtained by immobilizing the site of injection after administration of the pharmaceutical composition. For example, the site of administration (e.g., the hand), can be immobilized for 4 or more hours.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids, such as oleic acid, are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The sterile solutions may also be lyophilized for later use.

In some embodiments, the composition comprising collagenase is a lyophilized, injectable composition formulated with sucrose, Tris at a pH level of about 8.0. Generally, a source of calcium is included in the formulation, such as calcium chloride.

Dosage forms for topical or transdermal administration of a pharmaceutical compositions of this invention include ointments, pastes, creams, lotions, gels, powders, solutions, sprays, inhalants or patches. The active component is admixed under sterile conditions with a pharmaceutically acceptable carrier and any needed preservatives or buffers as may be required.

The ointments, pastes, creams and gels may contain, in addition to a polypeptide of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the polypeptides of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of an active agent to the body. Such dosage forms can be made by dissolving or dispensing the active agent in the proper medium. Absorption enhancers can also be used to increase the flux of the polypeptide across the skin. The rate can be controlled by either providing a rate-controlling membrane or by dispersing the polypeptide of the invention in a polymer matrix or gel.

Therapeutic administration of the pharmaceutical may be parenterally, topically, or via an implanted reservoir. The term parenteral as used herein includes subcutaneous, intracutaneous, intravenous, intramuscular, intraarticular, intraarterial, intrasynovial, intrasternal, intrathecal, intralesional and intracranial injection or infusion techniques. The term "local administration" is defined herein to embrace such direct injection. In one embodiment, therapeutic administration of the pharmaceutical composition is by injection.

Therapeutic administration of the pharmaceutical in dosage forms for topical or transdermal administration include ointments, pastes, creams, lotions, gels, powders, solutions, sprays, inhalants or patches. The active component is admixed under sterile conditions with a pharmaceutically acceptable carrier and any needed preservatives or buffers as may be required.

The ointments, pastes, creams and gels may contain, in addition to an active compound of the drug product, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of the drug product, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The invention will be better understood in connection with the following examples, which are intended as an illustration only and not limiting of the scope of the invention. Various changes and modifications to the disclosed embodiments will be apparent to those skilled in the art and such changes and modifications may be made without departing from the spirit of the invention and the scope of the appended claims.

EXAMPLES

Example 1: C. histolyticum Genome Sequencing and Toxin Sequence Analysis

A dearth of scientific studies related to the C. histolyticum alpha, delta and epsilon (α, δ, and ε toxins) has resulted in limited knowledge about the protein structure of these toxins. To address this knowledge deficit, a genome sequencing initiative was undertaken to more fully understand the production organism with particular focus on the identification of putative toxin genes. As a consequence of this effort, the complete genome of the Collagenase Clostridium Histolyticum production strain (Clone 004) (Auxilium Product Operation, Malvern, PA) has only recently been generated, representing apparently, the first time that the genome sequence of any C. histolyticum strain has been reported.

There were three fundamental steps involved in the genome sequence project. First, genomic DNA was extracted from a Clone 004 cultivation and forwarded to Creative Genomics for sequencing (Shirley, NY, USA). The genome sequence of C. histolyticum Clone 004 was obtained using industry standard methods. Second, the results obtained from the genome sequence were analyzed using standard bioinformatics methods (BLAST analysis) in order to query the sequence information against genome sequence databases. This second stage resulted in the assignment of protein information for each C. histolyticum gene that was identified. The use of two databases ensured a comprehensive evaluation but also served as a second source to verify the protein assignment. The third step in the project was a comparative analysis of the C. histolyticum putative toxin sequence with the protein assigned automatically by the BLAST analysis.

i. C. histolyticum Genome Sequencing and Identification of Model Proteins

Samples of genomic DNA isolated from an expansion of C. histolyticum (CLH) WCB derived from Clone 004 was forwarded to Creative Genomics (Shirley, NY, USA) for genome sequencing. Creative Genomics employed standard methods used for sequence determination of genomic DNA samples submitted by clients. The genome sequence was generated from Roche/454 GS-FLX system with titanium chemistry (fragment sequencing) accompanied with Illumina/Solexa Genome Analyzer. The ANI 3730x1 was employed to accomplish genome finishing by primer walking. The entire genome sequence of 2,842,906 base pairs with a 29.44% GC content was completed and these values were typical of the genome size and GC content obtained for other Clostridial genomes. Each of the 2,887 open reading frames (ORFs) identified was assigned a unique CLH number. Each of the putative 2,887 genes was further investigated using BLAST analysis of the GenBank and SwissProt databases resulted in the tentative assignment of the loci for beta, gamma, alpha, and epsilon toxins. The results of the initial assessment are presented in Table 1. Thus, the assignment of model proteins was completed as a result of an automated analysis via a comprehensive search of two databases. The model protein assignment was not influenced by operator interpretation.

TABLE 1

Assignments of Model Proteins for Putative CLH Toxins based upon Comparison with Two Sequence Databases

| Toxin | CLH Name | Common Name | Model Protein |
|---|---|---|---|
| alpha | CLH-2834 & 2835 | Lethal factor | Aerolysin/Hemolysin (C. septicum alpha toxin) |
| beta | CLH_1768 & 1769 | Collagenase I | Collagenase I from colG |
| beta | CLH_2116 | Collagenase II | Collagenase II from colH |
| epsilon | CLH_1920 | Oxygen labile hemolysin | C. perfringens perfringolysin C. tetani tetanolysin |
| gamma | CLH_1861 | Clostripain | C. histolyticum clostripain |

An inspection of the BLAST analysis results of the C. histolyticum genome did not reveal an ORF coding for an elastase. However, proteases have been classified by MEROPS (MEROPS.sanger.ac.uk/) based upon the criterion of the most prominent functional group in the active site of those proteases. Using this MEROPS based functional approach, an elastase falls into the M4 peptidase family of which thermolysin (EC 3.4.24.27) is the best studied member of the family and is the classical model for such proteases. Using this knowledge, a re-inspection of the BLAST analysis output suggested that C. histolyticum possesses a single ORF that shares significant homology with thermolysin. Therefore, the putative delta toxin gene within C. histolyticum has been assigned as a homolog of B. proteolyticus thermolysin.

The results of the initial assessment are presented in Table 2 below based upon comparison with two sequence databases.

TABLE 2

Assignments of Model Proteins for Putative CLH Toxins

| Toxin | CLH Name | Common Name | Model Protein |
|---|---|---|---|
| alpha | CLH 2834 & 2835 | Lethal factor | C. septicum alpha toxin |
| beta | CLH_1768 & 1769 | Collagenase I | Collagenase I from colG |
| beta | CLH_2116 | Collagenase II | Collagenase II from co/H |
| delta | CLH_2576 | Elastase | B. thermoproteolyticus thermolysin |
| epsilon | CLH_1920 | Oxygen labile hemolysin | C. perfringens perfringolysin |
| gamma | CLH_1861 | Clostripain | C. histolyticum clostripain | ii. Protein Sequence Alignments and Analysis

To identify the signal peptide, the sample and control sequences were analyzed in a program termed SignalP identify potential signal peptide sequences (Nielsen (2004), J. Glasgow et al., eds., Proc. Sixth Int. Conf. on Intelligent Systems for Molecular Biology, 122-130. AAAI Press, 1998). A signal peptide is usually located within the first seventy amino acids (or the N-terminus region) of the protein sequence and acts as a signal sequence for the enzyme to be secreted. The signal peptide is cleaved and the resulting protein sequence is the mature protein. Using SignalP, the user can identify the signal peptide cleavage site location in order to identify the N-terminus of the mature protein. For some sample sequences, in particular alpha toxin and beta toxin (AUX-I), however, only the mature protein was identified, not the entire protein sequence including the signal peptide sequence. Further examination revealed that the sequence fragmentation procedure employed separated the signal peptide sequence from the mature protein. The mature protein and signal sequences were reassembled and processed through the alignment tool.

Once all the protein sequences were collected, pair wise sequence alignments were constructed using MATLAB 7.0.10 (The MathWorks, Inc., 2010). Pair wise sequence alignments are direct comparisons of two sequences to determine the similarities and differences between two sequences. Both control and sample sequences were uploaded into MATLAB and an alignment was made using the Needleman-Wunsch algorithm and BLOSUM50 scoring matrix. The algorithm and scoring matrix assist in assembling the alignment as the algorithm dictates the value of each amino acid match or mismatch based off of the scoring matrix and incorporates gap values when necessary. Gaps can occur for multiple reasons, including, but not limited to, two sequences having varying lengths and to ensure that the appropriate amino acids are matching up to one another. The scoring matrix is based off of substitution rates observed frequently among sequences and serves to rate the similarity or dissimilarity between two sequences (National Center for Biotechnology Information).

The Hatheway (1990) review (Clin Microbiol Rev 3: 66-98) indicated that all five toxins were secreted proteins (exosubstances) and all five toxins had identifiable functionality. This information was used to conduct analysis of the putative CLH toxins. To analyze the protein function of the putative CLH toxins, a number of model proteins were selected based upon literature findings and BLAST results. The controls were downloaded from the National Center for Biotechnology Information (NCBI) in Fasta format.

1. Alpha (α) Toxin

Sparse information related to *C. histolyticum* alpha toxin following the work of Bowen (1952) (*Yale J Blot Med* 25:124-138) exists in the literature. Thus, the interrogation of the genome sequence for putative toxin genes was of interest. A preliminary analysis of the genome suggested that *C. histolyticum* possessed a single ORF that shares significant amino acid homology with *C. septicum* alpha toxin as determined by BLAST analysis of two databases. Therefore, the putative alpha toxin gene within *C. histolyticum* has been assigned as a homolog of *C. septicum* alpha toxin. Studied extensively by the Rodney K. Tweten laboratory, *C. septicum* alpha toxin was classified as a member of the aerolysin-like family of toxins. Notably, *C. septicum* alpha toxin does possess haemolytic activity (Ballard et al. (1992), *Infect Immun* 60: 784-790; Melton-Witt et al. (2006), *Biochem* 45: 14347-14354) and is distinct from oxygen labile hemolysins as described for *C. histolyticum* c toxin (Hatheway (1990), *Clin Microbiol Rev* 3:66-98).

The *C. septicum* alpha toxin is elaborated as an inactive preproprotein which is processed to the extracellular environment as an inactive protoxin. The protoxin then binds to receptors on the cell membrane where they are cleaved into their active structures by proteases (usually furin). A furin consensus site within the toxin is essential for activation by eukaryotic proteases. The activation involves the cleavage of 40-45 amino acids from the C-terminus. Absent the C-terminal cleavage the *C. septicum* alpha toxin is not functional. Full length *C. septicum* alpha toxin is haemolytic (Ballard et al. 1992). The active toxin is approximately 41.3 kDa (Gordon et al. 1997). Once activated, the toxins oligomerize on the cell surface into a prepore complex followed by insertion of a beta-barrel into the membrane.

The model *C. septicum* alpha toxin consists of three distinct domains termed: D1, D2, and D3. The D1 domain is involved with receptor binding and oligomerization, while the D2 domain contributes to amphipathic-hairpin structure. The D3 domain has a D3 propeptide region that includes a short carboxyl-terminal peptide cleaved at the known AT activation site (R398) and functions as an intramolecular chaperone that prevents premature oligomerization of the alpha toxin. Using saturation mutagenesis, single amino acid substitutions within each domain have allowed the determination of those residues essential for biological activity (Melton-Witt et al., 2006). Importantly, the functional assay utilized a cell viability assay to determine $LD_{50}$ doses. Thus, the relative effect of single amino acid substitutions within the entire coding region was assessed using a functional assay.

To further understand the primary structure of the CLH alpha toxin, the protein alignment, performed in MATLAB, of the model protein (*C. septicum* alpha toxin) was made with the CLH alpha toxin. The results are presented in FIG. 1.

The translated CLH putative alpha toxin has an identifiable signal sequence and has a very high probability of being a secreted protein. Thus, the first criterion of an exosubstance is achieved. There is a 75% positive homology between the *C. septicum* alpha toxin protein sequence and the CLH alpha toxin protein sequence. Multiple regions of high homology were identified between the model alpha toxin and the CLH putative alpha toxin. Such regions and essential amino acid residues are highlighted in green shading in FIG. 1.

Notably, the alignment shows multiple differences in essential amino acid residues that, based on the work of Melton-Witt et al. (2006) (Biochem 45:14347-14354), individually render the CLH_2834 & 2835 protein non-functional. Beginning with the N-terminal region of the mature protein, a 17 amino acid sequence region is missing in the CLH alpha toxin sequence which is located about 20 amino acids downstream from the putative signal peptide cleavage site. Within this 17 amino acid stretch, a W74 residue on *C. septicum* alpha toxin has been identified as a critical residue in loop 1 (L1). The lack of 17 amino acids from the D1 domain in the CLH sequence version suggests an altered structure for this domain relative to a wild type and a disruption of the receptor binding functionality.

Within the C-terminal region of the protein, several amino acid residue changes also render the CLH protein non-functional. The amino acid T302 in the *C. septicum* alpha toxin was replaced by Proline in the CLH alpha toxin. Residue E303 in the *C. septicum* alpha toxin is replaced by Threonine in the CLH alpha toxin. The studies of Melton-Witt et al. (2006) (Biochem 45: 14347-14354) indicated that each of these modifications will individually result in 0% lethality. Of note is the comparison of the activation site, or furin cleavage site, between the two sequences. The *C. septicum* alpha toxin exhibits a furin consensus cleavage site beginning with K391 and terminating at R398. This region fits the consensus furin cleavage sequence Arg-X-Lys/Arg-Arg (SEQ ID NO: 31), although the minimal cleavage sequence is Arg-X-X-Arg (SEQ ID NO: 32). The CLH putative alpha toxin has a Glutamine residue instead of Arginine in the analogous R398 position. Thus, the *C. septicum* activation site possesses the amino acid sequence, DKKRRGKRSVDS (SEQ ID NO: 26), with R398 identified as a critical residue. The CLH alpha toxin homologous sequence in the D3 peptide is NTSST-EQNVEV (SEQ ID NO: 27); beginning with N367 of SEQ ID. NO. 8. Therefore, the putative *C. histolyticum* alpha toxin furin cleavage site appears to be non-functional, and this protein, even if expressed, could not be processed by contact with eukaryotic cells furin protease to generate a functional toxin. The findings of the comparative amino acid sequence analysis are summarized in Table 3.

TABLE 3

Summary of Amino Acid Sequence Alignment Comparison for Putative CLH alpha toxin

| Protein | | Effect on Function |
|---|---|---|
| *C. septicum* α toxin Essential Amino Acid Residue | CLH 2834 & 2835 | |
| W74 | Missing | Receptor binding disrupted |
| T302 | P | Lack of lethality |
| E303 | T | Lack of lethality |
| K391-R398 | T - - - Q | Incapable of activation |

The summary of the sequence alignment analysis suggests that the putative CLH alpha toxin possess a significant number of amino acid residues differences that would make the mature protein non-functional. The phenotypic linkage to functionality for alpha toxin is the demonstration of haemolytic activity. Importantly, the Collagenase *Clostridium Histolyticum* production strain does not exhibit haemolytic activity when plated on blood agar. The results of a Blood agar hemolytic assessment are illustrated in FIG. 2.

Panel A of FIG. 2 shows the results obtained when a sample of *C. histolyticum* Clone 004 cell expansion is cultivated on Blood agar. There is no evidence of any beta hemolytic phenotype. In contrast, panel B of FIG. 2 shows the results obtained when a sample of *C. septicum* is cultivated on Blood agar. There is clear evidence of beta hemolysis that extends well beyond the area of sample application as indicated in Panel C. The images presented do not adequately represent the qualitative difference observed when one views the test articles. The appearance of beta hemolysis is easily discernable and the complete lack of any hemolysis in the *C. histolyticum* plate stands in stark contrast to the broad zone of hemolysis noted when the *C. septicum* culture (producer of a toxin) is inspected.

2. Delta (δ) Toxin

Hatheway et al. (1990) (*Clin Microbiol Rev* 3: 66-98) has defined the δ toxin of *C. histolyticum* as an elastase, primarily based on the initial research communication by Takahashi, et al. (1970) (*BBRC* 39: 1058-1064). No further substantial studies on this toxin have apparently been published since then. Four fractions demonstrating elastase activity were isolated from *C. histolyticum* by Takahashi et al. using differential ultrafiltration. The primary focus was on a fraction which passed through membranes of nominal 50 kDa cut-off membranes but was retained by membranes with a nominal 10 kDa cut-off.

Thermolysin is a zinc metalloprotease with a mature enzyme molecular weight of 34.6 kDa. Importantly, thermolysin is a model protein for a class of proteins that contain a presequence employed in secretion (signal peptide) but also a lengthy prosequence of approximately 200 amino acid residues that is two thirds the size of the mature protein. Thermolysin-like enzymes are elaborated as inactive preproproteins with the prosequence serving a role as an inhibitor of the mature enzyme and also as a chaperone to ensure proper folding of the enzyme (O'Donohue et al. (1996), *JBC* 271:26477-26481). The prosequence is autocatalytically removed by the mature enzyme portion of the molecule in the extracellular environment. Thus, the maturation pathway for thermolysin-like enzymes includes: a secretion step, the presence of a pro-mature form in the extracellular matrix, the cleavage of the prosequence, and the presence of a mature, active enzyme.

The gene sequence alignment for thermolysin and CLH_2576, the putative *C. histolyticum* delta toxin, is illustrated in FIG. 3. This image displays the full length prepromature amino acid sequence as a single unit that is theoretically transcribed as a single polypeptide. The initial 28 amino acids at the N-terminus of thermolysin are shown juxtaposed to the green shaded prosequence which terminates at Ser232. The unshaded mature amino acid sequence begins with Ile233. Using the SignalP program, the thermolysin and the CLH_2576 polypeptides are predicted to be secreted. The translated putative *C. histolyticum* delta toxin has an identifiable signal sequence and a very high probability of being a secreted protein. There is a 65% positive homology between the thermolysin protein sequence and the CLH delta toxin protein sequence.

To understand the nature of the pro and mature forms of both proteins, the individual regions were analyzed as distinct sequences with regards to functionality. The prosequence alignment is depicted in FIG. 4. There is a 57% positive homology between the two prosequence forms. A recent review of the primary structural analysis of the prosequences of over 100 thermolysin-like proteases was conducted by Demidyuk et al. (2008) (*Protein J* 27: 343-354). These investigators noted that considerable variability existed within the prosequences, alternatively termed precursors or propeptides. The prosequences were more tolerant to mutations compared to the corresponding mature enzymes. Nevertheless, regions exhibiting a high degree of conservation and substitutions in key residues were noted which may dramatically alter the function. The residues shaded green in FIG. 3 identify those amino acid residues that are critical for the prosequence to function. No differences are noted between the thermolysin and CLH_2756 sequences. Two residues corresponding to Ile183 and Arg184 in the thermolysin sequence are shaded yellow; however, the substitutions in the CLH_2756 sequence are similar amino acids that likely do not result in any alteration of function.

Importantly, there is a region of non-homology at the C-terminus of the prosequences as illustrated by the yellow shading of the CLH_2756 sequence beginning with Ser185. This region is the site of autocatalysis and suggests that the CLH_2756 sequence is not an acceptable substrate for cleavage by the active site of the mature enzyme. The criticality of the amino acid residues around the cleavage site was investigated by Wetmore et al. (1994) (*Mol Microbiol* 12:747-759), using *Bacillus cereus* thermolysin-like neutral protease as the model enzyme. These investigators determined that the processing was particularly sensitive to the nature of the amino acid three residues upstream from the cleavage site. A consensus sequence was identified for the sequence around the proprotein processing site and alterations in key residues resulted in the non-export or nonprocessing of the protein to a mature, functional enzyme. Key features of the consensus sequence were: the presence of a non-polar residue in position $P_3$ (Gly, Ala, Ile, Leu, or Val), a polar residue or Pro in position $P_1$ (Pro, Ser, His, Glu), and a non-polar residue in position $P_1'$. Additionally, the prothermolysin maturation has been shown to occur between a serine and isoleucine residue (O'Donohue et al.

(1994), *Biochem J.* 300: 599-603). To explore the sequence alignment around the cleavage site, a comparative sequence assessment of the proprotein processing sites for thermolysin and for CLH_2576 can be made by inspection. It is apparent that the CLH_2576 amino acid sequence in the proprotein processing area does not contain the appropriate amino acid arrangement to allow autocatalysis. When one conducts a theoretical exercise to interrogate the CLH_2576 amino sequence to determine if the proprotein processing site is reasonably close to the predicted site based on sequence alignment, it is clear that no adjustment allows the proper amino acid sequence to be identified. Shifting the proprotein processing site 2 residues to the C-terminal side allows for the proper arrangement of amino acids that do not violate the Wetmore et al. rules. However, the Ser-Ile rule of O'Donohue et al. (1994) (*Biochem J.* 300: 599-603) is not present. Thus, it is concluded that the proprotein form of the CLH_2576 polypeptide is not a suitable substrate for autocatalysis. The net effect is that the mature, active enzyme is not present in the cell broth of *C. histolyticum* (Clone 004).

To explore the mature forms of both proteins, the comparative sequence alignment is depicted in FIG. 5. An inspection of the sequence alignment in FIG. 5 suggests that many essential amino acids have been conserved. Notably, the AHELTHAVTD sequence (SEQ ID NO: 28) of the Mature Thermolysin, beginning with Ala140 of SEQ. ID. NO. 13 has been identified as a component of the active site for thermolysin and the high homology displayed by CLH 2576 of SEQ ID. NO. 14 suggests that CLH delta toxin is a member of the thermolysin class of proteases (Kooi et al. (1996), *J Med Microbiol* 45:219-225; Kooi, et al., (1997), *Infect Immun* 65:472-477). Multiple residues shaded in green have been identified as essential for binding or catalysis. One notable difference between the sequences of the two molecules is the GGI region beginning with G135 in thermolysin. This stretch of amino acid residues is highly conserved in thermolysin-like proteases with no defined function assigned (Frigerio et al. (1997), *Protein Eng* 10:223-230). The corresponding CLH_2576 region possesses several significant differences in this sequence. Nevertheless, the overall high degree of homology and the conservation of essential amino acid residues confirm the selection of CLH 2576 as delta toxin with predicted molecular mass of approximately 35 kDa. This assessment aligns with the information presented by Takahashi et al (1970) (*BBRC* 39: 1058-1064).

In summary, the putative CLH delta toxin has been identified using genome sequence analysis. However, the interrogation of this sequence suggests that the cleavage of the proprotein will not occur, rendering this molecule non-functional. Therefore, it is deduced that the δ toxin, if expressed and secreted in the Clone 004 derivative of *C. histolyticum* ATCC 21000, is not functional.

3. Epsilon (ε) Toxin

MacLennan et al. (1962) (*Bact Rev* 26:176-274) and Hatheway described the toxin of *C. histolyticum* as an oxygen-labile haemolysin serologically similar to those produced by other strains of *Clostridium*, such as *C. tetani, C. novyi,* and *C. septicum*. Bowen (1952) (*Yale J Blot Med* 25:124-138) demonstrated that the c toxin was expressed during the exponential phase and degraded during the stationary phase as observed for the α toxin activity, and was similarly degraded by proteinases in vitro.

An inspection of the BLAST analysis results of the *C. histolyticum* genome identified an ORF coding for a hemolysin that was in the same class as perfringolysin and tetanolysin, which are members of thiol-activated, pore forming proteins with affinity for cholesterol. Such proteins are part of a family of Cholesterol Dependent Cytolysins (CDC) and all exhibit distinctive protein sequences and unique structures. Over 25 CDC proteins have been identified with complete protein sequences available. The CDCs are a group of β-barrel pore-forming toxins secreted by various species of Gram positive bacteria all in the 50-60 kDa molecular weight range. The prototypical CDC is perfringolysin which serves as a model protein for all CDCs (Heuck et al. 2007, *JBC* 282: 22629-22637). The typical organization of a CDC includes a cleavable signal sequence to facilitate the exports to the extracellular environment as a water-soluble monomeric protein. Subsequently, the folded monomeric form binds to a target eukaryotic membrane, mediated by cholesterol binding, and then oligomerizes on the membrane surface to form arcs and ring-like structures that are responsible for the cytolysis. The CDCs are also known as thiol-activated cytolysins and were originally described as hemolysins (Billington et al., 2000).

The gene sequence alignment for perfringolysin and CLH_1920, the putative epsilon toxin, is illustrated in FIG. 6. This image displays the full length (pre plus mature) protein sequence as a single unit that is theoretically transcribed as a single polypeptide. The initial 29 amino acids at the N-terminus of perfringolysin are illustrated with a blue star above Lys 29 at the site of signal peptidase cleavage. The SignalP analysis of the CLH_1920 sequence did not identify a recognizable signal peptide cleavage site and was predicted to be a non-secreted protein. There is an 84% positive homology between the perfringolysin protein sequence and the CLH_1920 putative epsilon toxin protein sequence.

The amino acid residues shaded in green denote essential amino acids that are conserved between the two proteins. Importantly, the 11 amino acid sequence ECTGLAWEWWR (SEQ ID NO: 29), beginning with glutamine 458 of SEQ. ID. NO. 15, is an essential region that is termed the undecapeptide sequence. Along with the high degree of homology within the sequence designated as the mature protein region, this undecapeptide sequence serves to identify the CLH_1920 protein as a CDC. Therefore, the CLH_1920 protein, if elaborated as a secreted protein, would be expected to have haemolytic functionality. A single region of non-homology between the two proteins is highlighted in yellow shading. Importantly, the C-terminus of CDCs has been shown to be critical for cholesterol binding (Shimada et al., 1999, *JBC* 274: 18536-18542). The process of hemolysis by CDCs involves two critical steps prior to pore formation: binding and membrane insertion. Shimada, et al. (1999) (*JBC* 274: 18536-18542) demonstrated that modest changes to the C-terminus affected the binding step. An alteration of the 3' terminal amino acids severely reduces cholesterol binding as measured by an ELISA method. The corresponding haemolytic activity on red blood cells was coordinately reduced or eliminated depending upon the severity of the C-terminal amino acid change. An inspection of the C-terminus of the CLH_1920 sequence shows some significant differences compared to the perfringolysin sequence.

As summarized in Table 4, the haemolytic activity of the putative *C. histolyticum* epsilon toxin may be absent due to two features of the theoretical amino acid sequence. First, the molecule is predicted not be secreted; thus, the molecule would not be available for interaction with target cells. Second, the C-terminus of CLH_1920 protein does not possess a homologous region for cholesterol binding, which suggests that an important element associated with hemolysis may be defective.

TABLE 4

Summary of Amino Acid Sequence Alignment Comparison for Putative CLH epsilon toxin

| | Protein | Effect on Function |
|---|---|---|
| Perfringolysin Region | CLH 1920 Characteristic | |
| N-terminal | Missing signal peptidase cleavage sequence | Not secreted |
| C-terminal | Non-consensus | Lack of cholesterol binding/no activation |

Non-clinical toxicity studies demonstrated no clinical and morphological indications of hemolysin effects in vivo. The data generated by local and IV bolus administration support the absence of haemolytic toxins such as c toxin.

The absence of haemolytic toxins can be verified by the plating of test material on blood agar which is routinely performed at the end of each *C. histolyticum* Clone 004 fermentation, which also confirms the absence of foreign growth. The expression of haemolytic toxins results in the lysis of the blood cells, and thereby resulting in the formation of distinct halos around colonies producing haemolysins. The Collagenase *C. histolyticum* production strain does not produce halos or zones of clearance (see FIG. 2) supporting the absence of c toxin and any other haemolytic entities in the production strain. To verify the hemolytic function of a CDC, commercially available tetanolysin was applied to Blood agar to mimic the routine plating test. The results are illustrated in FIG. 7 which shows the beta hemolytic phenotype observed when 10 μcL of a 10 μg/mL solution of tetanolysin in phosphate buffered saline is applied to the surface of Blood agar, then incubated for 24 hours at 37° C. Thus, if a functional CDC were present in the test material, the beta hemolytic phenotype should be observed.

4. Clostripain or Gamma (γ)-Toxin

The gamma toxin of *C. histolyticum* has been described as clostripain, a cysteine endopeptidase (EC 3.4.22.8). Dargatz, et al. (1993) (*Mol Gen Genet* 240:140-145) cloned and sequenced the *C. histolyticum* gene for clostripain and this information was deposited in GenBank under accession number X63673 (www.ncbi.nlm.nih.gov/nuccore/X63673.1). To understand the primary structure of the CLH_1861 gamma toxin, the protein sequence alignment from MATLAB of the model protein (*C. histolyticum* clostripain) was made with the CLH_1861 gamma toxin theoretical sequence. The results are presented in FIG. 8.

An inspection of FIG. 8 shows a very high degree of homology (99%) between the model clostripain and the sequence obtained from the genome analysis. In fact, there are only 3 amino acid differences, none of which are residues identified as essential for activity. Those critical amino acids identified in literature studies as essential for functionality are shown in green shading. SignalP analysis of both proteins indicated that high secretion score and the signal cleavage site depicted with a blue star (Labrou et al. (2004). *Eur J Biochem* 271:983-992). Thus, one would predict that the CLH_1861 molecule would be secreted and functional. A residual clostripain analysis was conducted as part of routine release.

The clostripain analysis supports the merits of the sequence alignment approach for the *C. histolyticum* toxins in general. One would predict that the presence of a functional toxin gene would necessarily translate into an amino acid sequence that shared a high degree of homology with a known model protein. Further, the conservation of essential amino acid residues would also be a characteristic of a functional toxin gene.

The information obtained from the genome sequence analysis provided evidence that loci for putative alpha, delta, and epsilon toxins were present. Further analysis of the theoretical primary structure of each toxin indicated that non-functional forms of each toxin were predicted as a consequence of key defects in the amino acid sequence of each toxin. Notably, the alpha and epsilon toxins can be assigned as homologues to two classes of pore-forming, hemolytic molecules. As the end of fermentation, samples from every batch are plated onto blood agar as part of a routine purity test. The lack of halos or zones of clearance around the colonies confirm the absence of haemolytic activity in the culture and fermentation. Consequently, the absence of haemolytic halos around the end of fermentation samples demonstrate the absence of both a and c toxins on a continuing basis.

Table 5 shows the results from the sequence analysis and predicted functionality. The results confirm why Clone 004 has functionally shown the absences of toxicity and the lack haemolytic activity.

TABLE 5

Summary—Predicted Status of *C. histolyticum* Clone 4 Exosubstances

| Toxin | CLH Name | Sequence Result | Predicted Functionality |
|---|---|---|---|
| alpha | CLH_2834 & 2835 | Missing critical aa residues | Non functional; correlated through absence of haemolytic activity on blood agar plates |
| delta | CLH_2576 | Missing consensus proprotein cleavage sequence | Non-functional |
| epsilon | CLH_1920 | Signal peptidase cleavage site defective & non-consensus cholesterol binding sequence | Not secreted, non-functional correlated through absence of haemolytic activity on blood agar plates |
| gamma | CLH_1861 | Clostripain | Functional |

5. *C. histolyticum* Sequence Analysis of Beta Toxins (Collagenase I and Collagenase II)

The sequence analysis of the putative *C. histolyticum* beta toxin loci is presented in FIGS. 9 and 10. As shown in FIGS. 9A and 9B, the amino acid sequence of the mature collagenase I of clone 004 (CLH_1768 and 1769; SEQ ID NO: 3) differs from the translated colG sequence (SEQ ID NO: 19) by three amino acids. FIGS. 10A and 10B show that the amino acid sequence of the mature collagenase II of clone 004 (CLH_2116; SEQ ID NO: 4) differs from the translated colH sequence (SEQ ID NO: 20) by eight amino acids. Both collagenases are fully functional.

The patent and scientific literature referred to herein establishes the knowledge that is available to those with skill in the art. All United States patents and published or unpublished United States patent applications cited herein are incorporated by references. All published foreign patents and patent applications cited herein are hereby incorporated

REFERENCES

1. Nielsen et al. (2004) In J. Glasgow et al., eds., Proc. Sixth Int. Conf. on Intelligent Systems for Molecular Biology, 122-130. AAAI Press, 1998.
2. Hatheway (1990) Clin Microbiol Rev 3:66-98.
3. Ballard et al. (1992) Infect Immun 60:784-790.
4. Melton-Witt et al. (2006) Biochem 45:14347-14354.
5. Gordon et al. (1997) Infect immun 65:4130-4134.
6. Takahashi et al. (1970) BBRC 39:1058-1064.
7. O'Donohue & Beaumont (1996) JBC 271:26477-26481.
8. Demidyuk et al. (2008) Protein J 27:343-354.
9. Wetmore et al. (1994) Mol Microbiol 12:747-759.
10. O'Donohue et al. (1994) Biochem J. 300:599-603.
11. Kooi & Sokol (1996) J Med Microbiol 45:219-225.
12. Kooi et al. (1997) Infect Immun 65:472-477.
13. Frigerio et al. (1997) Protein Eng 10:223-230.
14. MacLennan (1962) Bact Rev 26:176-274.
15. Bowen (1952) Yale J Biol Med 25:124-138.
16. Heuck et al. (2007) JBC 282:22629-22637.
17. Billington et al. (2000) FEMS Microbiol Lett 182:197-205.
18. Shimada et al. (1999) JBC 274:18536-18542
19. Dargatz et al. (1993) Mol Gen Genet 240:140-145.
20. Labrou & Rigden (2004) Eur J Biochem 271:983-992.

While this invention has been particularly shown and described with references to preferred embodiments thereof, it will be understood by those skilled in the art that various changes in form and details may be made therein without departing from the scope of the invention encompassed by the appended claims.

SEQUENCE LISTING

```
Sequence total quantity: 30
SEQ ID NO: 1           moltype = DNA  length = 3357
FEATURE                Location/Qualifiers
source                 1..3357
                       mol_type = genomic DNA
                       organism = Clostridium histolyticum
SEQUENCE: 1
atgaaaaaaa atattttaaa gattcttatg gatagttatt ctaaagaatc taaaattcaa   60
actgtacgta gggttacgag tgtatcactt ttagcggcat atcttactat gaatacttca  120
agtttagttt tagcaaaacc aatagaaaat actaatgata ctagtataaa aaatgtggag  180
aaattaagaa atgctccaaa tgaagagaat agtaaaaagg tagaagatag taaaaatgat  240
aaggtagaac atgtggaaaa tatagaagag gcaaaagttg agcaagttgc acccgaagta  300
aaatctaaat caacttttaag aagtgcttct atagcgaata ctaattctga gaaatatgat  360
tttgagtatt taaatggttt gagctatact gaacttacaa atttaattaa aaatataaag  420
tggaatcaaa ttaatggttt atttaattat agtacaggtt ctcaaaagtt ctttggagat  480
aaaaatcgtg tacaagctat aattaatgct ttacaagaaa gtggaagaac ttacactgca  540
aatgatatga agggtataga aactttcact gaggttttaa gagctggttt ttatttaggg  600
tactataatg atggtttatc ttatttaaat gatagaaact tccaagataa atgtatacct  660
gcaatgattg caattcaaaa aaatcctaac tttaagctag gaactgcagt tcaagatgaa  720
gttataactt ctttaggaaa actaatagga aatgcttctg ctaatgctga agtagttaat  780
aattgtgtac cagttctaaa acaatttaga gaaaacttaa atcaatatgc tcctgattac  840
gttaaaggaa cagctgtaaa tgaattaatt aaaggtattg aattcgattt ttctggtgct  900
gcatatgaaa aagatgttaa gacaatgcct tggtatggaa aaattgatcc atttataaat  960
gaacttaagg ccttaggtct atatggaaat ataacaagtg caactgagtg ggcatctgat 1020
gttggaatat actatttaag taaattcggt ctttactcaa ctaaccgaaa tgacatagta 1080
cagtcacttg aaaaggctgt agatatgtat aagtatggta aaatagcctt tgtagcaatg 1140
gagagaataa cttgggatta tgatgggatt ggttctaatg gtaaaaaggt ggatcacgat 1200
aagttcttag atgatgctga aaaacattat ctgccaaaga catatacttt tgataatgga 1260
acctttatta taagagcagg ggagaaggta tccgaagaaa aaataaaaag gctatattgg 1320
gcatcaagag aagtgaagtc tcaattccat agagtagttg gcaatgataa agctttagag 1380
gtgggaaatg ccgatgatgt tttaactatg aaaatattta atagcccaga agaatataaa 1440
tttaatacca atataaatgg tgtaagcact gataatggtg gtctatatat agaaccaaga 1500
gggacttttct acacttatga gagaacacct caacaaagta tatttagtct tgaagaattg 1560
tttagacatg aatatactca ctatttacaa gcgagatatc ttgtagatgg ttatgggga 1620
caaggtccat tttatgaaaa aaatagatta acttggtttg atgaaggtac agctgaattc 1680
tttgcaggat ctacccgtac atctggtgtt ttaccaagaa aatcaatatt aggatatttg 1740
gctaaggata aagtagatca tagatactca ttaagaaga ctcttaattc agggtatgat 1800
gacagtgatt ggatgttcta taattatgga tttgcagttg cacattatct atatgaaaaa 1860
gatatgccta catttattaa gatgaataaa gctatattga atacagatgt gaaatcttat 1920
gatgaaataa taaaaaaatt aagtgatgat gcaaataaaa atacagaata tcaaaaccat 1980
attcaagagt tagcagataa atatcaagga gcaggcatac ctctagtatc agatgattac 2040
ttaaaagatc atggatataa gaaagcatct gaagtatatt ctgaaatttc aaaagctgct 2100
tctcttacaa acactagtgt aacagcagaa aaatctcaat attttaacac attcacttta 2160
agaggaactt atacaggtga aacttctaaa ggtgaattta aagattggga tgaaatgagt 2220
aaaaaaattag atggaactt ggagtccctt gctaaaaatt cttggagtgg atacaaaact 2280
ttaacagcat actttacgaa ttatagagtt acaagcgata ataaagttca atatgatgta 2340
gttttccatg gggttttaac agataatgcg gatattagta acaataaggc tccaatgcaa 2400
aaggtaactg gaccaagcac tggtgctgta ggaagaaata ttgaatttag tggaaaagat 2460
agtaaagatg aagatggtaa aatagtatca tatgattggg attttggcga tggtgcaact 2520
agtagaggca aaaattcagt acatgcttac aaaaaaacag gaaccataaa tgttacatta 2580
aaagtaactg acgataaggg tgcaacagct acagaaagct ttactataga aataaagaac 2640
gaagatacaa caacacctat aactaaagaa atggaaccta atgatgatat aaaagaggct 2700
aatggtccaa tagttgaagg tgttactgta aaaggtgatt taaatggttc tgatgatgct 2760
gatacctttct attttgatgt aaaagaagat ggtgatgtta caattgaact tccttattca 2820
gggtcatcta atttcacatg gttagttat aaagagggag acgatcaaaa ccatattgca 2880
```

-continued

```
agtggtatag ataagaataa ctcaaaagtt ggaacattta aagctacaaa aggaagacat   2940
tatgtgttta tatataaaca cgattctgct tcaaatatat cctattcttt aaacataaaa   3000
ggattaggta acgagaaatt gaaggaaaaa gaaataatg attcttctga taaagctaca    3060
gttataccaa atttcaatac cactatgcaa ggttcacttt taggtgatga ttcaagagat   3120
tattattctt ttgaggttaa ggaagaaggc gaagttaata tagaactaga taaaaaggat   3180
gaatttggtg taacatggac actacatcca gagtcaaata ttaatgacag aataaacttac  3240
ggacaagttg atggtaataa ggtatctaat aaagttaaat taagaccagg aaaatattat   3300
ctacttgttt ataaatactc aggatcagga aactatgagt taagggtaaa taaataa     3357

SEQ ID NO: 2           moltype = DNA  length = 3066
FEATURE                Location/Qualifiers
source                 1..3066
                       mol_type = genomic DNA
                       organism = Clostridium histolyticum
SEQUENCE: 2
atgaaaagga aatgtttatc taaaaggctt atgttagcta taacaatggc tacaatattt   60
acagtgaaca gtacattacc aatttatgca gctgtagata aaaataatgc aacagcagct   120
gtacaaaatg aaagtaagag gtatacagta tcatatttaa agactttaaa ttattatgac   180
ttagtagatt tgcttgttaa gactgaaatt gagaatttac cagaccttttt tcagtatagt   240
tcagatgcaa aagagttcta tggaaaataaa actcgtatga gctttatcat ggatgaaatt   300
ggtagaaggg caccacagta tacagagata gatcataaag gtattcctac tttagtagaa   360
gttgtaagag ctgattttta cttaggattc cataacaagg aattgaatga aataaataag   420
aggtctttta aagaaagggg aataccttct atattggcaa ttcaaaaaaa tcctaatttt   480
aaactaggta ctgaagttca agataaaata gtatctgcaa caggactttt agctggtaat   540
gaaacagcgc ctcagaagt tgtaaataat tttacaccaa taattcaaga ctgtatcaaa    600
aatatggaca gatatgctct tgatgattta aagtcaaaag cattatttaa tgtttttagct  660
gcacctacct atgatataac tgagtattta agagctacta aagaaaaacc agaaaacact   720
ccttggtatg gtaaaataga tgggtttata aatgaactta aaagttagc tcttatggaa    780
aaaataaatg ataataactc ttggataata gataatggta tatatcatat agcaccttta   840
gggaagttac atagcaataa taaaatagga atagaaactt aacagaggt tatgaagata    900
tatccttatt taagtatgca acatttacaa tcagcagatc aaattgagcg tcattatgat   960
tcaaaagatg ctgaaggaaa taaaatacct ttagataagt ttaaaaagga aggaaaagag  1020
aaatactgtc caaaaactta tacatttgat gatggaaaag taataataaa agctggtgct  1080
agggtagaag aagaaaaagt taaaagacta tactgggcat caaaggaagt taactctcaa  1140
ttcttttaggg tatatggaat agacaaacca ttagaagaag gtaatccaga tgatatatta  1200
acaatggtta tctacaacag tcctgaagaa tataaactta atagtgttct atacggatat  1260
gatactaata atggtggtat gtatatagag ccagatggaa cttcttcac atatgaaaga   1320
aaagctgaag aaagcacata cattagaa gaattttatta gacatgaata tacacactat   1380
ttacaaggaa gatatgcagt tcctggtcaa tggggaagaa caaaacttta tgacaatgat  1440
agattaactt ggtatgaaga aggtggagca gaattatttg caggttctac tagaacttct  1500
ggaatattac caagaaagag tatagtatca aatattcata taccacaag aataatagc    1560
tataagcttt cagacactgt acattctaaa tatggtgcta gttttgaatt ctataattat  1620
gcatgtatgt ttatggatta tatgtataat aaagatatgt attattaaa taaactaaat   1680
gatcttgcaa aaaataatga tgttgatgga tatgataatt atattagaga tttaagttct  1740
aatcatgctt taaatgataa atatcaagat catatgcagg agcgcataga aattatgaa    1800
aatttaacag tgccttttgt agctgatgat tatttagtaa gacatgctta taagaaccct  1860
aatgaaattt attctgaaat atctgaagta gcaaaattaa aggatgctaa gagtgaaagtt  1920
aagaaatcac aatattttag tacctttact ttgagaggta gttacacagg tggagcatct  1980
aaggggaaat tagaagatca aaaagcaatg aataagttta tagatgattc acttaagaaa  2040
ttagatacgt attcttggag tgggtataaa acttaactg cttatttcac taattataaa  2100
gttgactctt caaatagagt tacttatgat gtagtattcc acggatattt accaaacgaa  2160
ggtgattcca aaaattcatt accttatggc aagatcaatg gaacttacaa gggaacagag  2220
aaagaaaaaa tcaaattctc tagtgaaggc tctttcgatc cagatggtaa aatagtttct  2280
tatgaatggg atttcggaga tggtaataag agtaatgagg aaaatccaga gcattcatat  2340
gacaaggtag gaacttatac agtgaaatta aagttactg atgacaaggg agaatcttca   2400
gtatctacta ctactgcaga aataaaggat ctttcagaaa ataaacttcc agttatatat   2460
atgcatgtac taaatccgg agccttaaat caaaaagttg tttttctatgg aaaaggaaca  2520
tatgacccag atggatctat cgcaggatat caatgggact tggtgatgg aagtgatttt  2580
agcagtgaac aaaacccaag ccatgtatat actaaaaaag gtgaatatac tgtaacatta  2640
agagtaatgg acagtagtgg acaaatgagt gaaaaaacta tgaagattaa gattacagat  2700
ccggtatatc caataggcac tgaaaaagaa ccaaataaca gtaaagaaac tgcaagtggt  2760
ccaatagtac caggtatacc tgttagtgga accatagaaa atacaagtga tcaagattat  2820
ttctattttg atgttataac accaggagaa gtaaaaatag atataaataa attagggtac  2880
ggaggagcta cttgggtagt atatgatgaa aataataatg cagtatctta tgccactgat  2940
gatgggcaaa atttaagtgg aaagtttaag gcagataaac caggtagata ttacatccat  3000
ctttacatgt ttaatggtag ttatatgcca tatagaatta atatagaagg ttcagtagga  3060
agataa                                                              3066

SEQ ID NO: 3           moltype = AA   length = 1118
FEATURE                Location/Qualifiers
source                 1..1118
                       mol_type = protein
                       organism = Clostridium histolyticum
SEQUENCE: 3
MKKNILKILM DSYSKESKIQ TVRRVTSVSL LAAYLTMNTS SLVLAKPIEN TNDTSIKNVE    60
KLRNAPNEEN SKKVEDSKND KVEHVENIEE AKVEQVAPEV KSKSTLRSAS IANTNSEKYD   120
FEYLNGLSYT ELTNLIKNIK WNQINGLFNY STGSQKFFGD KNRVQAIINA LQESGRTYTA   180
NDMKGIETFT EVLRAGFYLG YYNDGLSYLN DRNFQDKCIP AMIAIQKNPN FKLGTAVQDE   240
VITSLGKLIG NASANAEVVN NCVPVLKQFR ENLNQYAPDY VKGTAVNELI KGIEFDFSGA   300
```

```
AYEKDVKTMP WYGKIDPFIN ELKALGLYGN ITSATEWASD VGIYYLSKFG LYSTNRNDIV    360
QSLEKAVDMY KYGKIAFVAM ERITWDYDGI GSNGKKVDHD KFLDDAEKHY LPKTYTFDNG    420
TFIIRAGEKV SEEKIKRLYW ASREVKSQFH RVVGNDKALE VGNADDVLTM KIFNSPEEYK    480
FNTNINGVST DNGGLYIEPR GTFYTYERTP QQSIFSLEEL FRHEYTHYLQ ARYLVDGLWG    540
QGPFYEKNRL TWFDEGTAEF FAGSTRTSGV LPRKSILGYL AKDKVDHRYS LKKTLNSGYD    600
DSDWMFYNYG FAVAHYLYEK DMPTFIKMNK AILNTDVKSY DEIIKKLSDD ANKNTEYQNH    660
IQELADKYQG AGIPLVSDDY LKDHGYKKAS EVYSEISKAA SLTNTSVTAE KSQYFNTFTL    720
RGTYTGETSK GEFKDWDEMS KKLDGTLESL AKNSWSGYKT LTAYFTNYRV TSDNKVQYDV    780
VFHGVLTDNA DISNNKAPIA KVTGPSTGAV GRNIEFSGKD SKDEDGKIVS YDWDFGDGAT    840
SRGKNSVHAY KKTGTYNVTL KVTDDKGATA TESFTIEIKN EDTTTPITKE MEPNDDIKEA    900
NGPIVEGVTV KGDLNGSDDA DTFYFDVKED GDVTIELPYS GSSNFTWLVY KEGDDQNHIA    960
SGIDKNNSKV GTFKATKGRH YVFIYKHDSA SNISYSLNIK GLGNEKLKEK ENNDSSDKAT   1020
VIPNFNTTMQ GSLLGDDSRD YYSFEVKEEG EVNIELDKKD EFGVTWTLHP ESNINDRITY   1080
GQVDGNKVSN KVKLRPGKYY LLVYKYSGSG NYELRVNK                          1118

SEQ ID NO: 4            moltype = AA  length = 1021
FEATURE                 Location/Qualifiers
source                  1..1021
                        mol_type = protein
                        organism = Clostridium histolyticum
SEQUENCE: 4
MKRKCLSKRL MLAITMATIF TVNSTLPIYA AVDKNNATAA VQNESKRYTV SYLKTLNYYD     60
LVDLLVKTEI ENLPDLFQYS SDAKEFYGNK TRMSFIMDEI GRRAPQYTEI DHKGIPTLVE    120
VVRAGFYLGF HNKELNEINK RSFKERVIPS ILAIQKNPNF KLGTEVQDKI VSATGLLAGN    180
ETAPPEVVNN FTPIIQDCIK NMDRYALDDL KSKALFNVLA APTYDITEYL RATKEKPENT    240
PWYGKIDGFI NELKKLALYG KINDNNSWII DNGIYHIAPL GKLHSNNKIG IETLTEVMKI    300
YPYLSMQHLQ SADQIERHYD SKDAEGNKIP LDKFKKEGKE KYCPKTYTFD DGKVIIKAGA    360
RVEEEKVKRL YWASKEVNSQ FFRVYGIDKP LEEGNPDDIL TMVIYNSPEE YKLNSVLYGY    420
DTNNGGMYIE PDGTFFTYER KAEESTYTLE ELFRHEYTHY LQGRYAVPGQ WGRTKLYDND    480
RLTWYEEGGA ELFAGSTRTS GILPRKSIVS NIHNTTRNNR YKLSDTVHSK YGASFEFYNY    540
ACMFMDYMYN KDMGILNKLN DLAKNNDVDG YDNYIRDLSS NHALNDKYQD HMQERIDNYE    600
NLTVPFVADD YLVRHAYKNP NEIYSEISEV AKLKDAKSEV KKSQYFSTFT LRGSYTGGAS    660
KGKLEDQKAM NKFIDDSLKK LDTYSWSGYK TLTAYFTNYK VDSSNRVTYD VVFHGYLPNE    720
GDSKNSLPYG KINGTYKGTE KEKIKFSSEG SFDPDGKIVS YEWDFGDGNK SNEENPEHSY    780
DKVGTYTVKL KVTDDKGESS VSTTTAEIKD LSENKLPVIY MHVPKSGALN QKVVFYGKGT    840
YDPDGSIAGY QWDFGDGSDF SSEQNPSHVY TKKGEYTVTL RVMDSSGQMS EKTMKIKITD    900
PVYPIGTEKE PNNSKETASG PIVPGIPVSG TIENTSDQDY FYFDVITPGE VKIDINKLGY    960
GGATWVVVDE NNNAVSYATD DGQNLSGKFK ADKPGRYYIH LYMFNGSYMP YRINIEGSVG   1020
R                                                                  1021

SEQ ID NO: 5            moltype = AA  length = 1008
FEATURE                 Location/Qualifiers
source                  1..1008
                        mol_type = protein
                        organism = Clostridium histolyticum
SEQUENCE: 5
IANTNSEKYD FEYLNGLSYT ELTNLIKNIK WNQINGLFNY STGSQKFFGD KNRVQAIINA     60
LQESGRTYTA NDMKGIETFT EVLRAGFYLG YYNDGLSYLN DRNFQDKCIP AMIAIQKNPN    120
FKLGTAVQDE VITSLGKLIG NASANAEVVN NCVPVLKQFR ENLNQYAPDY VKGTAVNELI    180
KGIEFDFSGA AYEKDVKTMP WYGKIDPFIN ELKALGLYGN ITSATEWASD VGIYYLSKFG    240
LYSTNRNDIV QSLEKAVDMY KYGKIAFVAM ERITWDYDGI GSNGKKVDHD KFLDDAEKHY    300
LPKTYTFDNG TFIIRAGEKV SEEKIKRLYW ASREVKSQFH RVVGNDKALE VGNADDVLTM    360
KIFNSPEEYK FNTNINGVST DNGGLYIEPR GTFYTYERTP QQSIFSLEEL FRHEYTHYLQ    420
ARYLVDGLWG QGPFYEKNRL TWFDEGTAEF FAGSTRTSGV LPRKSILGYL AKDKVDHRYS    480
LKKTLNSGYD DSDWMFYNYG FAVAHYLYEK DMPTFIKMNK AILNTDVKSY DEIIKKLSDD    540
ANKNTEYQNH IQELADKYQG AGIPLVSDDY LKDHGYKKAS EVYSEISKAA SLTNTSVTAE    600
KSQYFNTFTL RGTYTGETSK GEFKDWDEMS KKLDGTLESL AKNSWSGYKT LTAYFTNYRV    660
TSDNKVQYDV VFHGVLTDNA DISNNKAPIA KVTGPSTGAV GRNIEFSGKD SKDEDGKIVS    720
YDWDFGDGAT SRGKNSVHAY KKTGTYNVTL KVTDDKGATA TESFTIEIKN EDTTTPITKE    780
MEPNDDIKEA NGPIVEGVTV KGDLNGSDDA DTFYFDVKED GDVTIELPYS GSSNFTWLVY    840
KEGDDQNHIA SGIDKNNSKV GTFKATKGRH YVFIYKHDSA SNISYSLNIK GLGNEKLKEK    900
ENNDSSDKAT VIPNFNTTMQ GSLLGDDSRD YYSFEVKEEG EVNIELDKKD EFGVTWTLHP    960
ESNINDRITY GQVDGNKVSN KVKLRPGKYY LLVYKYSGSG NYELRVNK                1008

SEQ ID NO: 6            moltype = AA  length = 991
FEATURE                 Location/Qualifiers
source                  1..991
                        mol_type = protein
                        organism = Clostridium histolyticum
SEQUENCE: 6
AVDKNNATAA VQNESKRYTV SYLKTLNYYD LVDLLVKTEI ENLPDLFQYS SDAKEFYGNK     60
TRMSFIMDEI GRRAPQYTEI DHKGIPTLVE VVRAGFYLGF HNKELNEINK RSFKERVIPS    120
ILAIQKNPNF KLGTEVQDKI VSATGLLAGN ETAPPEVVNN FTPIIQDCIK NMDRYALDDL    180
KSKALFNVLA APTYDITEYL RATKEKPENT PWYGKIDGFI NELKKLALYG KINDNNSWII    240
DNGIYHIAPL GKLHSNNKIG IETLTEVMKI YPYLSMQHLQ SADQIERHYD SKDAEGNKIP    300
LDKFKKEGKE KYCPKTYTFD DGKVIIKAGA RVEEEKVKRL YWASKEVNSQ FFRVYGIDKP    360
LEEGNPDDIL TMVIYNSPEE YKLNSVLYGY DTNNGGMYIE PDGTFFTYER KAEESTYTLE    420
ELFRHEYTHY LQGRYAVPGQ WGRTKLYDND RLTWYEEGGA ELFAGSTRTS GILPRKSIVS    480
NIHNTTRNNR YKLSDTVHSK YGASFEFYNY ACMFMDYMYN KDMGILNKLN DLAKNNDVDG    540
```

```
YDNYIRDLSS NHALNDKYQD HMQERIDNYE NLTVPFVADD YLVRHAYKNP NEIYSEISEV   600
AKLKDAKSEV KKSQYFSTFT LRGSYTGGAS KGKLEDQKAM NKFIDDSLKK LDTYSWSGYK   660
TLTAYFTNYK VDSSNRVTYD VVFHGYLPNE GDSKNSLPYG KINGTYKGTE KEKIKFSSEG   720
SFDPDGKIVS YEWDFGDGNK SNEENPEHSY DKVGTYTVKL KVTDDKGESS VSTTTAEIKD   780
LSENKLPVIY MHVPKSGALN QKVVFYGKGT YDPDGSIAGY QWDFGDGSDF SSEQNPSHVY   840
TKKGEYTVTL RVMDSSGQMS EKTMKIKITD PVYPIGTEKE PNNSKETASG PIVPGIPVSG   900
TIENTSDQDY FYFDVITPGE VKIDINKLGY GGATWVVYDE NNNAVSYATD DGQNLSGKFK   960
ADKPGRYYIH LYMFNGSYMP YRINIEGSVG R                                 991

SEQ ID NO: 7              moltype = AA  length = 443
FEATURE                   Location/Qualifiers
source                    1..443
                          mol_type = protein
                          organism = Clostridium septicum
SEQUENCE: 7
MSKKSFAKKV ICTSMIAIQC AAVVPHVQAY ALTNLEEGGY ANHNNASSIK IFGYEDNEDL    60
KAKIIQDPEF IRNWANVAHS LGFGWCGGTA NPNVGQGFEF KREVGAGGKV SYLLSARYNP   120
NDPYASGYRA KDRLSMKISN VRFVIDNDSI KLGTPKVKKL APLNSASFDL INESKTESKL   180
SKTFNYTTSK TVSKTDNFKF GEKIGVKTSF KVGLEAIADS KVETSFEFNA EQGWSNTNST   240
TETKQESTTY TATVSPQTKK RLFLDVLGSQ IDIPYEGKIY MEYDIELMGF LRYTGNARED   300
HTEDRPTVKL KFGKNGMSAE EHLKDLYSHK NINGYSEWDW KWVDEKFGYL FKNSYDALTS   360
RKLGGIIKGS FTNINGTKIV IREGKEIPLP DKKRRGKRSV DSLDARLQNE GIRIENIETQ   420
DVPGFRLNSI TYNDKKLILI NNI                                          443

SEQ ID NO: 8              moltype = AA  length = 419
FEATURE                   Location/Qualifiers
source                    1..419
                          mol_type = protein
                          organism = Clostridium histolyticum
SEQUENCE: 8
MLKKSFFKKA ICASLVVLQC LILVSPAQTL ASTDLPTKGK TSIELFNYED HMAHCLGFGW    60
CFGTASKEIG EDFEFKRAEE EGKTVYYLSA RYNQNDPYAK GYYRAHDRLV MKVSNARFFI   120
DHDSLTLGKA KVISLDPLAS STLQVVNKSN SEAKTSLSFG YETTESTSKT DHVKFGEKIG   180
IKSSFNVKVP FIGEKSIETN LEFNSEQGWS NTKTNSVTTK HTISHTTTTP AKSRKKVRLN   240
VLNKKSDIPY EGKIYMEYDI EFFGFLRYTG NARKDHPTDR PSVSVKFGGK NNMSAVDHII   300
DLYKHKDING YSEWDNWWIE ENFYDRFSEY SSNVASQYFG GIISGVFTNV GGTDVKVEEG   360
RERPLKNTSS TEQNVEVQNF KSSKSKEFRV GSLTYTTPNG EQTIYPEDVS SLNANNNEN    419

SEQ ID NO: 9              moltype = AA  length = 548
FEATURE                   Location/Qualifiers
source                    1..548
                          mol_type = protein
                          organism = Bacillus proteolyticus
SEQUENCE: 9
MKMKMKLASF GLAAGLAAQV FLPYNALAST EHVTWNQQFQ TPQFISGDLL KVNGTSPEEL    60
VYQYVEKNEN KFKFHENAKD TLQLKEKKND NLGFTFMRFQ QTYKGIPVFG AVVTSHVKDG   120
TLTALSGTLI PNLDTKGSLK SGKKLSEKQA RDIAEKDLVA NVTKEVPEYE QGKDTEFVVY   180
VNGDEASLAY VVNLNFLTPE PGNWLYIIDA VDGKILNKFN QLDAAKPGDV KSITGTSTVG   240
VGRGVLGDQK NINTTYSTYY YLQDNTRGNG IFTYDAKYRT TLPGSLWADA DNQFFASYDA   300
PAVDAHYYAG VTYDYYKNVH NRLSYDGNNA AIRSSVHYSQ GYNNAFWNGS QMVYGDGDGQ   360
TFIPLSGGID VVAHELTHAV TDYTAGLIYQ NESGAINEAI SDIFGTLVEF YANKNPDWEI   420
GEDVYTPGIS GDSLRSMSDP AKYGDPDHYS KRYTGTQDNG GVHINSGIIN KAAYLISQGG   480
THYGVSVVGI GRDKLGKIFY RALTQYLTPT SNFSQLRAAA VQSATDLYGS TSQEVASVKQ   540
AFDAVGVK                                                           548

SEQ ID NO: 10             moltype = AA  length = 532
FEATURE                   Location/Qualifiers
source                    1..532
                          mol_type = protein
                          organism = Clostridium histolyticum
SEQUENCE: 10
MKKKFLSFII ISAISLNISS MTVGAKQVKE IKPPKDKESI SVLKTDLEKT KNIKSNNKEG    60
DDVTKVVKSA LKEEGNLGDF KVDNKETDVK GKKHLRSQMF IDGIPVYGSQ VIIHTNKDGQ   120
VYSVNGKVDK QPKAQSFKNR VRIKDDKAIK IAEDSLGKEI KKNKNYHSES KLYLYKVNGD   180
LQPVYLVKIS STEPEASFWH MFVSAENGKI VDKYNALSCQ ATHAQVRGVN SSGEHKILNG   240
MFENGRYFLA DSTRPSNGYI LTYDANNQEY GFPGSLFSNL TGIFDSDRQK AGVDAHHNLT   300
QVYDYYKNVL NRDSFDGKGA SIISSVHVGN NLNNAFWNGR QILFGDGDGV TFSNLAKCLE   360
VTAHEFTHAV TQSTAGLEYR FQSGALNEAF SDILGIAVHS DPNDWEIGED IYTPNVAGDA   420
LRSMSNPRLY RQPDHMKDYL YWDYSMDKGG VHYNSGIPNK AAYLMGKEVG KDSMAKIYYH   480
ALVNYLTPQS TFEDARNAVV SSAIDLHGEN SKEHKLAIKS WADVGVGEEA VR           532

SEQ ID NO: 11             moltype = AA  length = 204
FEATURE                   Location/Qualifiers
source                    1..204
                          mol_type = protein
                          organism = Bacillus proteolyticus
SEQUENCE: 11
STEHVTWNQQ FQTPQFISGD LLKVNGTSPE ELVYQYVEKN ENKFKFHENA KDTLQLKEKK    60
NDNLGFTFMR FQQTYKGIPV FGAVVTSHVK DGTLTALSGT LIPNLDTKGS LKSGKKLSEK   120
```

```
QARDIAEKDL VANVTKEVPE YEQGKDTEFV VYVNGDEASL AYVVNLNFLT PEPGNWLYII    180
DAVDGKILNK FNQLDAAKPG DVKS                                          204

SEQ ID NO: 12           moltype = AA  length = 194
FEATURE                 Location/Qualifiers
source                  1..194
                        mol_type = protein
                        organism = Clostridium histolyticum
SEQUENCE: 12
KPPKDKESIS VLKTDLEKTK NIKSNNKEGD DVTKVVKSAL KEEGNLGDFK VDNKETDVKG     60
KKHLRSQMFI DGIPVYGSQV IIHTNKDGQV YSVNGKVDKQ PKAQSFKNRV RIKDDKAIKI    120
AEDSLGKEIK KNKNYHSESK LYLYKVNGDL QPVYLVKISS TEPEASFWHM FVSAENGKIV    180
DKYNALSCQA THAQ                                                     194

SEQ ID NO: 13           moltype = AA  length = 316
FEATURE                 Location/Qualifiers
source                  1..316
                        mol_type = protein
                        organism = Bacillus proteolyticus
SEQUENCE: 13
ITGTSTVGVG RGVLGDQKNI NTTYSTYYYL QDNTRGNGIF TYDAKYRTTL PGSLWADADN     60
QFFASYDAPA VDAHYYAGVT YDYYKNVHNR LSYDGNNAAI RSSVHYSQGY NNAFWNGSQM    120
VYGDGDGQTF IPLSGGIDVV AHELTHAVTD YTAGLIYQNE SGAINEAISD IFGTLVEFYA    180
NKNPDWEIGE DVYTPGISGD SLRSMSDPAK YGDPDHYSKR YTGTQDNGGV HINSGIINKA    240
AYLISQGGTH YGVSVVGIGR DKLGKIFYRA LTQYLTPTSN FSQLRAAAVQ SATDLYGSTS    300
QEVASVKQAF DAVGVK                                                   316

SEQ ID NO: 14           moltype = AA  length = 307
FEATURE                 Location/Qualifiers
source                  1..307
                        mol_type = protein
                        organism = Clostridium histolyticum
SEQUENCE: 14
VRGVNSSGEH KILNGMFENG RYFLADSTRP SNGYILTYDA NNQEYGFPGS LFSNLTGIFD     60
SDRQKAGVDA HHNLTQVYDY YKNVLNRDSF DGKGASIISS VHVGNNLNNA FWNGRQILFG    120
DGDGVTFSNL AKCLEVTAHE FTHAVTQSTA GLEYRFQSGA LNEAFSDILG IAVHSDPNDW    180
EIGEDIYTPN VAGDALRSMS NPRLYRQPDH MKDYLYWDYS MDKGGVHYNS GIPNKAAYLM    240
GKEVGKDSMA KIYYHALVNY LTPQSTFEDA RNAVVSSAID LHGENSKEHK LAIKSWADVG    300
VGEEAVR                                                             307

SEQ ID NO: 15           moltype = AA  length = 500
FEATURE                 Location/Qualifiers
source                  1..500
                        mol_type = protein
                        organism = Clostridium perfringens
SEQUENCE: 15
MIRFKKTKLI ASIAMALCLF SQPVISFSKD ITDKNQSIDS GISSLSYNRN EVLASNGDKI     60
ESFVPKEGKK TGNKFIVVER QKRSLTTSPV DISIIDSVND RTYPGALQLA DKAFVENRPT    120
ILMVRKPIN INIDLPGLKG ENSIKVDDPT YGKVSGAIDE LVSKWNEKYS STHTLPARTQ     180
YSESMVYSKS QISSALNVNA KVLENSLGVD FNAVANNEKK VMILAYKQIF YTVSADLPKN    240
PSDLFDDSVT FNDLKQKGVS NEAPPLMVSN VAYGRTIYVK LETTSSSKDV QAAFKALIKN    300
TDIKNSQQYK DIYENSSFTA VVLGGDAQEH NKVVTKDFDE IRKVIKDNAT FSTKNPAYPI    360
SYTSVFLKDN SVAAVHNKTD YIETTSTEYS KGKINLDHSG AYVAQFEVAW DEVSYDKEGN    420
EVLTHKTWDG NYQDKTAHYS TVIPLEANAR NIRIKARECT GLAWEWWRDV ISEYDVPLTN    480
NINVSIWGTT LYPGSSITYN                                               500

SEQ ID NO: 16           moltype = AA  length = 520
FEATURE                 Location/Qualifiers
source                  1..520
                        mol_type = protein
                        organism = Clostridium histolyticum
SEQUENCE: 16
MKITKKGLRS LSRLMLITMI TGLTYNYHLG SSFNGNRVVL ANPNTKTDNL IKNNSDEIDE     60
KIYGLSYDPY KILSYNGEKV ENFVPAECSE NSGKFTVIKR EKKNISDSTT DISIMDSIND    120
RTYPGAIQLA NRDLIENKPN LISCERKPIT ISVDLPGMGE DGKKVVNSPT YSSVNSAINY    180
LLDTWNSKYS SKYTIPTRMN YSDTMVYSKS QLSTMFGCNF KTLSKSLNID FDSIFKGEKK    240
AMILSYKQIF YTVSVDGPNR PSDLFGYSVT SKSLALKGVN NDNPPAYVSN VAYGRTVYVK    300
LETTSSSKV KAAFKALVEN QDISSNAEYK DIINQSSFTA TVLGGGAQKH NKVVTKDFDV    360
IRNIIKNNSV YSPQNPGYPI SYTSTFLKDN KIATVNNRTE YIETTATEYD SGKIMLDHSG    420
VYVAQFEVTW DEVSYDKQGN EIIEHKSWSG NNSDRTAHFN TELYLKGNAR NISIKAKECT    480
GLAWEWWRTV VDAKNLPLVK ERKLSIWGTT LYPRYSMEEK                          520

SEQ ID NO: 17           moltype = AA  length = 526
FEATURE                 Location/Qualifiers
source                  1..526
                        mol_type = protein
                        organism = Clostridium histolyticum
SEQUENCE: 17
MLRRKVSTLL MTALITTSFL NSKPVYANPV TKSKDNNLKE VQQVTSKSNK NKNQKVTIMY     60
```

```
YCDADNNLEG SLLNDIEEMK TGYKDSPNLN LIALVDRSPR YSSDEKVLGE DFSDTRLYKI   120
EHNKANRLDG KNEFPEISTT SKYEANMGDP EVLKKFIDYC KSNYEADKYV LIMANHGGGA   180
REKSNPRLNR AICWDDSNLD KNGEADCLYM GEISDHLTEK QSVDLLAFDA CLMGTAEVAY   240
QYRPGNGGFS ADTLVASSPV VWGPGFKYDK IFDRIKAGGG TNNEDDLTLG GKEQNFDPAT   300
ITNEQLGALF VEEQRDSTHA NGRYDQHLSF YDLKKAESVK RAIDNLAVNL SNENKKSEIE   360
KLRGSGIHTD LMHYFDEYSE GEWVEYPYFD VYDLCEKINK SENFSSKTKD LASNAMNKLN   420
EMIVYSFGDP SNNFKEGKNG LSIFLPNGDK KYSTYYTSTK IPHWTMQSWY NSIDTVKYGL   480
NPYGKLSWCK DGQDPEINKV GNWFELLDSW FDKTNDVTGG VNHYQW                 526

SEQ ID NO: 18              moltype = AA   length = 526
FEATURE                    Location/Qualifiers
source                     1..526
                           mol_type = protein
                           organism = Clostridium histolyticum
SEQUENCE: 18
MLRRKVSTLL MTALITTSFL NSKPVYANPV TKSKDNNLKE VQQVISKSNK NKNQKVTIMY    60
YCDADNNLEG SLLNDIEEMK TGYKDSPNLN LIALVDRSPR YSSDEKVLGE DFSDTRLYKI   120
ELNKANRLDG KNEFPEISTT SKYEANMGDP EVLKKFIDYC KSNYEADKYV LIMANHGGGA   180
REKSNPRLNR AICWDDSNLD KNGEADCLYM GEISDHLTEK QSVDLLAFDA CLMGTAEVAY   240
QYRPGNGGFS ADTLVASSPV VWGPGFKYDK IFDRIKAGGG TNNEDDLTLG GKEQNFDPAT   300
ITNEQLGALF VEEQRDSTHA NGRYDQHLSF YDLKKAESVK RAIDNLAVNL SNENKKSEIE   360
KLRGSGIHTD LMHYFDEYSE GEWVEYPYFD VYDLCEKINK SENFSSKTKD LASNAMNKLN   420
EMIVYSFGDP SNNFKEGKNG LSTFLPNGDK KYSTYYTSTK IPHWTMQSWY NSIDTVKYGL   480
NPYGKLSWCK DGQDPEINKV GNWFELLDSW FDKTNDVTGG VNHYQW                 526

SEQ ID NO: 19              moltype = AA   length = 1118
FEATURE                    Location/Qualifiers
source                     1..1118
                           mol_type = protein
                           organism = Clostridium histolyticum
SEQUENCE: 19
MKKNILKILM DSYSKESKIQ TVRRVTSVSL LAVYLTMNTS SLVLAKPIEN TNDTSIKNVE    60
KLRNAPNEEN SKKVEDSKND KVEHVKNIEE AKVEQVAPEV KSKSTLRSAS IANTNSEKYD   120
FEYLNGLSYT ELTNLIKNIK WNQINGLFNY STGSQKFFGD KNRVQAIINA LQESGRTYTA   180
NDMKGIETFT EVLRAGFYLG YYNDGLSYLN DRNFQDKCIP AMIAIQKNPN FKLGTAVQDE   240
VITSLGKLIG NASANAEVVN NCVPVLKQFR ENLNQYAPDY VKGTAVNELI KGIEFDFSGA   300
AYEKDVKTMP WYGKIDPFIN ELKALGLYGN ITSATEWASD VGIYYLSKFG LYSTNRNDIV   360
QSLEKAVDMY KYGKIAFVAM ERITWDYDGI GSNGKKVDHD KFLDDAEKHY LPKTYTFDNG   420
TFIIRAGDKV SEEEKIKRLYW ASREVKSQFH RVVGNDKALE VGNADDVLTM KIFNSPEEYK  480
FNTNINGVST DNGGLYIEPR GTFYTYERTP QQSIFSLEEL FRHEYTHYLQ ARYLVDGLWG   540
QGPFYEKNRL TWFDEGTAEF FAGSTRTSGV LPRKSILGYL AKDKVDHRYS LKKTLNSGYD   600
DSDWMFYNYG FAVAHYLYEK DMPTFIKMNK AILNTDVKSY DEIIKKLSDD ANKNTEYQNH   660
IQELADKYQG AGIPLVSDDY LKDHGYKKAS EVYSEISKAA SLTNTSVTAE KSQYFNTFTL   720
RGTYTGETSK GEFKDWDEMS KKLDGTLESL AKNSWSGYKT LTAYFTNYRV TSDNKVQYDV   780
VFHGVLTDNA DISNNKAPIA KVTGPSTGAV GRNIEFSGKD SKDEDGKIVS YDWDFGDGAT   840
SRGKNSVHAY KKAGTYNVTL KVTDDKGATA TESFFTIEIKN EDTTTPITKE MEPNDDIKEA  900
NGPIVEGVTV KGDLNGSDDA DTFYFDVKED GDVTIELPYS GSSNFTWLVY KEGDDQNHIA   960
SGIDKNNSKV GTFKSTKGRH YVFIYKHDSA SNISYSLNIK GLGNEKLKEK ENNDSSDKAT  1020
VIPNFNTTMQ GSLLGDDSRD YYSFEVKEEG EVNIELDKKD EFGVTWTLHP ESNINDRITY  1080
GQVDGNKVSN KVKLRPGKYY LLVYKYSGSG NYELRVNK                         1118

SEQ ID NO: 20              moltype = AA   length = 1021
FEATURE                    Location/Qualifiers
source                     1..1021
                           mol_type = protein
                           organism = Clostridium histolyticum
SEQUENCE: 20
MKRKCLSKRL MLAITMATIF TVNSTLPIYA AVDKNNATAA VQNESKRYTV SYLKTLNYYD    60
LVDLLVKTEI ENLPDLFQYS SDAKEFYGNK TRMSFIMDEI GRRAPQYTEI DHKGIPTLVE   120
VVRAGFYLGF HNKELNEINK RSFKERVIPS ILAIQKNPNF KLGTEVQDKI VSATGLLAGN   180
ETAPPEVVNN FTPILQDCIK NIDRYALDDL KSKALFNVLA APTYDITEYL RATKEKPENT   240
PWYGKIDGFI NELKKLALYG KINDNNSWII DNGIYHIAPL GKLHSNNKIG IETLTEVMKV   300
YPYLSMQHLQ SADQIKRHYD SKDAEGNKIP LDKFKKEGKE KYCPKTYTFD DGKVIIKAGA   360
RVEEEKVKRL YWASKEVNSQ FFRVYGIDKP LEEGNPDDIL TMVIYNSPEE YKLNSVLYGY   420
DTNNGGMYIE PEGTFFFTYER EAQESTYTLE ELFRHEYTHY LQGRYAVPGQ WGRTKLYDND   480
RLTWYEEGGA ELFAGSTRTS GILPRKSIVS NIHNTTRNNR YKLSDTVHSK YGASFEFYNY   540
ACMFMDYMYN KDMGILNKLN DLAKNNDVDG YDNYIRDLSS NYALNDKYQD HMQERIDNYE   600
NLTVPFVADD YLVRHAYKNP NEIYSEISEV AKLKDAKSEV KSQYFSTFT LRGSYTGGAS    660
KGKLEDQKAM NKFIDDSLKK LDTYSWSGYK TLTAYFTNYK VDSSNRVTYD VVFHGYLPNE   720
GDSKNSLPYG KINGTYKGTE KEKIKFSSEG SFDPDGKIVS YEWDFGDGNK SNEENPEHSY   780
DKVGTYTVKL KVTDDKGESS VSTTTAEIKD LSENKLPVIY MHVPKSGALN QKVVFYGKGT   840
YDPDGSIAGY QWDFGDGSDF SSEQNPSHVY TKKGEYTVTL RVMDSSGQMS EKTMKIKITD   900
PVYPIGTEKE PNNSKETASG PIVPGIPVSG TIENTSDQDY FYPDVITPGE VKIDINKLGY   960
GGATWVVDYE NNNAVSYATD DGQNLSGKFK ADKPGRYYIH LYMFNGSYMP YRINIEGSVG  1020
R                                                                 1021

SEQ ID NO: 21              moltype = DNA   length = 1263
FEATURE                    Location/Qualifiers
source                     1..1263
```

```
                    mol_type = genomic DNA
                    organism = Clostridium histolyticum
SEQUENCE: 21
atgttaaaaa aatctttttt taaaaaggca atttgcgcat ctttggtggt gctacaatgt    60
ttgatattag tgtcaccagc tcaaacattg gcatcaacag atttgccgac aaaaggaaaa   120
acttcaattg aactatttaa ctatgaagat cattaaatgg ctcattgttt gggatttgga   180
tggtgcttcg gtacagcatc aaaagaaata ggggaagatt ttgaatttaa aagagcagaa   240
gaagaaggaa aaacagtata ttatttatca gctagataca atcaaaatga tccttacgct   300
aaaggctatt atcgcgcgca tgataggctt gttatgaagg ttagtaatgc taggtttttt   360
atcgatcatg attcattaac tttaggaaaa gctaaagtta taagtctaga tccactggca   420
tcatcaactc ttcaagtagt aaataaaagt aattctgaag ctaaaacatc attatctttt   480
ggatatgaaa ctactgaaag tacttccaaa acggatcacg ttaaattcgg agaaaaaatt   540
ggaattaagt catcatttaa tgttaaagtt ccatttatag gagaaaaatc aatttgaaaca   600
aatcttgaat tcaattcaga gcagggttgg tccaatacga aaactaactc tgtaactact   660
aaacatacaa tttctcatac aacaacaaca cctgcaaaga gcaggaaaaa ggtacgatta   720
aatgttctta taaaaagtc cgacatacca tatgagggta agatatatat ggaatatgat    780
atagagtttt ttggtttttt aagatatact ggaaatgcgc gtaaagatca tcctacagat   840
agacctagtg tatcagtaaa attttggggga aaaaataata tgagtgcggt agatcatatt   900
atagatttgt acaagcataa agatattaat ggctattcag aatgggattg gaattggatt   960
gaagaaaatt tttatgatag atttagtgaa tattcatcta atgttgctag tcaatatttt  1020
gggggcatta tttctggtgt atttactaat gtgggtggaa cagatgtaaa agttgaagaa  1080
ggtagagaaa ggccacttaa aaaatacaagt tctacagaaa gtaacagaat agtacagaat  1140
tttaaaagct ctaaatctaa agagtttaga gtgggtagtt taacatatac tactcctaat  1200
ggagaacaga ccatatatcc tgaagacgta tcatctctta acgctaacaa caatgagaat  1260
taa                                                                 1263

SEQ ID NO: 22          moltype = DNA  length = 1599
FEATURE                Location/Qualifiers
source                 1..1599
                       mol_type = genomic DNA
                       organism = Clostridium histolyticum
SEQUENCE: 22
atgaaaaaaa aatttttaag ttttattatt atttctgcca tatcacttaa catttcttct    60
atgactgtgg gggcaaagca agtgaaagaa atcaaacctc caaaagataa agaatctatt   120
tctgtattaa aaacagattt agaaaaaacc aagaatataa aatctaataa taaggagggg   180
gatgatgtaa caaaagtagt taagagtgct ttaaaagaag aaggcaattt aggagatttt   240
aaggttgata ataaagaaac tgatgtaaaa ggtaaaagc acttgcgttc acaaatgttt   300
atagatggta ttcctgtata tggtagtcaa gttataattc atactaataa agatggacaa   360
gtatatagcg taaatggaaa agtagataaa cagcctaaag ctcaatcttt taagaaccgt   420
gtaaggatta aggacgataa agctattaaa atagcagaag acagtttagg taaggaaata   480
aagaaaaaca aaaattatca ttctgaaagt aagttgtacc tatacaaggt taatggagat   540
ttacaacctg tgtatttggt aaagatatca tctacagaac cagaagcttc attttggcat   600
atgttttgtaa gtgctgaaaa tggaaagata gttgataagt ataataagct ttt atcatgccaa   660
gctacacatg ctcaagtaag aggagttaat agcagtggga agcataaaat cttaaatggt   720
atgtttgaaa atggaagata ttttttagca gattcaacaa gaccttcaaa tggatatata   780
ttaacatatg atgctaataa ccaagagtat ggtttcccag tagcttatt tagtaattta   840
acaggcattt ttgatagtga tagacaaaag gcaggagtag atgctcacca taatctaact   900
caagtatatg attattataa aaatgtttta aatagagata gttttgatgg aaaaggtgct   960
agtataaatt cttctgtgca tgtaggaaat aatttaaata tgctttctg gaatggtaga  1020
caaatacttt ttggtgatgg agacggagtt acatttagta acctagcaaa atgtttagaa  1080
gttactgccc atgaatttac acatgcagtt actcaaagta ctgcaggtct agaatataga  1140
tttcaatctg gtgctctaaa tgaagctttt tctgatattt taggtatagc tgttcacagt  1200
gatccaaatg attgggaaat tggagaagat atatacactc taatgtagc aggagatgct  1260
ttaagaagta tgtcaaatcc tagattatat agacaaccag accatatgaa ggactatta  1320
tattgggatt attcaatgga taaaggtgga gttcattata attcaggtat tccaaataa  1380
gcagcttatt tgatgggaaa agaagttgga aaagattcaa tggctaaaat ttattatcat  1440
gctttagtga attatttaac tcctcaaagt acatttgaag atgctagaaa tgcagtagta  1500
tcatctgcaa tagatttaca tggtgagaat agtaaagaac ataaacttgc tataaaatct  1560
tgggcagatg taggcgttgg agaagaggca gtaagataa                          1599

SEQ ID NO: 23          moltype = DNA  length = 1563
FEATURE                Location/Qualifiers
source                 1..1563
                       mol_type = genomic DNA
                       organism = Clostridium histolyticum
SEQUENCE: 23
atgaagatta caaagaaagg cttaagatca ttatcacgct taatgttaat tactatgata    60
acaggattaa catacaatta tcacctaggt agtagcttta atgggaatcg agtagtactt   120
gcaaatccaa atacaaaaac agataattta attaagaata taatgtgatga aatagacgaa   180
aagatttatg gattgtctta tgatccatat aaaatattat cttataatgg agaaaaggtt   240
gaaaactttg ttccagctga atgttccgag aattccggaa aatttactgt aataaaacgt   300
gaaaagaaaa atatttcaga ttcaactaca gatatttcaa taatggattc aataaatgat   360
agaacttatc ctggtgctat acaactagca aataggggatc ttatagaaaa taagcctaat   420
ttaatttcat gcgagagaaa acctattact ataagtagtg atttacctgg tatgggtag   480
gatgggaaaa aggttgttaa ttctccaaca tactcttcag ttaattcagc aataaattat   540
ttgctagata catggaattc aaaatattca tctaaatata ctataccta aaggatgaat   600
tattctgata ctatggtgta tagtaaatca cagttatcta caatgtttgg atgtaacttt   660
aaaactttaa gtaaatcctt aaatatagat tttgattcta tatttaaagg cgaaaaaaag   720
gctatgatct atcatataaa acaaattttc tacacagtga gtgtagatgg acctaatcgc   780
```

```
ccatcagatt tatttggtta cagtgtaact tctaagagct tagctttaaa aggagtaaat    840
aatgataatc ctccagcata cgtttccaat gttgcatatg gtagaactgt ttatgtaaaa    900
ctagagacaa catctaagag ttcaaaggtt aaagcagcat ttaaggcatt agtagagaat    960
caagatataa gtagtaatgc agaatataaa gacataataa atcaaagttc atttacagct   1020
actgttctag gtgtgaggagc acaaaaacac aataaagtag ttactaaaga tttcgatgta   1080
```

```
ccatcagatt tatttggtta cagtgtaact tctaagagct tagctttaaa aggagtaaat    840
aatgataatc ctccagcata cgtttccaat gttgcatatg gtagaactgt ttatgtaaaa    900
ctagagacaa catctaagag ttcaaaggtt aaagcagcat ttaaggcatt agtagagaat    960
caagatataa gtagtaatgc agaatataaa gacataataa atcaaagttc atttacagct   1020
actgttctag gtgaggagc acaaaaacac aataaagtag ttactaaaga tttcgatgta   1080
ataagaaata ttattaaaaa taattcagta tatagcccac aaaatcctgg atatcctatt   1140
tcatatacaa gtacattttt aaaagacaat aaaatagcaa ctgtaaacaa tagaacagaa   1200
tatatagaaa caactgcaac agaatacgat agcggcaaaa taatgcttga ccatagtgga   1260
gtttatgttg ctcaatttga agtaacctgg gatgaagtta gttatgacaa acaaggaaat   1320
gaaataattg agcataaatc ttggtctgga aacaatagtg atagaacagc tcactttaat   1380
acagaactat atttaaaagg aaatgcaaga aacatttcta taaaagcaaa agaatgtaca   1440
ggccttgctt gggaatggtg agaaactgtt gtagatgcta aaaatttacc acttgtaaaa   1500
gaaagaaagt tatcaatatg gggtacaaca ttatatccta gatattctat ggaagagaaa   1560
taa                                                                1563

SEQ ID NO: 24           moltype = DNA  length = 1581
FEATURE                 Location/Qualifiers
source                  1..1581
                        mol_type = genomic DNA
                        organism = Clostridium histolyticum
SEQUENCE: 24
atgttaagaa gaaaagtatc aacactatta atgacagctt tgataactac ttcattttta     60
aattccaaac ccgtatatgc aaatccagta actaaatcca aggataataa cttaaaagaa    120
gtacaacaag ttataagcaa gagtaataaa aacaaaaatc aaaaagtaac tattatgtac    180
tattgcgacg cagataataa cttggaagga agtctattaa atgatatcga ggaaatgaaa    240
acaggatata aggatagtcc taatttaaat ttaattgctc ttgtagacag atcccaaga    300
tatagcagtg acgaaaaagt tttaggtgaa gatttagtg atacacgtct ttataagatt    360
gaactcaata aggcaaatag attagacggt aaaaatgaat ttccagaaat aagtactact    420
agtaaatatg aagctaacat gggggatcct gaagttctta aaaatttat tgattattgt    480
aaatctaatt atgaggctga taaatatgtg cttataatgg ttgtggtgta    540
agggaaaaat caaatccaag attaaataga gcaatttgct gggatgatag taaccttgat    600
aaaaatggtg aagcagactg cctttatatg ggtgaaattt cagatcattt aacagaaaaa    660
caatcagtta atttacttgc ctttgatgca tgccttatgg gaactgcaga agtagcgtat    720
cagtatagac caggtaatgg aggatttttc gccgatactt tagttgcttc aagcccagta    780
gtttgggtgtc ctggattcaa atatgataag attttcgata ggataaaagc tggtggagga    840
actaataatg aggatgattt aactttaggt ggtaaagaac aaaactttga tcctgcaacc    900
attaccaatg agcaattagg tgcattattt gtagaagagc aaagagactc aacacatgcc    960
aatggtcgct atgatcaaca cttaagcttt tatgatttaa agaaagctga atcagtaaaa   1020
agagccatag ataatttagc tgttaatcta agtaatgaaa acaaaaaatc tgaaattgaa   1080
aaattaagag gaagtggaat tcatacagat ttaatgcatt acttcgatga atattctgaa   1140
ggagaatggg ttgaatatcc ttattttgac gtgtatgatt tatgtgaaaa aataaataaa   1200
agtgaaaatt ttagtagtaa aactaaagat ttagcttcaa atgctatgaa taaattaaat   1260
gaaatgatag tttattcttt tggagaccct agtaataatt ttaaagaagg aaaaaatgga   1320
ttgagtacat tcttacctaa tggagataaa aaatattcaa cttattatac atcaaccaag   1380
atacctcatt ggactatgca aagttggtat aattcaatag atacagttaa atatggattg   1440
aatccttacg gaaaattaag ttggtgtaaa gatggacaag atcctgaaat aaataaagtt   1500
ggaaattggt ttgaacttct agattcttgg tttgataaaa ctaatgatgt aactggagga   1560
gttaatcatt accaatggta a                                            1581

SEQ ID NO: 25           moltype = AA  length = 6
FEATURE                 Location/Qualifiers
REGION                  1..6
                        note = Description of Artificial Sequence: Synthetic 6xHis
                        tag
source                  1..6
                        mol_type = protein
                        organism = synthetic construct
SEQUENCE: 25
HHHHHH                                                                6

SEQ ID NO: 26           moltype = AA  length = 12
FEATURE                 Location/Qualifiers
source                  1..12
                        mol_type = protein
                        organism = Clostridium septicum
SEQUENCE: 26
DKKRRGKRSV DS                                                        12

SEQ ID NO: 27           moltype = AA  length = 11
FEATURE                 Location/Qualifiers
source                  1..11
                        mol_type = protein
                        organism = Clostridium histolyticum
SEQUENCE: 27
NTSSTEQNVE V                                                         11

SEQ ID NO: 28           moltype = AA  length = 10
FEATURE                 Location/Qualifiers
source                  1..10
```

|  |  |  |
|---|---|---|
| SEQUENCE: 28<br>AHELTHAVTD | mol_type = protein<br>organism = Bacillus proteolyticus | 10 |
| SEQ ID NO: 29<br>FEATURE<br>source<br><br>SEQUENCE: 29<br>ECTGLAWEWW R | moltype = AA  length = 11<br>Location/Qualifiers<br>1..11<br>mol_type = protein<br>organism = Clostridium perfringens | 11 |
| SEQ ID NO: 30<br>FEATURE<br>source<br><br>SEQUENCE: 30<br>A